United States Patent
Chan et al.

(10) Patent No.: US 12,404,308 B2
(45) Date of Patent: Sep. 2, 2025

(54) IN VIVO IMMOBILIZATION OF PROTEINS

(71) Applicant: The Chinese University of Hong Kong, Shatin (CN)

(72) Inventors: Michael Chan, Kowloon (CN);
Bradley Heater, Shatin (CN);
Marianne Lee, Kowloon (CN)

(73) Assignee: The Chinese University of Hong Kong, Shatin (CN)

( * ) Notice: Subject to any disclaimer, the term of this patent is extended or adjusted under 35 U.S.C. 154(b) by 479 days.

(21) Appl. No.: 17/605,993

(22) PCT Filed: Apr. 24, 2020

(86) PCT No.: PCT/CN2020/086652
§ 371 (c)(1),
(2) Date: Oct. 22, 2021

(87) PCT Pub. No.: WO2020/216322
PCT Pub. Date: Oct. 29, 2020

(65) Prior Publication Data
US 2023/0203105 A1     Jun. 29, 2023

Related U.S. Application Data

(60) Provisional application No. 62/839,400, filed on Apr. 26, 2019.

(51) Int. Cl.
| C07K 14/325 | (2006.01) |
| C12N 9/20 | (2006.01) |
| C12N 15/70 | (2006.01) |
| C12N 15/75 | (2006.01) |

(52) U.S. Cl.
CPC ............ *C07K 14/325* (2013.01); *C12N 15/70* (2013.01); *C12N 15/75* (2013.01); *C07K 2319/00* (2013.01)

(58) Field of Classification Search
CPC .... C07K 14/325; C07K 2319/00; C07K 9/20; C12N 15/70; C12N 15/75; C12P 21/02
See application file for complete search history.

(56) References Cited

FOREIGN PATENT DOCUMENTS

| WO | 2010/141953 A2 | 12/2010 |
| WO | 2013/085540 A2 | 6/2013 |
| WO | 2018/028371 A1 | 2/2018 |

OTHER PUBLICATIONS

Heater, at al., "Direct production of a genetically-encoded immobilized biodiesel catalyst", Scientific Reports, vol. 8, No. 1 (Aug. 24, 2018).
European Search Report from European Patent Application No. 20795849.7, mailed May 12, 2023, 7 pages.
Abe, et al., "Design of Enzyme-Encapsulated Protein Containers by In Vivo Crystal Engineering," Advanced Materials, vol. 27, No. 48, pp. 7951-7956 (Oct. 2015).
Abe, et al., "Crystal Engineering of Self-Assembled Porous Protein Materials in Living Cells," ACS Nano, vol. 11, No. 3, pp. 2410-2419 (Jan. 2017).
Li, et al., "Crystal structure of insecticidal δ-endotoxin from *Bacillus thuringiensis* at 2.5 A resolution," Nature, vol. 353, pp. 815-821 (Oct. 1991).
Nair, et al., "Cry Protein Crystals: A Novel Platform for Protein Delivery," PLOS One, No. 6, vol. 10 e0127669, 16 pages (Jun. 2015).
Sawaya, et al., "Protein crystal structure obtained at 2. 9 A resolution from injecting bacterial cells into an X-ray free-electron laser beam," PNAS, No. 35, vol. 111, pp. 12769-12774 (Sep. 2014).
Sun, et al., "Cry Protein Crystal-Immobilized Metallothioneins for Bioremediation of Heavy Metals from Water," Crystals, No. 6, vol. 9 e287, 8 pages (Jun. 2019).
Yang, et al., "Targeted delivery of antimicrobial peptide by Cry Protein Crystal to treat intramacrophage infection," Biomaterials, vol. 217, e119286, 14 pages (Jun. 2019).
UniProt database. "UniProtKB-P30331" UniProt database (Jan. 2007)a.
International Search Report and Written Opinion for International PCT Application No. PCT/CN2020/086652, mailed Jul. 22, 2020, 10 pages.

*Primary Examiner* — Satyendra K Singh
(74) *Attorney, Agent, or Firm* — Kilpatrick Townsend & Stockton LLP

(57) ABSTRACT

Provide is a novel system for immobilizing recombinantly produced proteins by entrapping them in crystals of co-expressed proteins that are capable of self-crystallization. Related compositions and as well as methods of making and using the immobilized proteins are also described.

23 Claims, 27 Drawing Sheets
Specification includes a Sequence Listing.

Figure 4

Cry3Aa[PML^VG] (1:1 Cry3Aa:PML)

3P → [Cry3Aa]—(RBS)—[PML^VG]

3PPML^VG [Cyt13A]

3P → [PML^VG]  Cyt1-1 → Cyt1-2 → [Cry3Aa]

3A[PML^VG]² (1:2 Cry3Aa:PML)

3P → [Cry3Aa]—(RBS)—[PML^VG]—(RBS)—[PML^VG]

3P3A[3PPML^VG] (1:2 Cry3Aa:PML)

3P → [Cry3Aa]   3P → [PML^VG]

mRNA

Figure 8
A
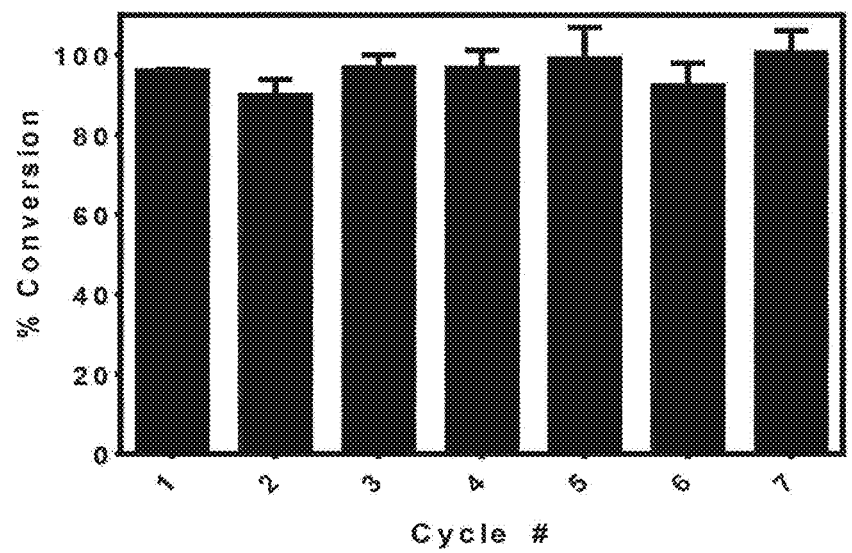
B
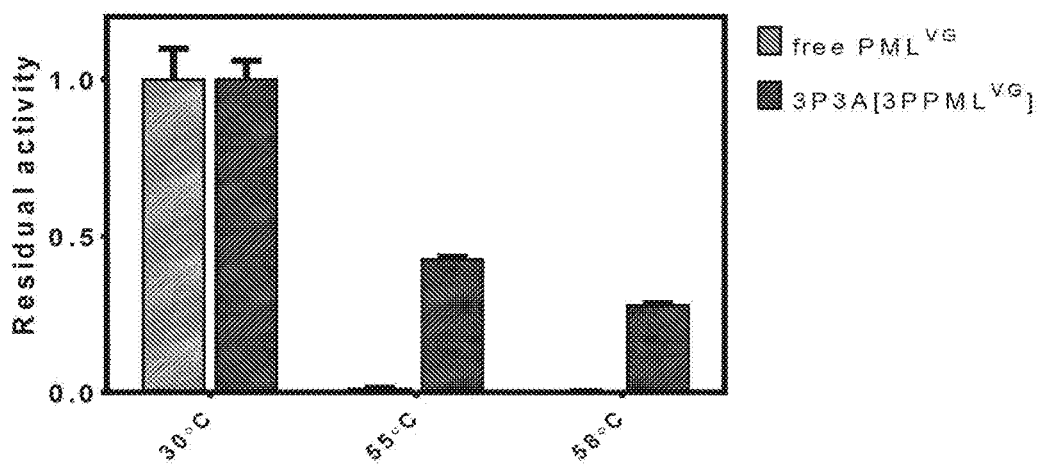

Figure 9
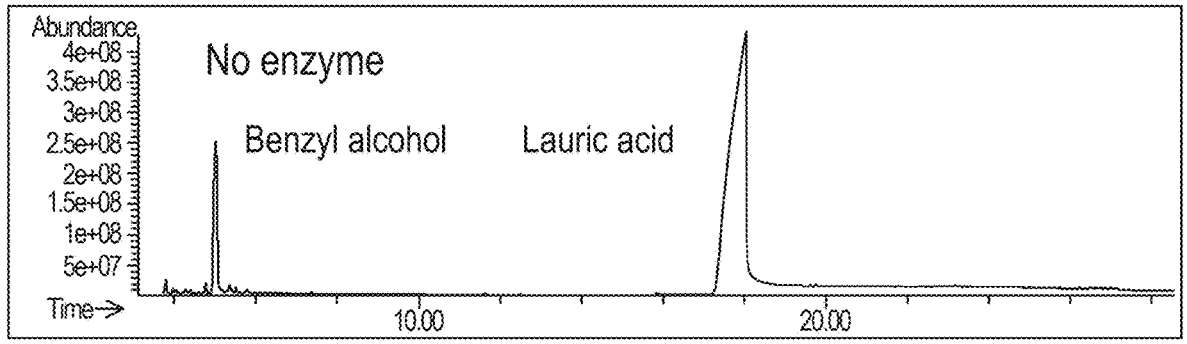
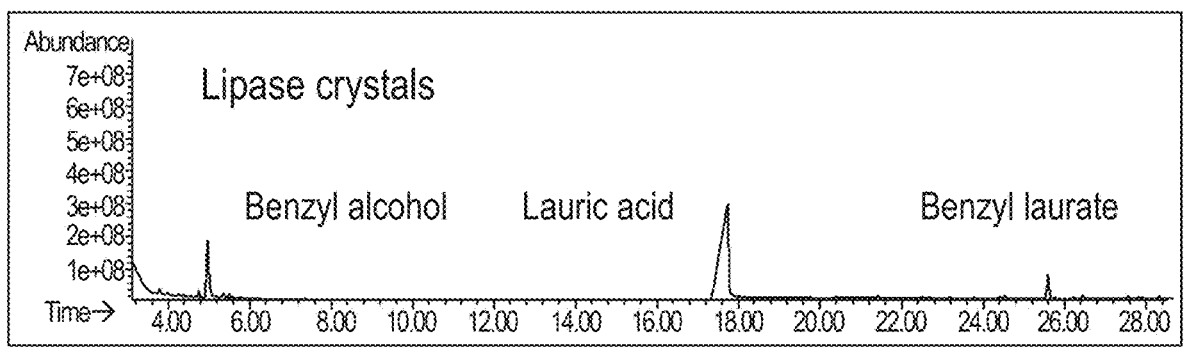
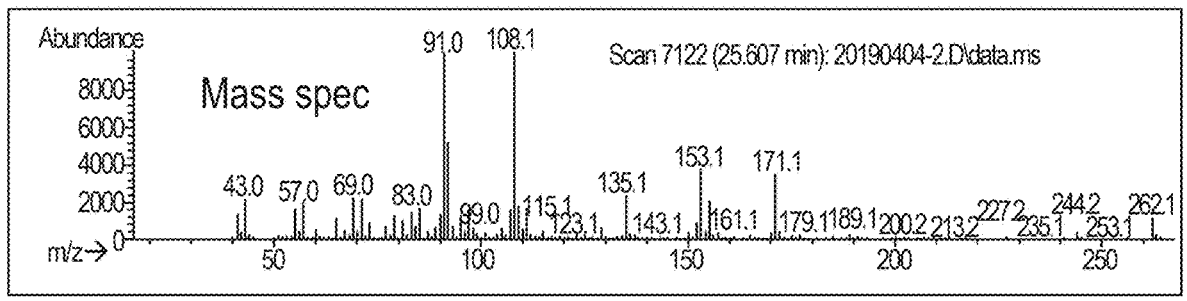

Figure 14
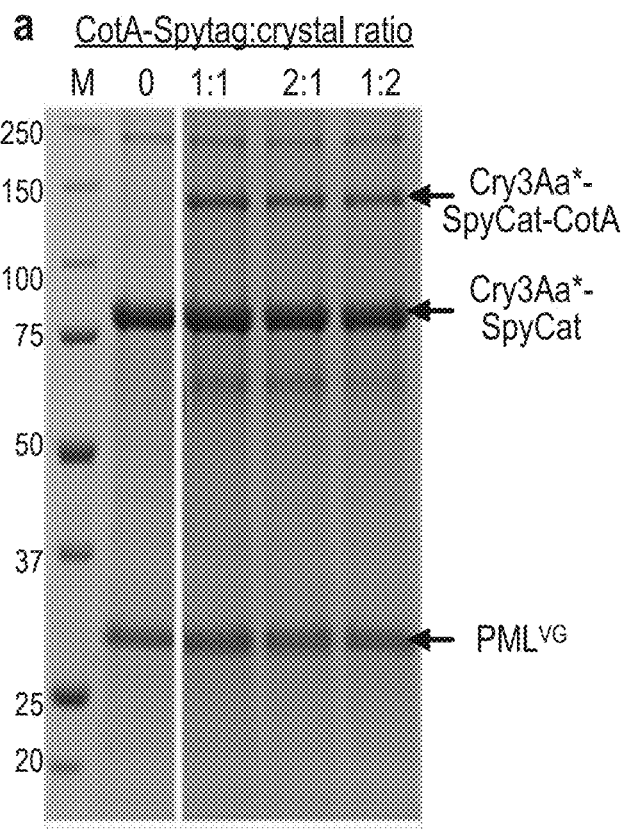
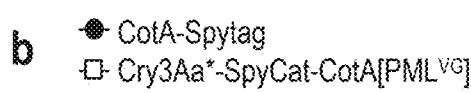
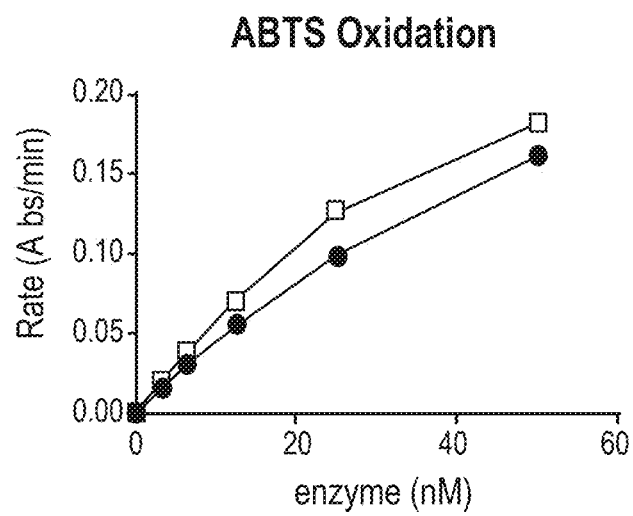

Figure 16A
Scheme 1
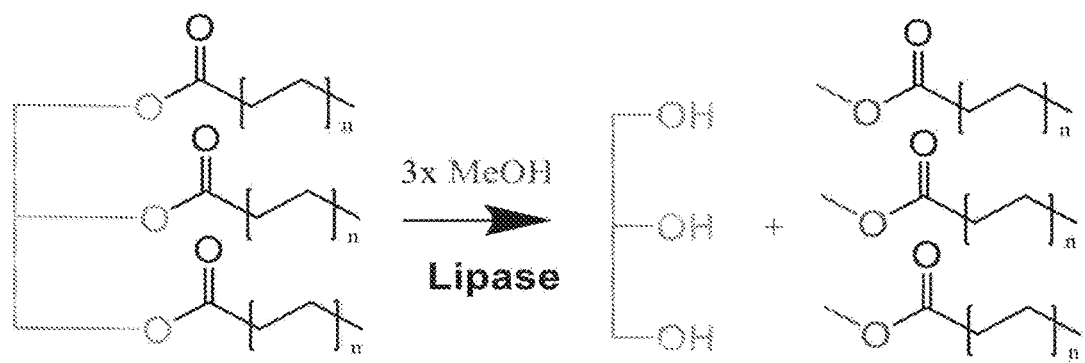
Scheme 2
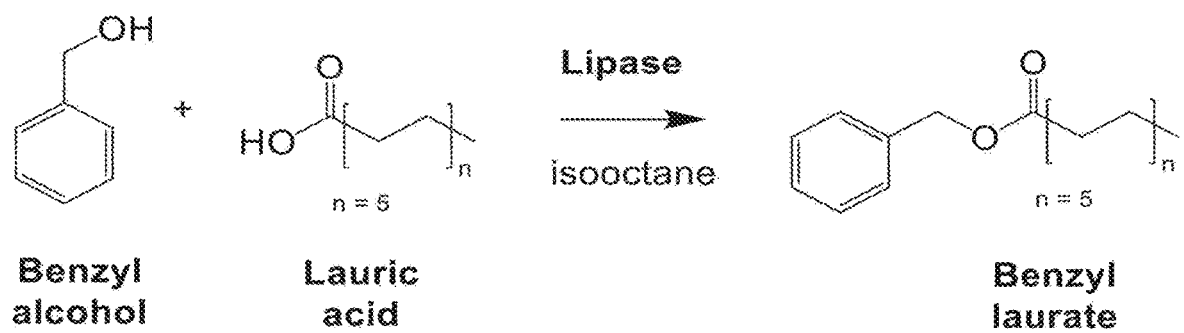

Figure 16B
Scheme 3
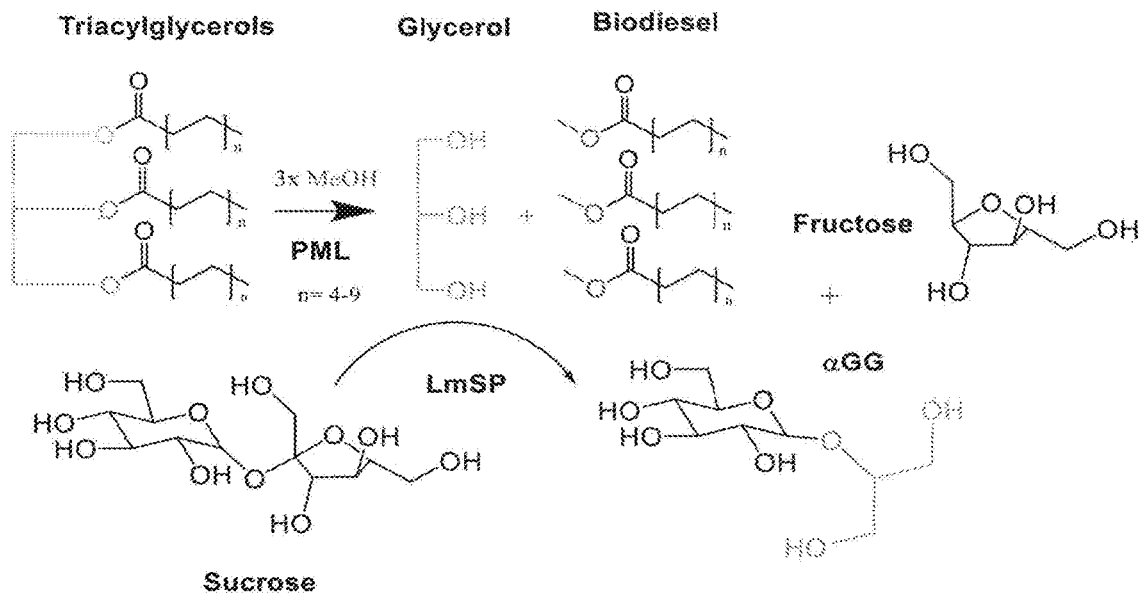
Scheme 4
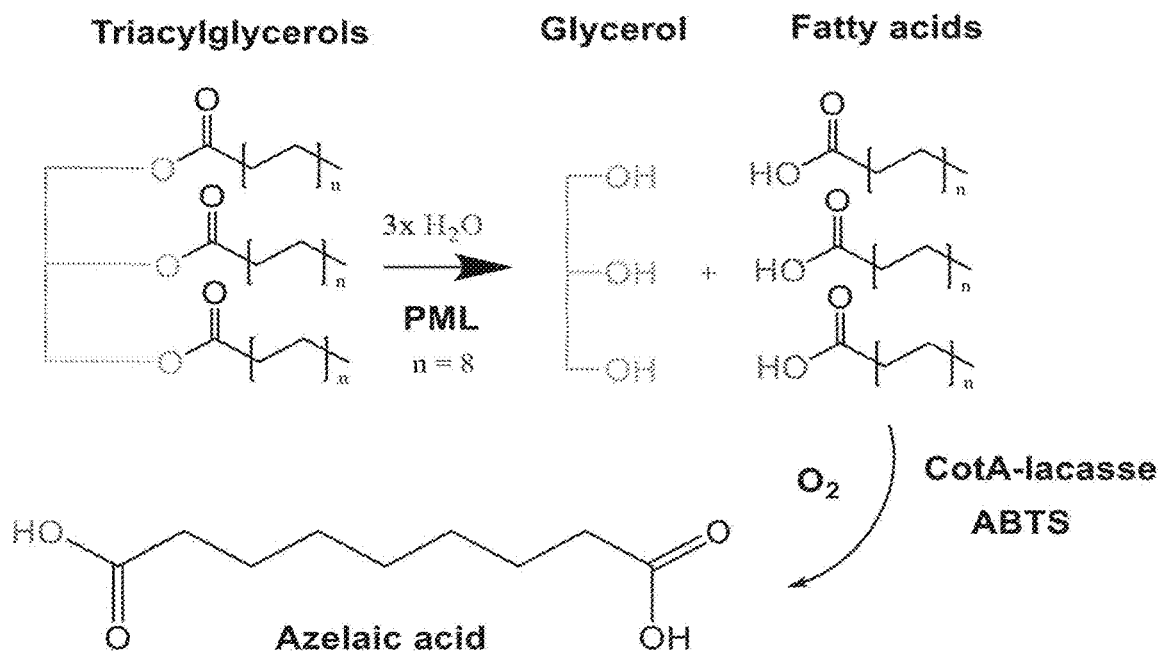

Figure 17

Cry3Aa aligned to negCry3Aa using NCBI protein blast
(Query = Cry3Aa wild-type, SEQ ID NO:3; Subject (Sbjct = negCry3Aa, SEQ ID NO:6)

```
Query    1   MNPNNRSEHDTIKTTENNEVPTNHVQYPLAETPNPTLEDLNYKEFLRMTADNNTEALDSS    60
             MNPNNRSEHDTIKTTENNEVPTNHVQYPLAETPNPTLEDLNYKEFLRMTADNNTEALDSS
Sbjct    1   MNPNNRSEHDTIKTTENNEVPTNHVQYPLAETPNPTLEDLNYKEFLRMTADNNTEALDSS    60

Query   61   TTKDVIQKGISVVGDLLGVVGFPFGGALVSFYTNFLNTIWPSEDPWKAFMEQVEALMDQK   120
             TTKDVIQKGISVVGDLLGVVGFPFGGALVSFYTNFLNTIWPSEDPWKAFMEQVEALMDQK
Sbjct   61   TTKDVIQKGISVVGDLLGVVGFPFGGALVSFYTNFLNTIWPSEDPWKAFMEQVEALMDQK   120

Query  121   IADYAKNKALAELQGLQNNVEDYVSALSSWQKNPVSSRNPHSQGRIPELFSQAESHFRNS   180
             IADYAKNKALAELQGLQNNVEDYVSALSSWQKNPVSSRNPHSQGRIPELFSQAESHFRNS
Sbjct  121   IADYAKNKALAELQGLQNNVEDYVSALSSWQKNPVSSRNPHSQGRIPELFSQAESHFRNS   180

Query  181   MPSFAISGYEVLFLTTYAQAANTHLFLLKDAQIYGEEWGYEKEDIAEFYKRQLKLTQEYT   240
             MPSFAISGYEVLFLTTYAQAANTHLFLLKDAQIYGEEWGYEKEDIAEFYKRQLKLTQEYT
Sbjct  181   MPSFAISGYEVLFLTTYAQAANTHLFLLKDAQIYGEEWGYEKEDIAEFYKRQLKLTQEYT   240

Query  241   DHCVKWYNVGLDKLRGSSYESWVNFNRYRREMTLTVLDLIALFPLYDVRLYPKEVKTELT   300
             DHCVKWYNVGLDKLRGSSYESWVNFNRYRREMTLTVLDLIALFPLYDVRLYPKEVKTELT
Sbjct  241   DHCVKWYNVGLDKLRGSSYESWVNFNRYRREMTLTVLDLIALFPLYDVRLYPKEVKTELT   300

Query  301   RDVLTDPIVGVNNLRGYGTTFSNIENYIRKPHLFDYLHRIQFHTRFQPGYYGNDSFNYWS   360
             RDVLTDPIVGVNNLRGYGTTFSNIENYIRKPHLFDYLHRIQFHTRFQPGYYGNDSFNYWS
Sbjct  301   RDVLTDPIVGVNNLRGYGTTFSNIENYIRKPHLFDYLHRIQFHTRFQPGYYGNDSFNYWS   360

Query  361   GNYVSTRPSIGSNDIITSPFYGNSSEPVQLEFGEKVYRAVANTNLAVWPSAVYSGVT     420
             GNYVSTRPSIGSNDIITSPFYGNSSEPVQLEFGEKVYRAVANTNLAVWPSAVYSGVT
Sbjct  361   GNYVSTRPSIGSNDIITSPFYGNSSEPVQLEFGEKVYRAVANTNLAVWPSAVYSGVT     420

Query  421   KVEFQYNDTDEASTYDSNVGAVSWDSIDQLPPETDEPLEGYSRQLNYVMCFL         480
             KVEFQYNDTDEASTYDSNVGAVSWDSIDQLPPETDEPLEGYSRQLNYVMCFL
Sbjct  421   KVEFQYNDTDEASTYDSNVGAVSWDSIDQLPPETDEPLEGYSRQLNYVMCFL         480

Query  481   MQGSRGTIPVLTWTHKSVDFFNMIDSKKITQLPLVKAYKLQSGASVVAGPRFTGGDIIQC   540
             MQGSRGTIPVLTWTHKSVDFFNMIDSKKITQLPLVKAYKLQSGASVVAGPRFTGGDIIQC
Sbjct  481   MQGSRGTIPVLTWTHKSVDFFNMIDSKKITQLPLVKAYKLQSGASVVAGPRFTGGDIIQC   540

Query  541   TENGSAATIYVTPDVSYSQKYRARIHYASTSQITFTLSLDGAPFNQYYFDKTINKGDTLT   600
             TENGSAATIYVTPDVSYSQKYRARIHYASTSQITFTLSLDGAPFNQYYFDKTINKGDTLT
Sbjct  541   TENGSAATIYVTPDVSYSQKYRARIHYASTSQITFTLSLDGAPFNQYYFDKTINKGDTLT   600

Query  601   YNSFNLASFSTPFELSGNNLQIGVTGLSAGDKVYIDKIEFIPVN   644
             YNSFNLASFSTPFELSGNNLQIGVTGLSAGDKVYIDKIEFIPVN
Sbjct  601   YNSFNLASFSTPFELSGNNLQIGVTGLSAGDKVYIDKIEFIPVN   644
```

Figure 18
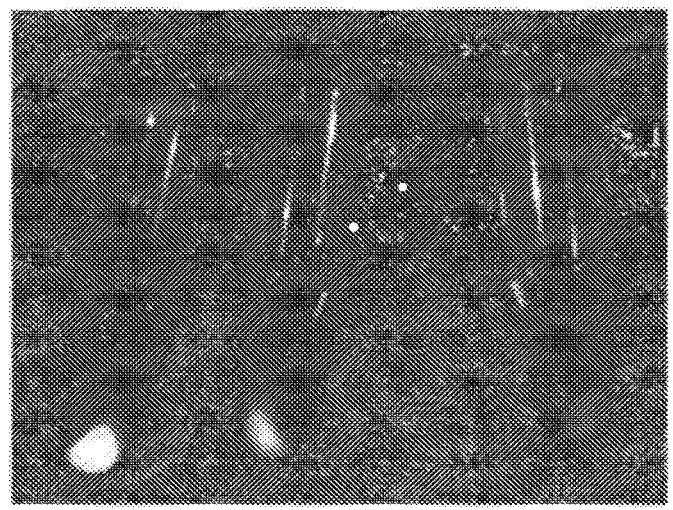
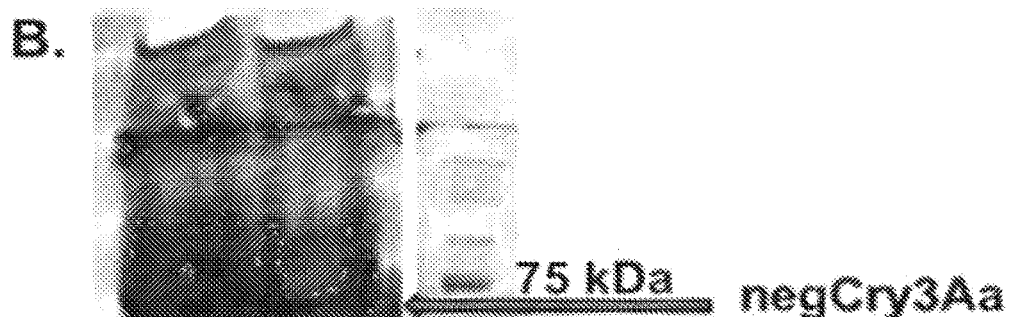

Figure 22

```
  1 MNPNNRSEHD TIKTTENNEV PTNHVQYPLA ETPNPTLEEL NYKEFLRMTA DNNTEALDSS
 61 TTKDVIQKGI SVVGDLLGVV GFPFGGALVS FYTNFLNTIW PSEDPWKAFM EQVEALMDQK
121 IADYAKNKAL AELQGLQNNV EDYVSALSSW QKNPVSSRNP HSQGRIRELF SQAESHFRNS
181 MPSFAISGYE VLFLTTYAQA ANTHLFLLKD AQIYGEEWGY EKEDIAEFYK RQLKLTQEYT
241 DHCVKWYNVG LDKLRGSSYE SWVNFNRYPR EMTLTVLDLI ALFPLYDVRL YPKEVKTELT
301 RDVLTDPIVG VNNLRGYGTT FSNIENYIRK PHLFDYLHRI QFHTPFQPGY YGNDSFNYWS
361 GNYVSTRPSI GSNDIITSFF YGNKSSEPVQ NLEFNGEKVY RAVANTNLAV WPSAVYSGVT
421 KVEFSQYNDQ TDEASTQTYD SKRNVGAVSW DSIDQLPPET TDEPLEKGYS HQLNYVMCFL
481 MQGSRGTIPV LTWTHKSVDF FNMIDSKKIT QLPLVKAYKL QSGASVVAGP RFTGGDIIQC
541 TENGSAATIY VTPDVSYSQK YRAKIHYAST SQITFTLSLD GAPFNQYYFD KTINKGDTLT
601 YNSFNLASFS TPFELSGNNL QIGVTGLSAG DKVYIDKIEF IPVN
```

Figure 23

| Region | Amino Acid Residues |
|---|---|
| 110-128 | M110 E111 Q112 V113 E114 A115 L116 M117 D118 Q119 K120 I121 A122 D123 Y124 A125 K126 N127 K128 |
| 181-197 | M181 P182 S183 F184 A185 I186 S187 G188 Y189 E190 V191 L192 F193 L194 T195 T196 Y197 |
| 211-226 | A211 Q212 I213 Y214 G215 E216 E217 W218 G219 Y220 E221 K222 E223 D224 I225 A226 |
| 250-264 | G250 L251 D252 K253 L254 R255 G256 S257 S258 Y259 E260 S261 W262 V263 N264 |
| 423-436 | E423 F424 S425 Q426 Y427 N428 D429 Q530 T431 D432 E433 A434 S435 T436 |
| 457-471 | P457 P458 E459 T460 T461 D462 E463 P464 L465 E466 K467 G468 Y469 S470 H471 |
| 593-598 | I593 N594 K595 G596 D597 T598 |
| 627-632 | L627 S628 A629 G630 D631 K632 |

IN VIVO IMMOBILIZATION OF PROTEINS

RELATED APPLICATIONS

This application is a 371 National Stage Entry of PCT Patent Application No. PCT/CN2020/086652, filed Apr. 24, 2020, which claims priority to U.S. Provisional Patent Application No. 62/839,400, filed Apr. 26, 2019, the contents of which are hereby incorporated by reference in the entirety for all purposes.

REFERENCE TO SUBMISSION OF A SEQUENCE LISTING AS A TEXT FILE

The Sequence Listing written in file 080015-1258878-027710US_SL.txt created on Sep. 20, 2022, 111,479 bytes, machine format IBM-PC, MS-Windows operating system, is hereby incorporated by reference in its entirety for all purposes.

BACKGROUND OF THE INVENTION

In many medical and industrial contexts the use of recombinant proteins is becoming increasingly more important. The production, isolation, use, and potential reuse of recombinant proteins, especially enzymes, remain in need of improvement for better quality, efficiency, and stability. For instance, enzyme immobilization can facilitate easy removal and subsequent reuse of enzymes during multiple rounds of catalysis. In many cases, immobilization also improves the stability of enzymes against many industrial conditions such as high temperatures and organic solvents. Immobilization by entrapment is particularly attractive since it does not involve any modifications to the enzyme structure, increasing the chance for high activity retention and native enzyme conformation. Thus, there exists a need for new and effective means for producing recombinant proteins, such as enzymes, in immobilized form. The present invention fulfills this and other related needs.

BRIEF SUMMARY OF THE INVENTION

This invention provides a novel approach to improve the physical properties and stability of recombinant proteins by immobilizing recombinant proteins such as enzymes useful in various industrial applications. Thus, in a first aspect, this invention provides a method for recombinantly co-expressing a protein of interest with a crystal-forming protein. The method includes these steps: (1) providing bacterial cells comprising an expression cassette encoding the protein of interest and an expression cassette encoding a Cry protein, a crystal-forming fragment of the Cry protein, or a fusion protein capable of forming crystals comprising the Cry protein or the crystal-forming fragment thereof, and (2) culturing the bacterial cells under conditions permissible for the expression of the protein of interest as well as the Cry protein, the crystal-forming fragment thereof, or the fusion protein, wherein the Cry protein, the crystal-forming fragment thereof, or the fusion protein forms crystal containing the protein of interest upon both being expressed in the bacterial cells.

In some embodiments, the protein of interest is an enzyme, such as a lipase (e.g., *Proteus mirabilis* lipase, or PML, including a PML variant with modifications of residues 118 and 130, for example, I118V+E130G, and lipA or lipAR9), ligase, hydrolase, esterase, protease, or glycosidase. In some embodiments, the Cry protein is Cry3Aa. In some embodiments, the crystal-forming fragment is the N-terminal 290 amino acids of Cry3Aa, or the N-terminal 625 or 626 amino acids of Cry3Aa, or the 498-644 fragment of Cry3Aa. In some embodiments, the expression cassette encoding the protein of interest and the expression cassette encoding the Cry protein, crystal-forming fragment thereof, or the fusion protein is one and the same expression cassette. In some embodiments, the one single expression cassette comprises (1) one copy of polynucleotide sequence encoding the Cry protein, crystal-forming fragment thereof, or the fusion protein, and (2) one copy or two or more copies of polynucleotide sequence encoding the protein of interest. In some embodiments, (1) the polynucleotide sequence encoding the Cry protein, crystal-forming fragment thereof, or the fusion protein, and (2) the polynucleotide sequence encoding the protein of interest are operably linked to one single promoter. In some embodiments, the one single promoter is operably linked to (1) one copy of the polynucleotide sequence encoding the Cry protein, crystal-forming fragment thereof, or the fusion protein, followed by (2) one copy of the polynucleotide sequence encoding the protein of interest, with one ribosome binding site between (1) and (2). In some embodiments, the one single promoter is operably linked to (1) one copy of the polynucleotide sequence encoding the Cry protein, crystal-forming fragment thereof, or the fusion protein, followed by (2) two or more copies of the polynucleotide sequence encoding the protein of interest, with one ribosome binding site between (1) and (2) and between two copies of polynucleotide sequence encoding the protein of interest.

In some embodiments, (1) the polynucleotide sequence encoding the Cry protein, crystal-forming fragment thereof, or the fusion protein; and (2) the polynucleotide sequence encoding the protein of interest are operably linked to two separate promoters. In some embodiments, the two separate promoters are two different kinds of promoters, for example, cyt1Aa promoter and cry3Aa promoter. In some embodiments, (1) the polynucleotide sequence encoding the Cry protein, crystal-forming fragment thereof, or the fusion protein; and (2) the polynucleotide sequence encoding the protein of interest share one single termination codon, resulting in one copy of the Cry protein, crystal-forming fragment thereof, or the fusion protein and two copies of the protein of interest.

In some embodiments, the expression cassette encoding the protein of interest and the expression cassette encoding the Cry protein, crystal-forming fragment thereof, or the fusion protein are two separate expression cassettes. In some embodiments, the fusion protein comprises the Cry protein or crystal-forming fragment thereof and one or more heterologous polypeptides (such as a lipase lipA or SEQ ID NO:8 in 1-3 repeats) at the N- and/or C-terminus. In some embodiments, the fusion protein is Cry3Aa-[SmtA]$_{1-3}$. In some embodiments, two or more proteins of interest are co-expressed with the Cry protein, the crystal-forming fragment thereof, or the fusion protein and are contained within the crystal formed by the Cry protein, the crystal-forming fragment thereof, or the fusion protein. In some embodiments, the bacterial cells are *Bacillus subtilis* (Bs) or *Bacillus thuringiensis* (Bt) cell or *E. coli* cells. In some embodiments, the method of this invention further includes a step, prior to step (1), of introducing into the bacterial cells the expression cassette encoding the protein of interest and the expression cassette encoding the Cry protein, crystal-forming fragment thereof, or the fusion protein. In some embodiments, more than one protein of interest, e.g., two or more proteins, are recombinantly co-expressed with the Cry protein, crystal-forming fragment thereof, or the fusion protein. These proteins of interest may be the same protein (e.g., both are PML) or different proteins (e.g., one lipase and one ligase). In some embodiments, the method of this invention further includes a step, after step (2), of isolating the crystal formed by the Cry protein, the crystal-forming fragment thereof, or the fusion protein and entrapping the protein or proteins of interest, which may be more than one protein, e.g., two or more proteins. In some embodiments, after it is isolated, the crystal containing the protein(s) of interest is washed under appropriate conditions such as choosing appropriate salt concentration etc. to permit the protein(s) entrapped within the crystal to be released from the crystal, preferably without dissolving the crystal to any substantial degree. In some embodiments, after being isolated, the crystal containing the protein(s) of interest is dissolved to release the protein(s) entrapped within the crystal. In some embodiments, the protein is an enzyme, such as PML. In some embodiments, the protein of interest is a fluorescent protein such as mCherry.

In a second aspect, the present invention provides a protein crystal produced by the method described above and herein for co-expression of one or more recombinant proteins of interest with a crystal-forming protein, such as a Cry protein, a crystal-forming fragment of the Cry protein, or a fusion protein capable of forming crystals comprising the Cry protein or the crystal-forming fragment thereof. In some embodiments, the protein of interest is an enzyme, such as a lipase (e.g., *Proteus mirabilis* lipase, or PML, including a PML variant with modifications of residues 118 and 130, for example, I118V+E130G, and lipA or lipAR9), ligase, hydrolase, esterase, protease, or glycosidase. In some embodiments, the protein of interest is a fluorescent protein such as mCherry.

In a third aspect, the present invention provides a method for performing a reaction. The method comprises the step of incubating the protein crystal produced by the method of this invention entrapping an enzyme therein with a substrate to the enzyme under conditions permissible for the substrate to be catalyzed by the enzyme. In some embodiments, the enzyme is a lipase (e.g., *Proteus mirabilis* lipase, or PML, including a PML variant with modifications of residues 118 and 130, for example, I118V+E130G, and lipA or lipAR9), ligase, hydrolase, esterase, protease, or glycosidase. In some embodiments, the method further comprises a step, after the reaction is completed, of removing the reaction product and cleaning, e.g., washing the crystal to remove any detectable amount of reaction mixture including reaction agents and/or product(s), preferably without dissolving the crystal to any substantial degree, and then reusing the protein crystal in a second reaction.

In a fourth aspect, the present invention provides an in vitro method for co-crystallizing (1) a Cry protein, a crystal-forming fragment of the Cry protein, or a fusion protein capable of forming crystals comprising the Cry protein or the crystal-forming fragment thereof with (2) one or more proteins (e.g., enzymes) by mixing a soluble protein described in (1) with the protein or proteins of (2), thus allowing the protein or protein(s) of (2) to be entrapped within a protein crystal formed by the crystal-forming protein of (1). In some embodiments, the protein is an enzyme. In some embodiments, the enzyme-entrapped protein crystal so formed is used for performing a reaction where the protein crystal is incubated with a substrate to the enzyme under conditions permissible for the substrate to be catalyzed by the enzyme. In some embodiments, the protein crystal containing entrapped protein(s) of interest formed by the methods described above and herein is used for delivering the protein(s) to cells, such as macrophages, lymphocytes, cancer cells, red blood cells, epithelial cells, stem cells, and liver cells.

In a fifth aspect, the present invention provides various modified Cry proteins, their fragments or fusion proteins, all of which still retaining the crystalizing capability (for example, Cry3Aa*, Cry3Aa*-lipA, Cry3Aa*-SpyCat, Cry3Aa-[SmtA]$_{1-3}$, NegCry3Aa, 3A2-2, Cry3Aa (S145C, H161R), as well as various modified proteins with retained enzymatic activities (such as PML, PML$^{VG}$, LmSP, LipA, and LipAR9), a polynucleotide sequence encoding each of such proteins, a nucleic acid comprising the polynucleotide sequence encoding each of the proteins, especially an expression cassette comprising the polynucleotide coding sequence operably linked to a promoter (e.g., a heterologous promoter from an origin different from that of the wild-type base protein) or a vector comprising such an expression cassette, a host cell comprising such a vector or expression cassette, which is able to express the protein under permissible culture conditions. Also provided are methods for recombinantly producing any of these proteins by culturing the host cells under conditions permissible for the recombinant protein expression and optionally further concentrating or isolating/purifying the proteins.

BRIEF DESCRIPTION OF THE DRAWINGS

FIG. 4. Plasmid variations constructed for optimization of PML entrapment in Cry3Aa crystals. 3P-cry3Aa promoter; RBS-ribosome binding site.

FIG. 8A. Recyclability of optimized Cry3Aa[PML$^{VG}$] crystals during the conversion of waste cooking oil to biodiesel. Cycles were 10 h each. FIG. 8B. Thermal stability of free PML$^{VG}$ and 3P3A[3PPML$^{VG}$] crystals. Samples were incubated in triplicate at various temperatures for 1 h and then tested for residual activity. Error bars show the standard deviation of the mean.

FIG. 9. GCMS analysis of benzyl laurate synthesis reaction. (a) Elution profile of no enzyme control shows no benzyl laurate peak. (b) Elution profile of lipase crystals reaction to produce benzyl laurate. (c) Mass-spec of benzyl laurate peak confirms product formation.

FIG. 14. Production and activity of the lipase:lacasse catalyst. (a) SDS-PAGE gel showing conjugation of CotA-Spytag to Cry3Aa*-SpyCat[PML$^{VG}$] crystals at different ratios. Lane (M) molecular weight marker (kDa). (b) 2,2'-azino-bis(3-ethylbenzothiazoline-6-sulphonic acid) (ABTS) oxidation by free CotA-Spytag and Cry3Aa*-SpyCat [PML$^{VG}$] crystals.

FIG. 16A. Scheme 1: Lipase catalyzed tranesterification of triacylglycerols with methanol (MeOH) to produce biodiesel. Scheme 2: Lipase catalyzed esterification of benzyl alcohol and lauric acid in neat isooctane to produce the cosmetic compound benzyl laurate.

FIG. 16B. Scheme 3: Reaction scheme for the one-pot synthesis of biodiesel and αGG using PML lipase and LmSP sucrose phosphorylase. Scheme 4: Reactions scheme for one-pot production of azelaic acid using PML lipase and CotA-lacasse.

FIG. 17. Amino acid sequence alignment between Cry3Aa (SEQ ID NO:4) and NegCry3Aa (SEQ ID NO:6).

FIG. 18. Purified negCry3Aa-RBS-scGFP protein crystals. (A) NegCry3Aa-RBS-scGFP crystal pellets purified from Bt cells grown for 48 h (left) and 72 h (right) were imaged using BioRad ChemiDoc MP System at the GFP excitation wavelength (ex=488 nm). (B) SDS-PAGE gel showing the corresponding purified NegCry3Aa-RBS-scGFP crystals in (A).

FIG. 22 Cry3Aa protein sequence. Residues in bold are regions exposed to the solvent channel and can be deleted to expand the channel size. (SEQ ID NO: 4).

FIG. 23. Amino acids in specific regions exposed to the Cry3Aa (SEQ ID NO:4) crystal channel.

DEFINITIONS

Figure 1:
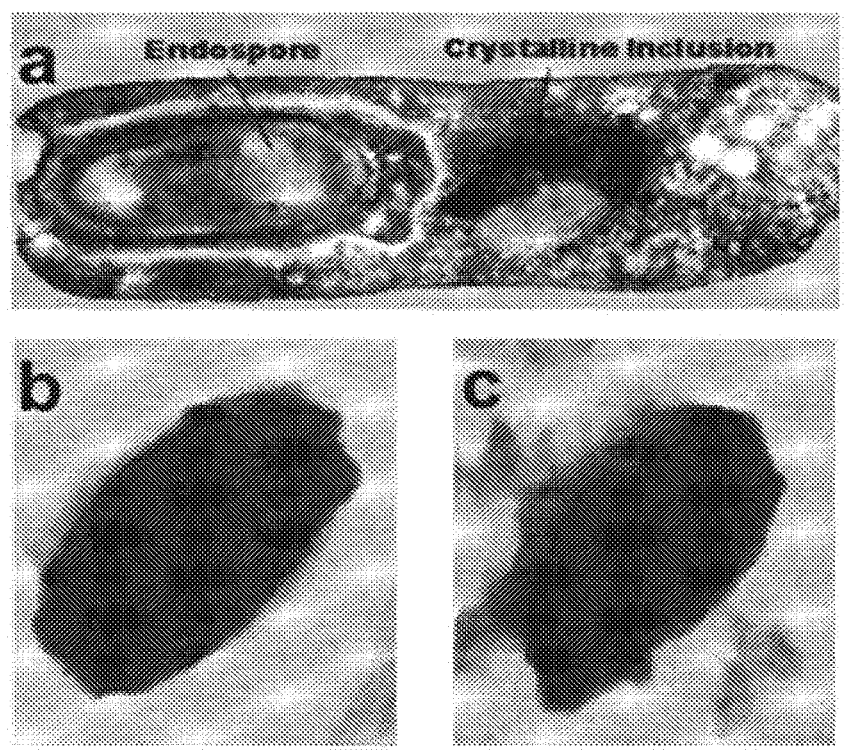
FIG. 1. (a) Electron micrograph of Bt. highlighting its crystal inclusion. Electron micrographs of purified (b) Cry3Aa crystals, and (c) Cry3Aa-GFP fusion crystals (reproduced from reference 15).
Figure 2:
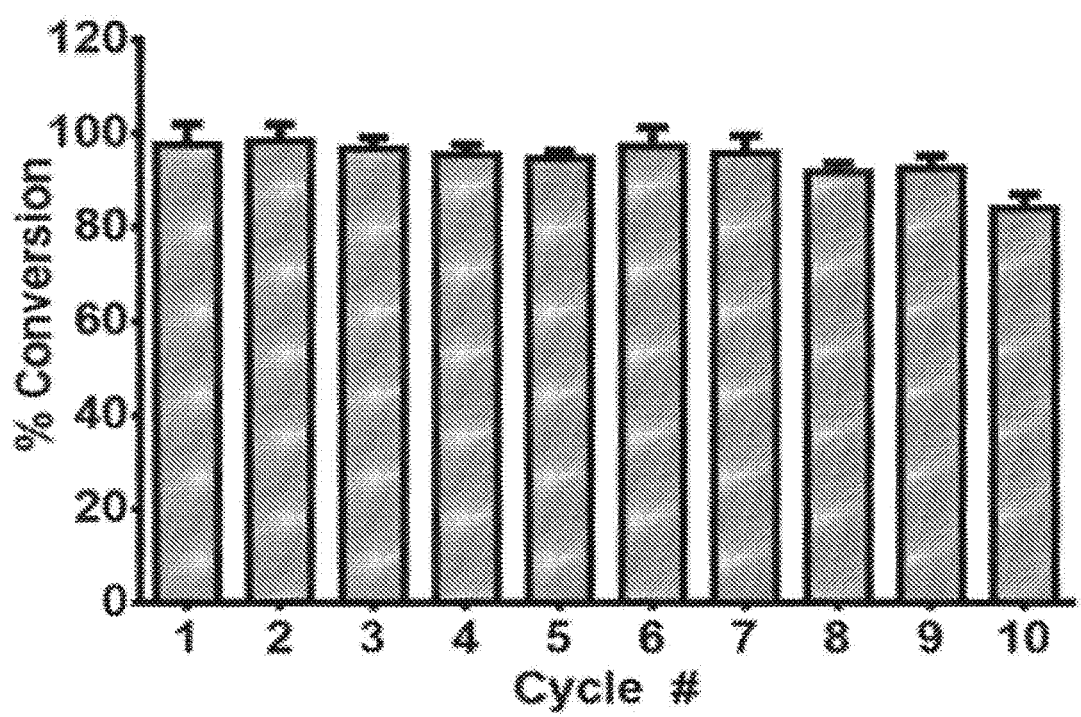
FIG. 2. Recyclability of Cry3Aa*-lipA for the conversion of coconut oil to biodiesel.[16]

The term "Cry protein," as used herein, refers to any one protein among a class of crystalline proteins produced by strains of *Bacillus thuringiensis* (Bt). Some examples of "Cry proteins" include, but are not limited to, Cry1Aa, Cry1Ab Cry2Aa, Cry3Aa, Cry4Aa, Cry4Ba, Cry11Aa, Cry11Ba, and Cry19Aa. Their amino acid sequences and polynucleotide coding sequences are known and can be found in publications such as U.S. Patent Application published as US2010/0322977. Their GenBank Accession Nos are:

Cry1Aa AY197341.1
Cry1Ab AY847289.1
Cry2Aa AF273218.1
Cry3Aa AJ237900.1
Cry4Aa AB513706.1
Cry4Ba AB161456.1
Cry11Aa AL731825.1
Cry11Ba LC153032.1
Cry19Aa Y07603.1

In addition to the wild-type Cry proteins, the term "Cry protein" also encompasses functional variants, which (1) share an amino acid sequence identity of at least 80%, 81%, 82%, 83%, 84%, 88%, 89%, 90%, 91%, 92%, 93%, 94%, 95%, 96%, 97%, 98%, 99%, or 99.5% to the polypeptide sequence of any one of the Cry proteins listed in US2010/0322977; and (2) retain the ability to spontaneously form crystals within host cells as can be confirmed by known methods such as electron micrograph (see description in, e.g., Park et al., *Appl Environ Microbiol*, 1998, 64, 3932-3938; Schnepf et al., *Microbiol Mol Biol Rev*, 1998, 62, 775-806; Whiteley and Schnepf, *Annu Rev Microbiol*, 1986, 40, 549-576; and Nair et al., *PLoS One*, 2015, 10, e0127669). For example, a "Cry protein" encompasses any variant that confers increased negative charges to the resultant protein by substitutions of at least 3, 4, 5, 6, 7, 8, 9, 10, 11, 12, 13, 14, 15, or more positively charged or neutral amino acids within the domain II of the wild-type Cry protein (e.g., the 295 to 499 segment of SEQ ID NO:4, as well as its corresponding segment in other Cry proteins as shown in FIG. 27) with negatively charged amino acids such as aspartate (D) and glutamate (E). One example of such mutant is NegCry3Aa, SEQ ID NO:6, which is a Cry3Aa variant containing the following mutations: K384E, N391D, N395D, S425E, Q430E, TQ436437EE, KR442443EE, T461D, and K467E. Further encompassed by the term "Cry protein" are modified Cry proteins containing amino acid insertions or deletions (for example, insertion of at least 1, 2, 3, 4, 5, 6, 7, 8, 9, or 10 amino acids, or a deletion of at least 1, 2, 3, 4, 5, 6, 7, 8, 9, 10, or more amino acids) at one or more of the 8 specific regions (for example, at least 1, 2, 3, 4, 5, 6, 7, or all 8 regions) shown in FIG. 22, as well as their corresponding regions in other Cry proteins as shown in FIG. 18 of PCT/CN2020/084939, can effectively reduce or enlarge the protein's channel size, respectively, and can therefore make the resultant crystal-forming protein variant to more effectively entrap a target protein (such as an enzyme) with increased retention rate and reduced diffusion rate for the target protein. Typically, such a channel-size altering Cry protein mutant contains at least 3, 4, or 5 but no more than 10, 12, or 15 point mutations (deletions or insertions) in the entire protein. One example of a Cry3Aa mutant of this nature is termed 3A2-2 (SEQ ID NO:7). In addition, the term "Cry protein" also encompasses Cry protein mutants that have been modified at one or more residues to improve the stability of the resultant protein or its crystal structure, for example, introducing one or more cysteine residues by insertion or substitution to the wild-type Cry protein amino acid sequence so as to form additional disulfide bond or bonds to stabilize the protein or crystal structure. One such example is a double mutant of Cry3Aa (3AS145C, H161R), having the amino acid sequence of SEQ ID NO:9.

Similarly, a "crystal-forming fragment" of a Cry protein is a fragment of any of the known Cry proteins (i.e., less than full length of the wild-type Cry protein) that still retains the ability of self-crystallization, which is demonstrated both by crystallization by the fragment alone and by causing a fusion protein to self-crystallize when the fragment is present in the fusion protein with another protein of interest (e.g., an enzyme). In addition to being a truncated form of a Cry protein, a "crystal-forming fragment" may further contain one or more modifications to the native amino acid sequence such as insertions, deletions, or substitutions, especially conservative modifications, such that the resultant "crystal-forming fragment" shares an amino acid sequence identity of at least 80%, 81%, 82%, 83%, 84%, 88%, 89%, 90%, 91%, 92%, 93%, 94%, 95%, 96%, 97%, 98%, 99%, or 99.5% to the polypeptide sequence of the corresponding fragment of a wild-type Cry protein. Exemplary crystal-forming fragments of a Cry protein have been described in earlier disclosures, e.g., WO2018/028371.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a Cry protein or a crystal-forming fragment of a Cry protein sequence comprised in the fusion protein of this invention has at least 80% identity, preferably 85%, 90%, 91%, 92%, 93, 94%, 95%, 96%, 97%, 98%, 99%, or 100% identity, to a reference sequence, e.g., the amino acid sequence of a corresponding wild-type Cry protein or fragment), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection, see, e.g., *Current Protocols in Molecular Biology* (Ausubel et al., eds. 1995 supplement).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "recombinant" when used with reference, e.g., to a cell, or a nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral vector derived from a viral genome, or nucleic acid fragment/construct. Typically, an expression cassette includes a polynucleotide to be transcribed, operably linked to a promoter. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

A "promoter" is defined as an array of nucleic acid control sequences that direct transcription of a polynucleotide sequence. As used herein, a promoter includes necessary polynucleotide sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a polynucleotide expression control sequence (such as a promoter, or array of transcription factor binding sites) and a second polynucleotide sequence, wherein the expression control sequence directs transcription of the polynucleotide sequence corresponding to the second sequence.

The term "heterologous" as used in the context of describing the relative location of two elements, refers to the two elements such as polynucleotide sequences (e.g., a promoter or a protein/polypeptide-encoding sequence) or polypeptide sequences (e.g., a Cry protein sequence or another polypeptide sequence) that are not naturally found in the same relative positions. Thus, a "heterologous promoter" of a gene refers to a promoter that is not naturally operably linked to that gene. Similarly, a "heterologous polypeptide" or "heterologous polynucleotide" to a Cry protein or its encoding sequence or a fragment thereof is one derived from an origin other than the Cry protein or, in the case of a fragment of a Cry protein/coding sequence, may be derived from another part of the same Cry protein or coding sequence, but not naturally connected to the fragment in the same fashion. The fusion of a fragment of a Cry protein (or its coding sequence) with a heterologous polypeptide (or polynucleotide sequence) does not result in a longer polypeptide or polynucleotide sequence that can be found naturally in the wild-type Cry protein.

By "host cell" is meant a cell that contains an expression vector and supports the replication or expression of one or more coding sequences harbored in the expression vector. Host cells may be prokaryotic cells such as *Bacillus thuringiensis* (Bt), *Bacillus subtilis* (Bs), or *E. coli*, or eukaryotic cells such as yeast, insect, amphibian, or mammalian cells such as CHO, HeLa and the like, e.g., cultured cells, explants, and cells in vivo.

The term "about" as used herein denotes a range of +/−10% of a reference value. For examples, "about 10" defines a range of 9 to 11.

DETAILED DESCRIPTION OF THE INVENTION

I. Introduction

There has been growing interest in using enzymes to catalyze industrial reactions due to their high reactivity, excellent regio- and enantiospecificity, and low environmental toxicity. In order to financially compete with chemical catalysis, biocatalysts are optimized so they can be recycled multiple times. Additionally, biocatalysts are generally optimized so they can withstand high concentrations of organic solvents—conditions that can promote substrate solubility and enzyme activity. Enzyme immobilization can facilitate easy removal and subsequent reuse of enzymes during multiple rounds of catalysis, in addition to improving enzyme stability resistant to harsh industrial conditions. Immobilization by entrapment is particularly attractive since it does not involve any modifications to the enzyme structure, increasing the chance for high activity retention and native enzyme conformation. In this disclosure, a novel one-step method is described for producing entrapped recombinant proteins (especially enzymes, including multi-enzymes) in protein crystals.

To date, all entrapment methods involve first producing the enzyme and carrier separately, and then mixing them to generate the immobilized enzyme. This multi-step process requires purifying and concentrating the enzyme, synthesizing the carrier, and then mixing them, usually including the use of a catalyst to initiate the polymerization of the carrier. This procedure is tedious and expensive. A method that generates an entrapped enzyme or multi-enzyme system in one-step process can significantly reduce production costs and lead to cheaper commercial catalysts. The method of this invention leads to the entrapped enzyme in one step, avoiding the need for purification of the free enzyme or polymerization of the carrier. Minimizing time, processes, and materials for producing enzyme catalysts allows for greener and more cost-effective products.

II. Production of Recombinant Proteins

A. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J Chrom.* 255: 137-149 (1983).

The sequence of a gene of interest, such as the polynucleotide sequence encoding an enzyme like lipase or hydrolase, a polynucleotide encoding a Cry protein or a crystal-forming fragment thereof, and synthetic oligonucleotides can be verified after cloning or subcloning using, e.g., the chain termination method for sequencing double-stranded templates of Wallace et al., Gene 16: 21-26 (1981).

B. Coding Sequences

Polynucleotide sequences encoding Cry proteins, fragments, or fusion proteins for use in this invention can be readily constructed by using the corresponding coding sequences for the Cry proteins, fragments, or combining the coding sequences for the fusion partners, such as a Cry3Aa protein and *Bacillus subtilis* lipase A (lipA). The sequences for Cry proteins and enzymes are generally known and may be obtained from a commercial supplier.

In addition to the use of full length wild-type Cry proteins for producing crystal-forming proteins for use in this invention, fragments of Cry proteins and/or variants of Cry proteins may also be useful. A DNA sequence encoding a Cry protein can be modified to generate fragments or variants of the Cry protein. So long as the fragments and variants retain the ability to spontaneously form crystals when expressed in a host cell, especially a *Bacillus* bacterial cell, they can be used for producing the protein crystals, either by themselves or by way of fusion proteins capable of undergoing spontaneous crystallization, and therefore producing protein crystals containing one or more recombinant proteins (e.g., one or more enzymes) embedded within. Typically, the variants bear a high percentage of sequence identity (e.g., at least 80, 85, 90, 95, 97, 98, 99% or higher) to the wild-type Cry protein sequence, whereas the fragments may be substantially shorter than the full length Cry protein, such as having some amino acids (e.g., 10-300 or 20-200 or 50-100 amino acids) removed from the N- or C-terminus of the full length Cry protein. For example, a useful Cry3Aa fragment may be as short as the first 290 amino acids from the N-terminus, encompassing Domain I of the protein. Other examples of such fragments include a Cry protein fragment having its first 57 amino acids from N-terminus removed and a Cry protein fragment having its C-terminal 18 amino acids removed. The ability of a recombinantly produced Cry protein, a fragment thereof, or a fusion protein comprising a Cry protein or fragment to undergo spontaneous crystallization can be verified by electron micrograph, whereas the enzymatic activity of a recombinantly produced enzyme, including in the form of a fusion protein with a Cry protein or a fragment thereof, can be confirmed by established assays for each specific enzyme. Exemplary Cry protein fragments capable of self-crystallizing can be found in the inventors' earlier publications, e.g., WO2018/028371.

In the case of a fusion protein, a peptide linker or spacer is used between the coding sequences for a Cry protein/fragment and one or more heterologous polypeptides. One purpose is to ensure the proper reading frame for the fusion protein such that the coding sequences for both Cry protein/fragment and the heterologous polypeptide(s) are in frame. Another purpose is to provide appropriate spatial relationship between the Cry protein/fragment and the heterologous polypeptide(s), such that each component of the fusion protein may retain its original functionality: the Cry protein/fragment is able to cause self-crystallization of the fusion protein, and the heterologous polypeptide such as an enzyme remains active in its catalytic capacity. Also, one or more linkers may be placed at the very beginning and/or the very end of the open reading frame, so as to facilitate proper start and termination of the coding sequence translation. Such linkage amino acid sequences are usually shorts and typically no longer than 100 or 50 amino acids, such as between 1 to 100, 1 or 2 to 50, 2 or 3 to 25, 3 or 4 to 10 amino acids.

C. Sequence Modification for Preferred Codon Usage in a Host Organism

The polynucleotide sequence encoding a recombinant protein to be expressed according to the method of this invention can be further altered to coincide with the preferred codon usage of a particular host. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of a protein (e.g., an enzyme such as a lipase) along with a Cry protein, a crystal-forming fragment of the Cry protein, or a fusion protein comprising the Cry protein or crystal-forming fragment, such that the protein (e.g., enzyme) is produced and embedded in the protein crystals formed by the Cry protein, fragment, or fusion protein.

III. Expression and Isolation of Proteins Embedded in Protein Crystals

Following verification of the coding sequence, co-expression of a protein of interest (such as an enzyme) and a Cry protein, a crystal-forming fragment thereof, or a fusion protein comprising the Cry protein or fragment of this invention can be produced using routine techniques in the field of recombinant genetics, relying on the polynucleotide sequences encoding the Cry fusion protein disclosed herein.

A. Expression Systems

To obtain high level expression of a polynucleotide sequence encoding a recombinant protein, one typically subclones a polynucleotide encoding the protein in the correct reading frame into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the polypeptide are available in, e.g., *E. coli, Bacillus* sp., *Salmonella*, and *Caulobacter*. Kits for such expression systems are commercially available.

The promoter used to direct expression of a recombinant protein depends on the particular host cells used for the recombinant protein production. For instance, for effective expression in a *Bacillus* bacterial strain such as *Bacillus thuringiensis* (Bt) or *Bacillus subtilis* (Bs) cells, a promoter known to direct robust protein expression in these particular bacterial cells should be chosen. As shown in the Examples of this disclosure, two separate promoters, cyt1Aa and cry3Aa, have been successfully used to direct the expression of a recombinant protein as well as a Cry protein. The promoter is optionally positioned about the same distance from an exogenous or recombinant protein transcription start site as it is from the transcription start site in its natural setting. As is known in the art, however, some variation in this distance can be accommodated without loss of promoter function. In some cases, a constitutive promoter is used, whereas in other cases an inducible promoter rather than a constitutive promoter is preferred. Further, the placement of a common promoter or multiple separate promoters (which may be the same or different kind of promoters) and/or the placement of one or more separate ribosome binding sites separating different segments of coding sequences (each encoding a recombinant protein or a crystal-forming protein) in a common expression cassette (e.g., an expression vector such as a plasmid) can allow different expression ratios of the recombinant protein(s) to the crystal-forming protein so as to maximize the percentage of the recombinant protein(s) being entrapped or immobilized within the protein crystals formed by the crystal-forming protein such as a Cry protein, a crystal-forming fragment thereof, or a fusion protein comprising the Cry protein or the fragment.

In addition to the promoter, the expression vector typically includes a transcription unit or expression cassette containing all the additional elements that are required for the expression of the recombinant protein(s) and the crystal-forming protein in host cells. A typical expression cassette thus contains a promoter operably linked to the polynucleotide sequence encoding the recombinant protein and/or crystal-forming protein and signals required for efficient polyadenylation of the transcript, ribosome binding sites, and translation termination. The polynucleotide coding sequence may be linked to a cleavable signal peptide sequence to promote secretion of the polypeptide by the transformed cell. Such signal peptides include, among others, the signal peptides from tissue plasminogen activator, insulin, and neuron growth factor, and juvenile hormone esterase of *Heliothis virescens. Additional elements of the cassette may include enhancers and, if genomic DNA is used as the structural gene, introns with functional splice donor and acceptor sites.*

In addition to a promoter sequence, the expression cassette should also contain a transcription termination region downstream of the coding sequence to provide for efficient termination. The termination region may be obtained from the same gene as the promoter sequence or may be obtained from different genes. The placement of a commonly shared termination site in combination with the placement of multiple promoters directing transcription of multiple coding sequences can also be used to adjust the expression ratios of a recombinant protein to a crystal-forming protein, see, e.g., illustration in FIG. 4.

The particular expression vector used to transport the genetic information into the cell is not particularly critical. Any of the conventional vectors used for expression in eukaryotic or prokaryotic cells may be used, especially those suitable for expression in cells of *Bacillus* sp. such as Bt and Bs. Standard bacterial expression vectors include plasmids such as pBR322 based plasmids, pSKF, pET23D, and fusion expression systems such as GST and LacZ.

The elements that are typically included in expression vectors also include a replicon that functions in bacteria such as *Bacillus* sp. and *E. coli*, a gene encoding antibiotic resistance to permit selection of bacteria that harbor recombinant plasmids, and unique restriction sites in nonessential regions of the plasmid to allow insertion of coding sequences. The particular antibiotic resistance gene chosen is not critical, any of the many resistance genes known in the art are suitable. Similar to antibiotic resistance selection markers, metabolic selection markers based on known metabolic pathways may also be used as a means for selecting transformed host cells.

B. Transfection Methods

Standard transfection methods are used to produce bacterial, mammalian, yeast, insect, or plant cell lines that express large quantities of a recombinant fusion protein of this invention, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, J. Bact. 132: 349-351 (1977); Clark-Curtiss & Curtiss, *Methods in Enzymology* 101: 347-362 (Wu et al., eds, 1983).

Any of the well-known procedures for introducing foreign polynucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the recombinant protein(s) along with a crystal-forming protein (e.g., a Cry protein, a crystal-forming fragment thereof, or a fusion protein comprising a Cry protein or a crystal-forming fragment thereof) according to the method of this invention. As described above and herein, the recombinant protein or proteins (e.g., enzyme or enzymes) and the crystal-forming protein may be contained within one single expression cassette, e.g., in the same expression vector, where all coding sequences may be under the control of one single promoter, or each coding sequence may be under the control of a separate promoter (which optionally may differ from one another). In the alternative, each one of the coding sequences may be present in a separate expression cassette (e.g., expression vector). In either alternative, different ratios of the recombinant protein(s) to the crystal-forming protein may be achieved by using single copy or multiple copies of any one coding sequence or by placing separate or commonly shared ribosome binding site(s) and/or termination site(s) in the expression cassette, see, e.g., illustration in FIG. 4.

C. Isolation of Crystal-Entrapped Recombinant Proteins

Once the expression of the recombinant protein(s) along with a crystal-forming protein (e.g., a Cry protein, a crystal-forming fragment thereof, or a fusion protein comprising a Cry protein or a crystal-forming fragment thereof) in transfected host cells is confirmed, e.g., via electron micrograph for detecting protein crystals or an immunoassay such as Western blotting analysis, the host cells are then cultured in an appropriate scale for the purpose of purifying or isolating the recombinant protein entrapped within the protein crystals formed by the Cry protein, a crystal-forming fragment thereof, or a fusion protein comprising a Cry protein or a crystal-forming fragment thereof.

When the recombinant protein(s) and the crystal-forming protein are produced recombinantly by transformed bacteria in large amounts, for example after promoter induction, the recombinant protein(s) become entrapped within the crystals formed by the crystal-forming protein. In other words, the recombinantly produced proteins are present in crystalline form or insoluble aggregates within the host cells. Thus, one can readily isolate the crystals from the cell lysate based on their distinct density by utilizing techniques such as centrifugation and density gradient separation followed by one or more rinsing steps to further remove contaminants from the protein crystals.

There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.10% Nonidet P40, a non-ionic detergent. The cell suspension can be ground using a Polytron grinder (Brinkman Instruments, Westbury, NY). Alternatively, the cells can be sonicated on ice. Additional methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Upon isolation, the recombinant protein(s) recovered from host cells in the form of protein crystals, the protein or proteins may be directly used according to their inherent biological activity: for example, a lipase entrapped in Cry protein crystals may be used in a reaction to hydrolyze triglycerides. By virtue of being in an insoluble crystal form, the lipase has a heighted level of resistance to harsh environmental conditions such as high temperature, extreme pHs, organic solvents, etc., thus allowing repeated cycles of cleaning and reuse.

In the alternative, following the washing step, the inclusion bodies are solubilized to release the entrapped recombinant protein(s) by the addition of a solvent that is both a strong hydrogen acceptor and a strong hydrogen donor (or a combination of solvents each having one of these properties). The protein(s) from the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein(s) can be separated from other bacterial proteins by standard separation techniques. For further description of purifying recombinant polypeptides from bacterial inclusion body, see, e.g., Patra et al., *Protein Expression and Purification* 18: 182-190 (2000).

While the protein crystals tend to remain insoluble at lower or neutral pHs, placing them in alkaline solutions with pH at or greater than 10 or 11 can often effectively dissolve the protein. Once dissolved, the protein can then be analyzed by gel separation (e.g., on an SDS gel) and immunoassays to confirm its identity based on the appropriate molecular weight and immunoreactivity.

IV. Applications of Immobilized Proteins

Another aspect of the present invention relates to the use of a recombinant protein, especially an enzyme, entrapped and immobilized in protein crystals produced according to the methods described herein to exert the protein's inherent biological activity, for example, to perform reactions typically catalyzed by the enzyme present in the protein crystals, such as hydrolysis, esterification, ligation, proteolysis, and the like. As organic solvents are often able to facilitate such reactions and the immobilized recombinant protein produced by the method of this invention is highly tolerant to the presence of organic solvents, a reaction performed using the immobilized protein according to this invention often not only a water-based solvent but also one or more organic solvents, e.g., ethanol, methanol, acetonitrile, and dimethylformamide.

As the inventors discovered that immobilization of recombinant protein(s) within the crystalline Cry protein or fusion proteins leads the protein(s) to have a higher level of resistance to organic solvents and a higher level of thermostability, potentially can retain enzymatic activity for use in more cycles of reactions. In some cases, this reaction process includes a cleaning step, performed after the completion of one round of the reaction and removal of the reaction product(s) as well as any remaining substrate, during which the protein crystals containing recombinant protein(s) are rinsed or washed in preparation of being used again with fresh substrate in a subsequent round of reaction.

EXAMPLES

The following examples are provided by way of illustration only and not by way of limitation. Those of skill in the art will readily recognize a variety of non-critical parameters that could be changed or modified to yield essentially the same or similar results.

Example 1

Introduction

Immobilization of Enzymes

The major bottleneck to the practical use of enzymes as industrial catalysts is the cost of production and useable lifetime. While biomolecular engineering methods can be used to enhance enzyme stability, these techniques do not aid in rapid production and isolation, particularly when high purities are necessary. A cost-effective biocatalyst should be able to be recycled over many reaction cycles, with minimal loss of activity. One method to improve enzyme stability and make them reusable is immobilization, either by covalent attachment to beads, or by adsorption into porous materials. Immobilization of enzymes allows them to be easily filtered and reused over successive reaction cycles, and in some cases can lead to increased temperature stability and/or organic solvent tolerance due to the reduced conformational flexibility of the enzyme in the matrix[1]. This rigidity is also beneficial to mechanical stability by helping to protect against the constant agitation that occurs in large-scale reactors.[2]

A major limitation of both bead attachment and porous material adsorption approaches, however, is that ~90-99% of the biocatalyst composite is inactive, greatly reducing the catalytic productivity per weight.[3] Furthermore, these approaches require multiple steps: (1) production and purification of the enzyme catalyst, (2) production of the support, and (3) anchoring of the enzyme catalyst on the support. These steps can add significantly to the cost and impact catalytic activity. If a strategy can be developed to generate and isolate an immobilized lipase in a single step, it can dramatically lower the cost of the catalyst.

Genetically-Encoded Immobilized Lipases

Genetically-encoded, or in-vivo, immobilization approaches that involve the direct production of immobilized enzymes in bacterial cells, represents a promising direction for more efficient and economical biocatalyst production. Consolidating expression and immobilization into a single step removes the need of columns for enzyme purification, as well as reagents to introduce reactive chemistries, greatly reducing time and production costs.

One of the earliest reports of producing active enzyme particles in cells came from the work of Worrall et al., who showed that they could produce catalytically active inclusion bodies (CatIBs) of β-galactosidase in *E. coli*.[4] This discovery upended the paradigm that inclusion bodies (IBs) were inactive waste species in cells and prompted the idea that IBs could be used as immobilized catalysts. Since most enzymes are naturally soluble, producing CatIBs can be a challenge. Thus most approaches to produce in vivo immobilized enzymes have involved the incorporation of a fusion-tag to promote aggregation.

Several fusion tags have been exploited to generate immobilized enzymes in vivo including self-aggregating peptides and protein domains. Peptide tags such as ELK16 and $L_6KD$ have been successfully fused to target enzymes to drive in vivo aggregation. While the use of tags resulted in the formation of highly active enzyme aggregates, none of the these aggregates was shown to be reusable.[5,6] Similarly, several protein domains have been used to promote in vivo enzyme immobilization in cells.[7-9] The most successful example has been the work of Diener et al. who used the short coiled-coil domain TDoT of the cell-surface protein tetrabrachion from the hyperthermophilic archaeon *Staphylothermus marinus* to immobilize several enzymes.[10;11] While enzymes immobilized by the TDoT tag displayed good recyclability, the aggregates produced generally had low activity due to diffusion limitations. Identifying a platform capable of promoting the production of in vivo immobilized enzymes with both high activity and good reusability had until recently, remained elusive.

Cry-Enzyme Fusion Proteins as Genetically-Encoded Immobilized Catalysts

Figure 3:
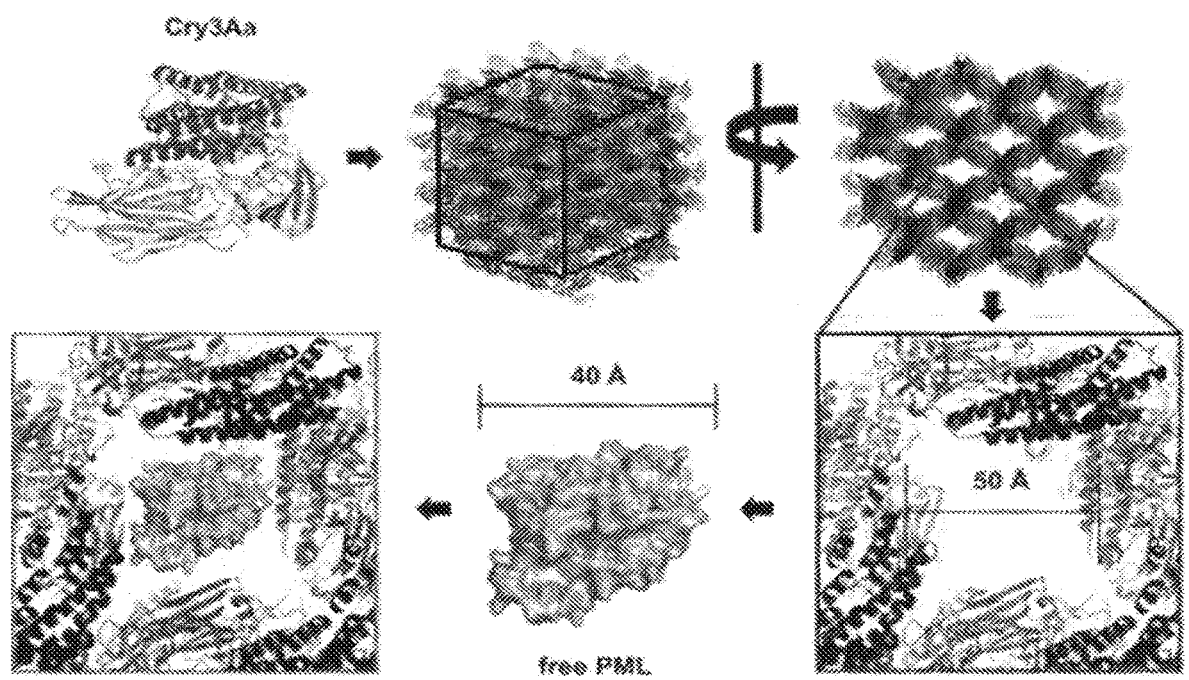
FIG. 3. Schematic illustrating the potential mode of entrapment of PML within Cry3Aa crystals (modified from reference 16).
Figure 5:
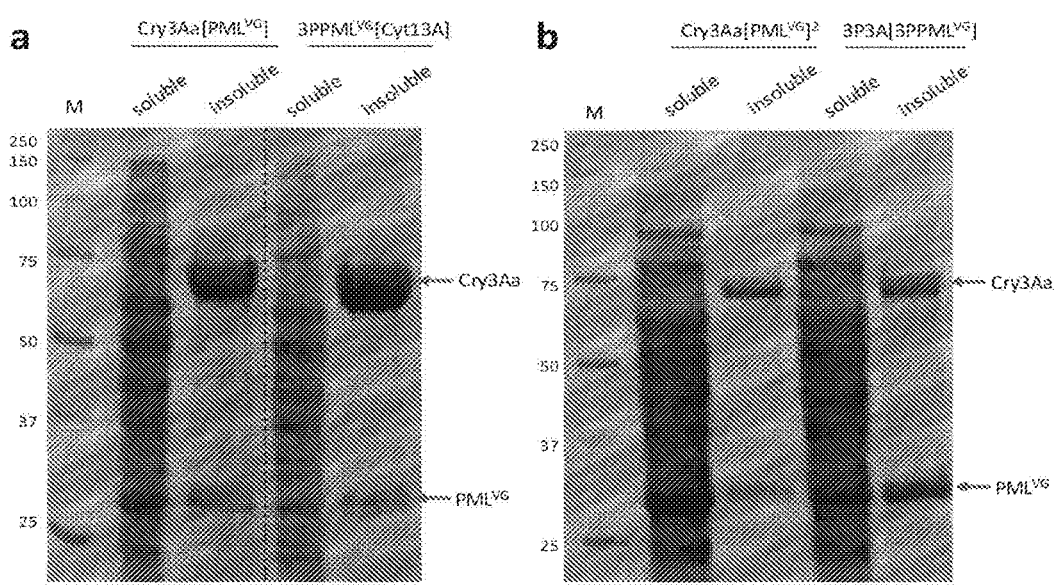
FIG. 5. SDS-PAGE analysis of PML$^{VG}$ entrapped in Cry3Aa crystals by different coexpression methods. (a) Analysis of Cry3Aa[PML$^{VG}$] and 3PPML$^{VG}$[Cyt13A] crystals and (b) Cry3Aa[PML$^{VG}$]$^2$ and 3P3A[3PPML$^{VG}$] crystals. Lane (M) molecular weight marker (kDa).
Figure 6:
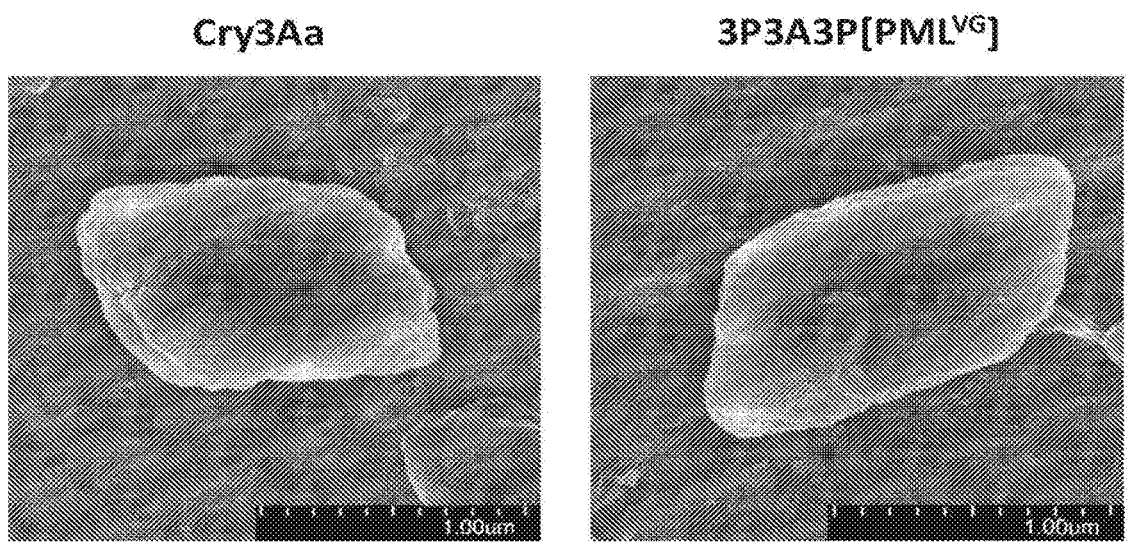
FIG. 6. Scanning electron micrographs of Cry3Aa and 3P3A3P[PML$^{VG}$] crystals.
Figure 7:
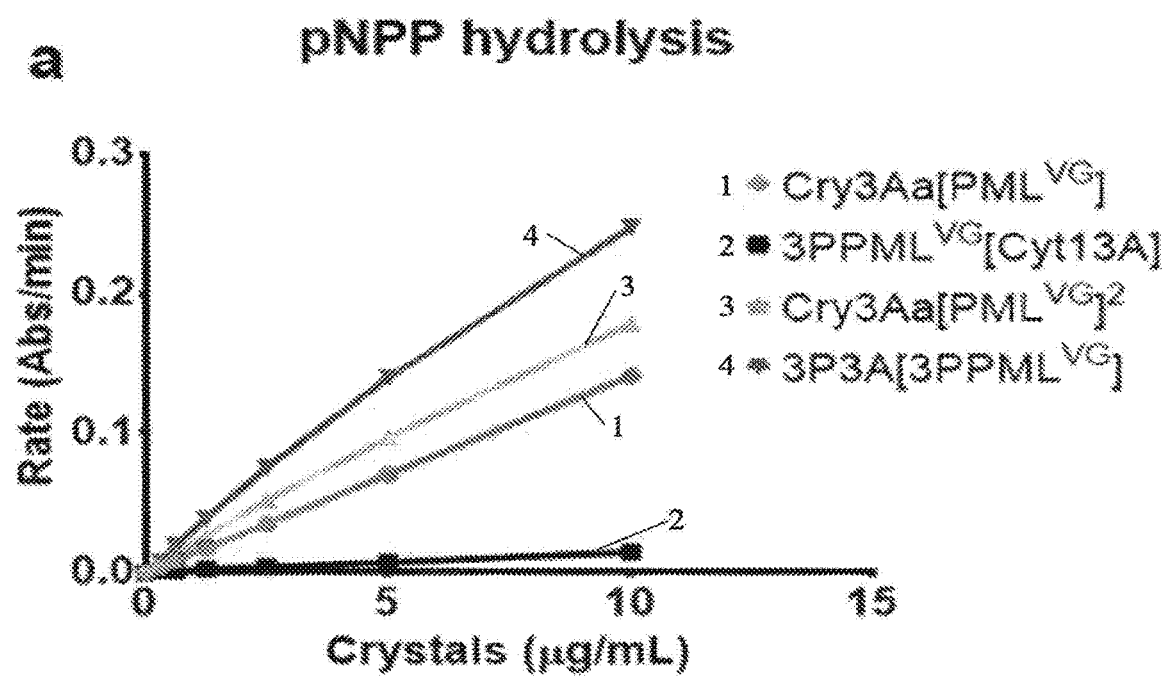
FIG. 7. p-Nitrophenyl palmitate (pNPP) hydrolysis activity of PML$^{VG}$ entrapped in Cry3Aa crystals by different coexpression methods.
Figure 10:
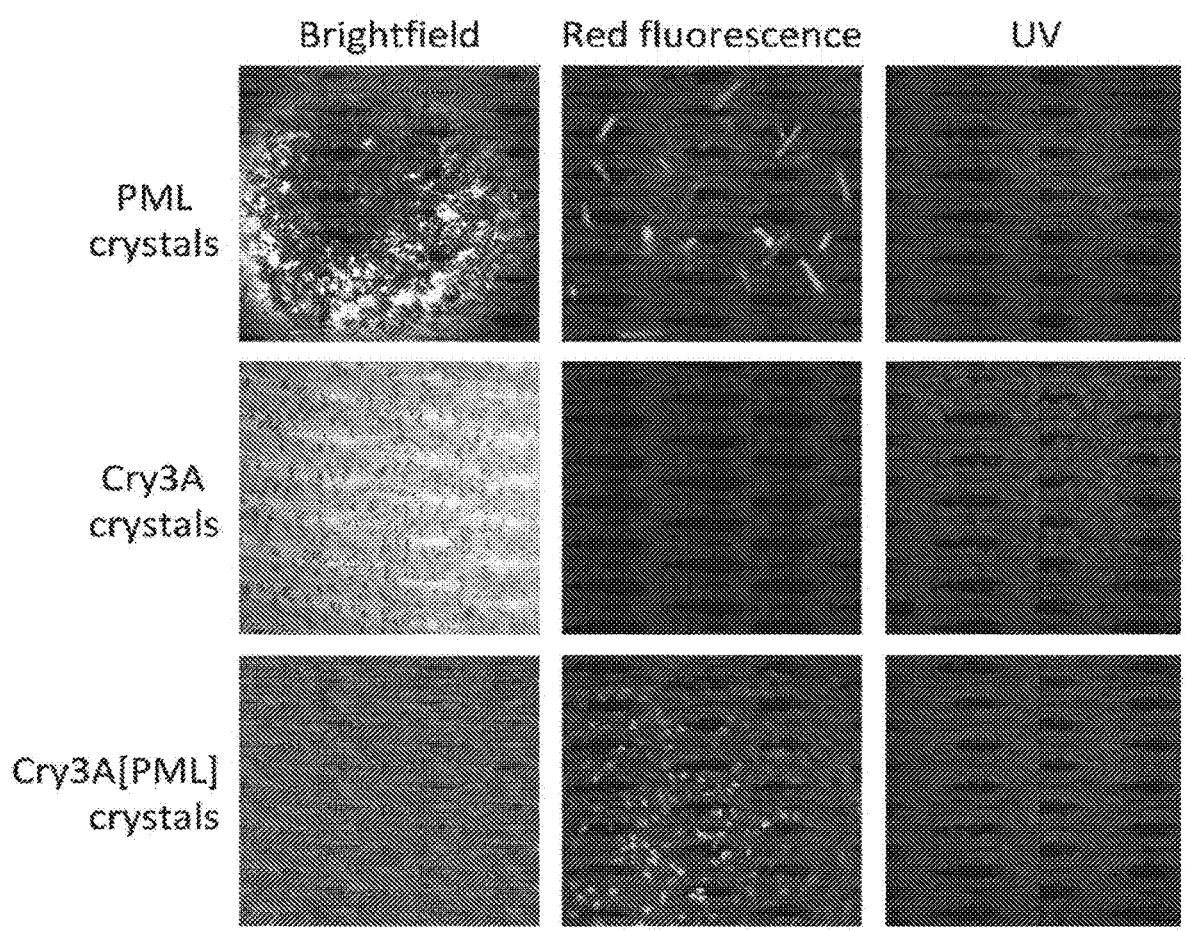
FIG. 10. In vitro co-crystallization of Cry3Aa and carboxy rhodamine labelled PML by vapor diffusion. Crystals with red fluorescence but no UV fluorescence are crystals comprised of PML only. Crystals with UV fluorescence but not red fluorescence are Cry3Aa crystals that do not contain PML. Entrapment of PML inside Cry3Aa crystals is confirmed by finding crystals with both red and UV fluorescence.
Figure 11:
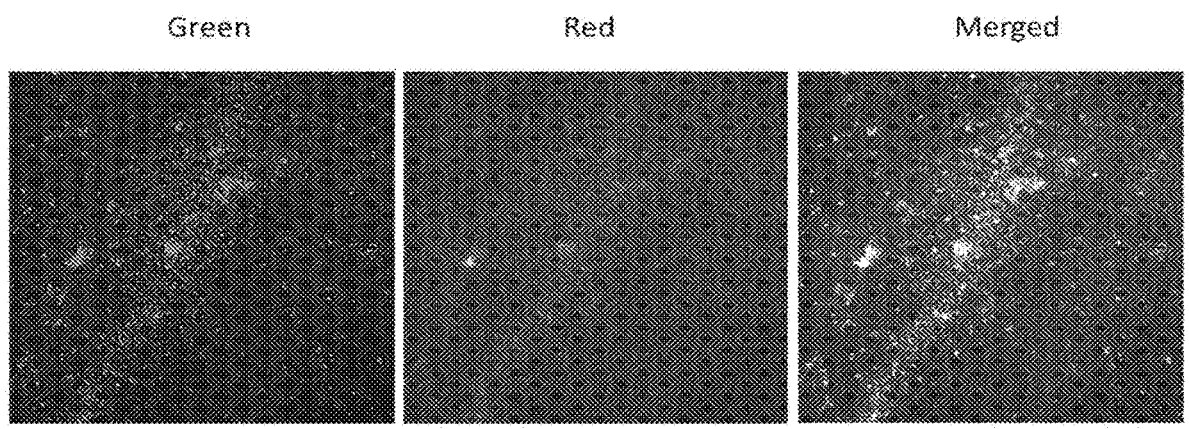
FIG. 11. Fluorescence microscopy of Cry3Aa co-entrapment of GFP and mCherry fluorescent proteins. The data demonstrate that GFP and mCherry proteins are entrapped in single Cry3Aa crystals.
Figure 12:
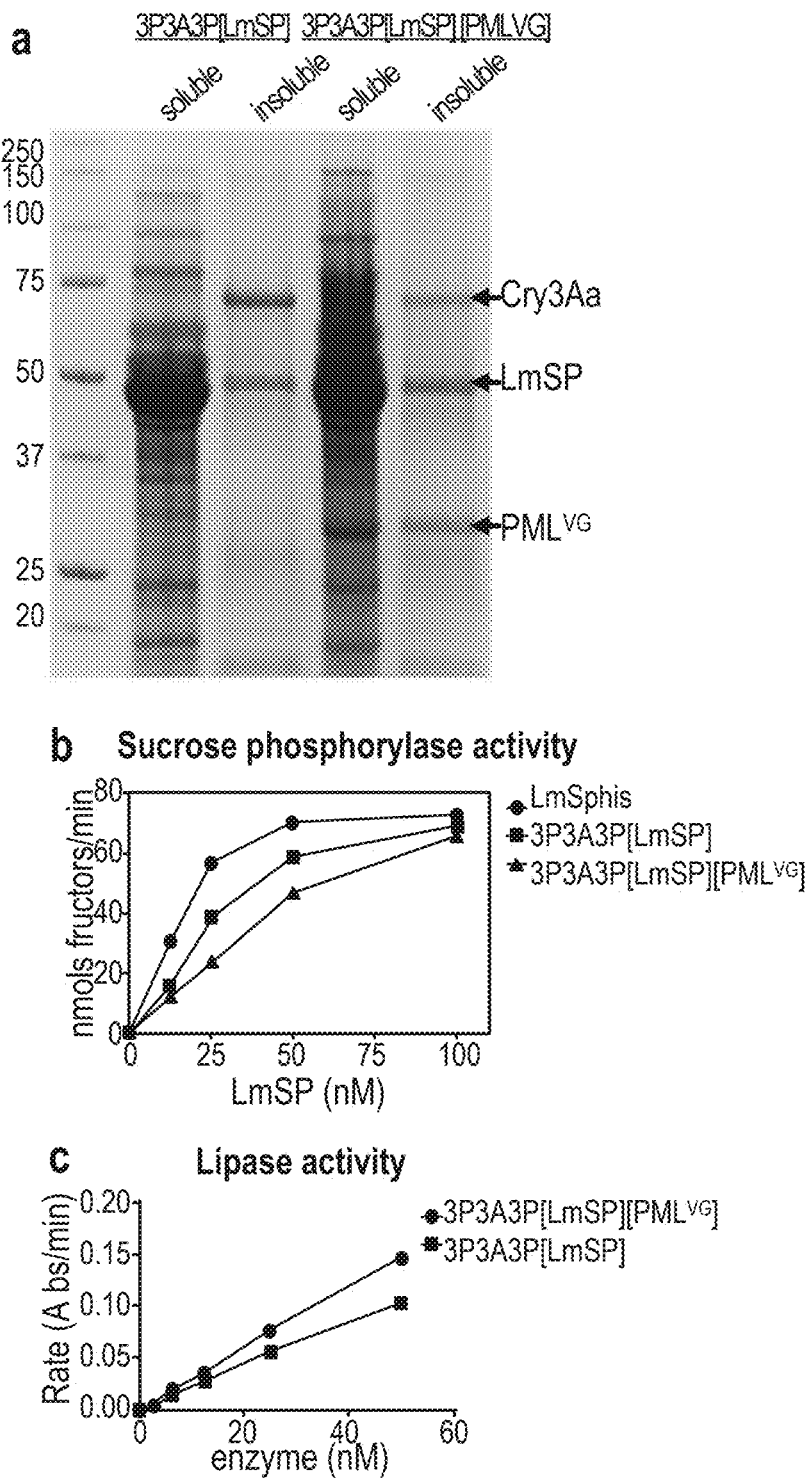
FIG. 12. Production and analysis of LmSP entrapment in Cry3Aa crystals. (a) SDS-PAGE analysis of 3P3A3P [LmSP] and 3P3A3P[LmSP][PML$^{VG}$] crystals. (b) Sucrose phosphorylase activity and (c) lipase activity of coentrapped crystals.
Figure 13:
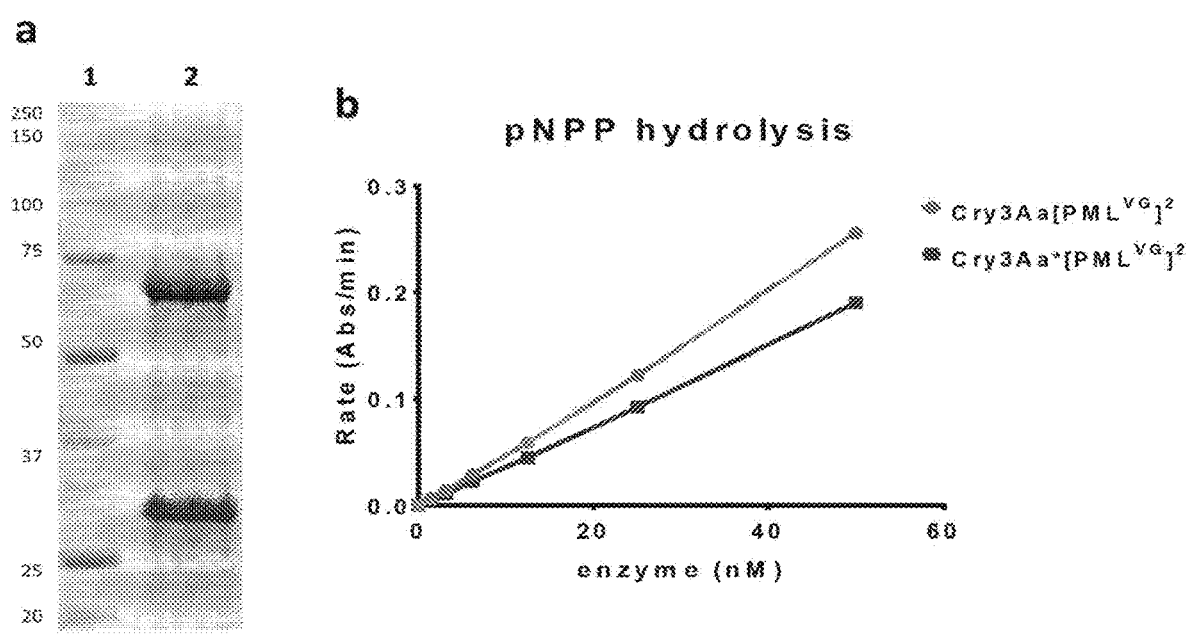
FIG. 13. Production and characterization of Cry3Aa* [PML$^{VG}$]$^2$ crystals. (a) SDS-PAGE gel of purified Cry3Aa* [PML$^{VG}$]2 crystals. Lane (1) molecular weight marker (kDa), Lane (2) crystals. (b) pNPP hydrolysis activity of Cry3Aa*[PML$^{VG}$]$^2$ crystals.
Figure 15:
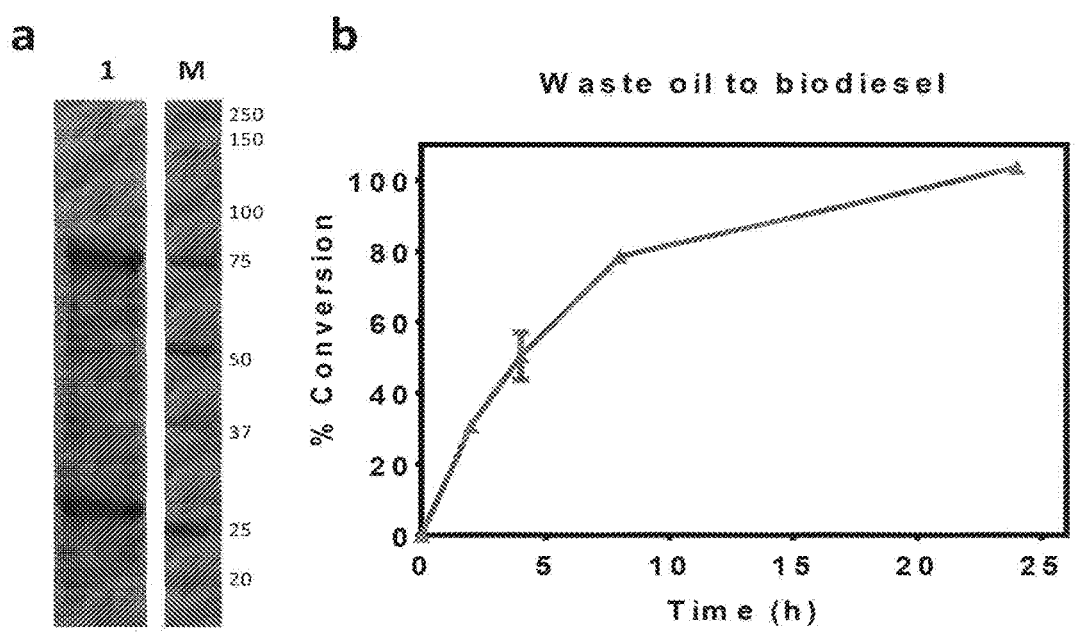
FIG. 15. Production and characterization of Cry3Aa*-lipA[PML$^{VG}$] crystals. (a) SDS-PAGE analysis of purified Cry3Aa*-lipA[PML$^{VG}$] crystals. Lane (1) Pure crystals; lane (M) molecular weight marker (kDa). (b) Time-point study of waste cooking oil conversion to biodiesel.
Figure 19:
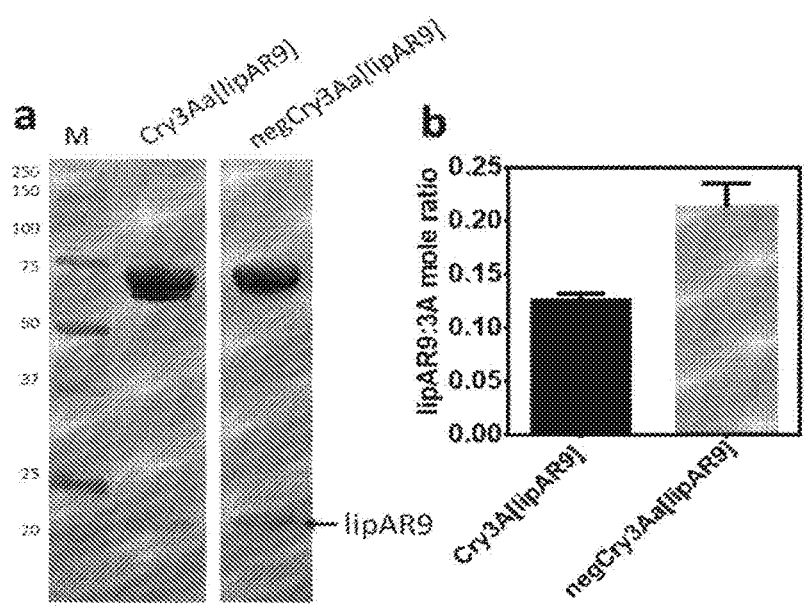
FIG. 19. Entrapment of lipAR9 in negCry3Aa crystals. (a) SDS-PAGE analysis of Cry3Aa[lipAR9] and negCry3Aa [lipAR9] crystals. (b) Quantitation of loading of lipAR9 in Cry3Aa and negCry3Aa crystals.
Figure 20:
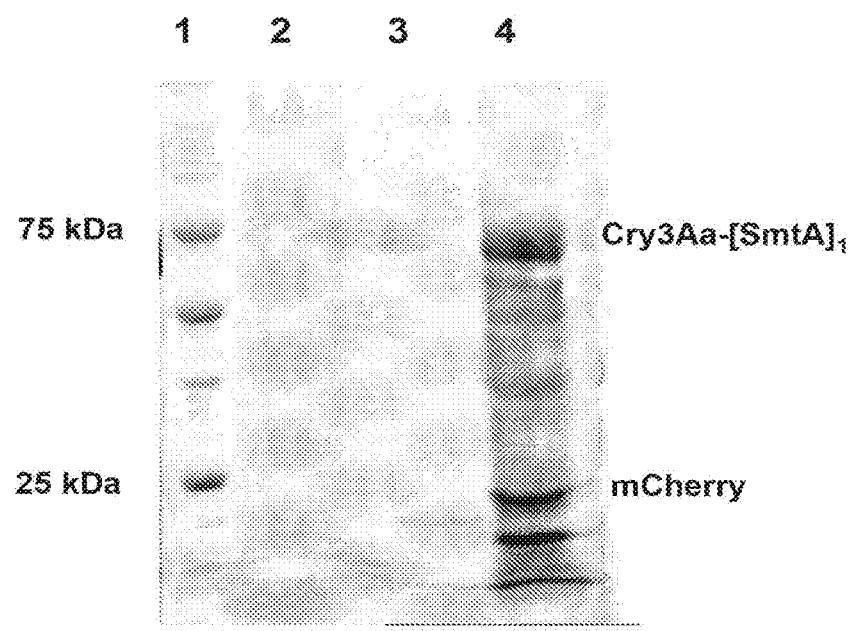
FIG. 20. SDS-PAGE of Cry3Aa-[SmtA]$_1$ produced in Bt and purified by sucrose density gradient centrifugation. Lane 1: BioRad Precision plus molecular weight marker; lane 2-3: Extracts from <40% sucrose layers; lane 4: crystal extracts from the interface of 40%/60% sucrose layer.
Figure 21:
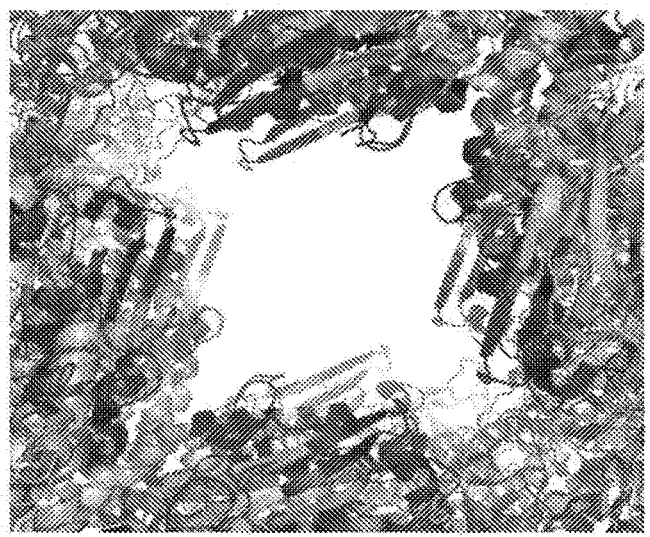
FIG. 21. Structure of Cry3Aa crystal channel. Residues highlighted in red are regions exposed to the solvent channel and can be deleted to expand the channel size.
Figure 24:
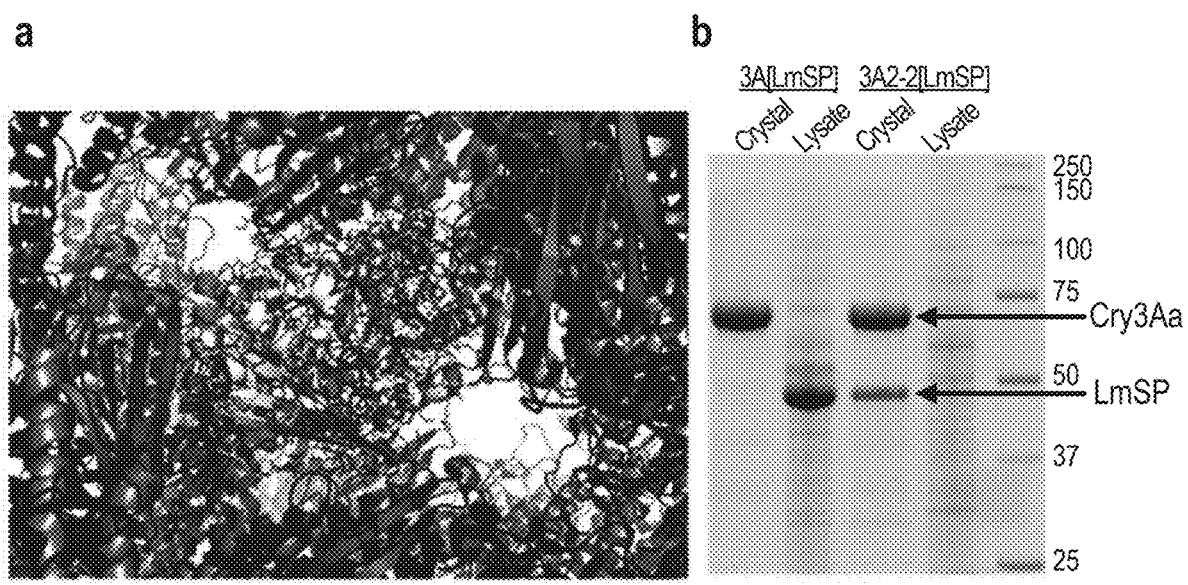
FIG. 24. Entrapment of LmSP in 3A2-2 crystal. (a) Model of LmSP homolog *Thermoanaerobacter thermosaccharolyticum* 6F-phosphate phosphorylase (PDB ID: 6S9V) inside the Cry3Aa crystal (PDB ID: 1DLC) channel. Loop regions that are oriented in the channel with potential steric clash with LmSP are colored red. LmSP is colored yellow with its amino acids colored in black and portrayed as lines. Cry3Aa is colored blue. Model was produced in COOT and images were prepared in PyMol. (b) SDS-PAGE analysis after entrapment of LmSP in the wild-type Cry3Aa crystal (3A [LmSP]) and in the mutant 3A2-2 crystal (3A2-2[LmSP]).
Figure 25:
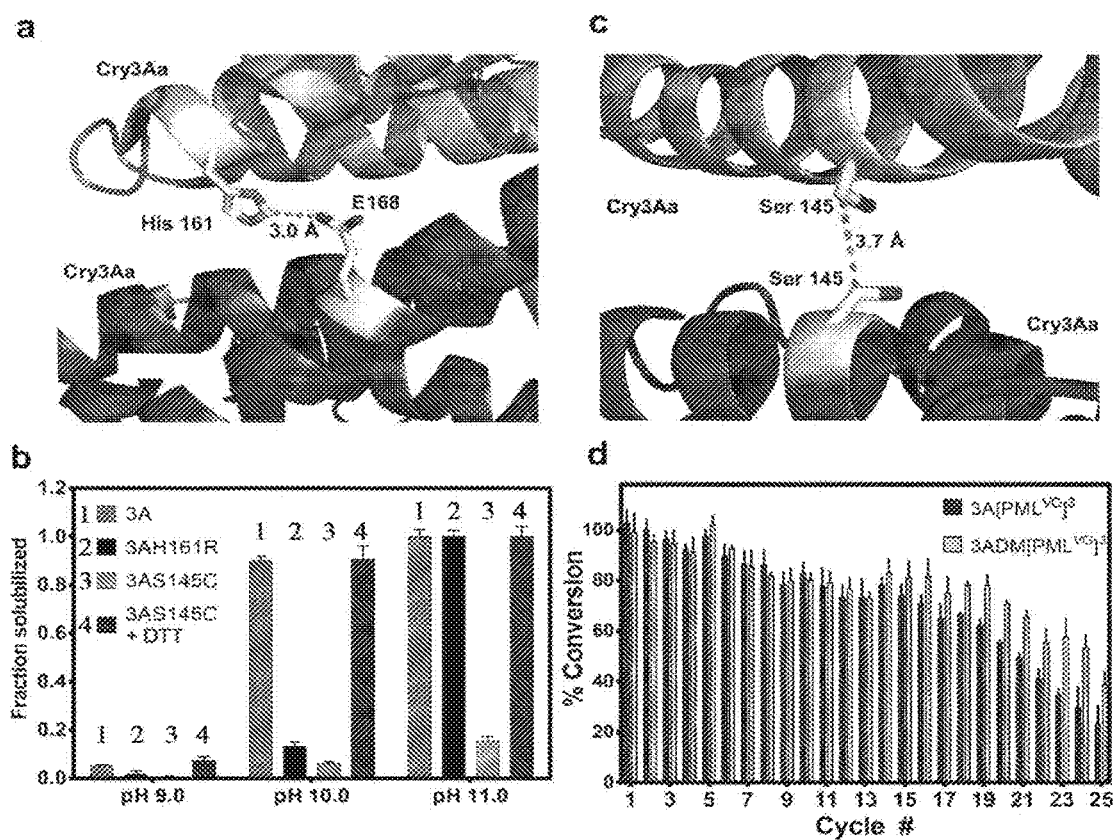
FIG. 25. Stabilizing mutations in Cry3Aa protein. (a) Structure of two Cry3Aa monomers showing His161-E168 electrostatic interaction. (b) Solubilization resistance of Cry3Aa mutants. (c) Structure of two Cry3Aa monomers showing potential site for disulfide formation. (d) Recyclability of PML$^{VG}$ triple copy constructs 3A[PML$^{VG}$]$^3$ and double mutant 3ADM[PML$^{VG}$]$^3$ during the synthesis of biodiesel from waste cooking oil.

Recently a new strategy was developed to produce genetically-encoded immobilized enzymes based on crystal proteins (Cry), such as Cry3Aa. Cry proteins are insecticidal proteins that innately form crystals inside the bacterium *Bacillus thuringiensis* (Bt) (FIG. 3).[12-14] It was previously demonstrated that expression of Cry3Aa fused to GFP or mCherry yielded fluorescent protein crystals in Bt—indicating that the fusion partners were folded and functional.[15] Electron microscopy carried out on Cry3Aa crystals and Cry3Aa-GFP crystals revealed them to be similar in size, indicating that the fusion partner does not change the crystal packing (FIG. 3*b,c*).[15]

The use of this Cry crystal platform to produce genetically-immobilized lipases as potential biodiesel catalysts was explored, see, e.g., WO2018/028371. The first-generation biodiesel catalyst was generated by genetically fusing *Bacillus subtilis* lipase A (lipA) to the C-terminus of a truncated Cry3Aa (Cry3Aa*) and then producing the fusion protein in Bt. The resultant Cry3Aa*-lipA fusion crystals exhibited higher catalytic activities compared to free lipA, as well as improved solvent and temperature stability.[16] Significantly, the Cry3Aa*-lipA fusion crystals can be used to produce biodiesel from coconut oil with high conversion efficiency over 10 reaction cycles (FIG. 4). These properties made the Cry3Aa*-lipA catalyst the first example of a genetically-encoded immobilized enzyme that retained both high activity and recyclability.

Cry3Aa as a Carrier for Enzyme Entrapment

A potential limitation of using Cry3Aa-fusion crystals, however, is that the enzyme of interest is chemically modified at its N-terminus, which can hamper enzyme activity. Moreover, fusion to a bulky Cry3Aa protein may cause problems to the enzyme during folding. Indeed, Cry3Aa-fusion enzymes of a *Proteus mirabilis* lipase have been generated, which only retained 5% activity of retention compared to wild-type. This motivated further efforts to explore novel approaches to produced immobilized enzymes using Cry3Aa.

Cry3Aa proteins crystals contain large porous 50 Å×50 Å channels. It is envisaged that these channels can act as cages to trap the enzyme of interest inside (FIG. 3). Since Cry3Aa forms a crystal the target enzyme should be spatially confined and ordered such that each monomer does not interfere with the other. Moreover, since the unit cell dimensions of Cry3Aa are known, one can quantify the amount of enzyme molecules loaded into the Cry3Aa crystals, a characteristic can be measured using the Cry3Aa-fusion crystals based on the structural information. Most importantly, this strategy retains the feature of a one-step immobilization platform, and the entrapped enzyme is much more likely to be in its native state since there are no covalent modifications.

Results and Discussions

Entrapment of PML Inside Cry3Aa Crystals

*Proteus mirabilis* lipase (PML) is a bacterial lipase capable conversion of vegetable oils including waste cooking oil to biodiesel. PML is highly soluble and expresses well in *E. coli*. The potential of PML fused to Cry3Aa was recently explored as a catalyst for biodiesel production from canola oil and waste cooking oil, and an optimized mutant containing two-point mutations (I118V, E130G, $PML^{VG}$) was produced. PML is a good target for Cry3Aa entrapment since the fusion of PML to Cry3Aa drastically reduces the activity. Additionally, the size of PML (55 Å×41 Å×26 Å) is a good fit for the Cry3Aa channel (FIG. 1). For clarity, square brackets ([ and]) are used to indicate the entrapment of the PML molecules (e.g., Cry3Aa[PML]), whereas a hyphen (-) indicates a genetic fusion (e.g., Cry3Aa-PML).

Several plasmid variations were generated to improve the amount of PML loaded into the crystals. A list of these constructs is displayed in FIG. 4. The initial Cry3Aa[PML] coexpression cassette was generated by cloning the PML gene containing a separate ribosome binding site downstream of Cry3Aa. This plasmid was transformed, expressed and the resulting crystals were purified as described previously.[15] Solubilization of the crystals and analysis by SDS-PAGE indicated that the Cry3Aa crystals contained PML (FIG. 5*a*).

Several methods were tried to improve the PML loading into the Cry3Aa crystals. First, Cry3Aa was put under the control of two cyt1Aa promoters[17] and PML under one cry3Aa promoter (3P$PML^{VG}$[Cyt13A]). It was anticipated that the temporal difference between the promoters (cyt1Aa is activated during late-stage sporulation while cry3Aa is activated during vegetation and early-stage sporulation) would cause PML to accumulate in the cell first and increase the relative ratio of PML to Cry3Aa during crystallization. Although PML entrapment was achieved, the loading was much lower than Cry3Aa[$PML^{VG}$](FIG. 5*a*).

Another approach was based on increasing the ratio of PML to Cry3Aa in the transcript. This was accomplished implementing two strategies. First, by inserting another copy of PML downstream of Cry3Aa[$PML^{VG}$] making Cry3Aa [$PML^{VG}$]$^2$. Since the proteins are under one promoter, each transcript will have double the amount of PML per Cry3Aa. Second, by putting Cry3Aa and PML under two separate cry3Aa promoters but only one terminator (3P3A [3P$PML^{VG}$]). In the latter case, for each transcript containing Cry3Aa there will be two transcripts containing PML. Each of these strategies should result in a theoretical 2:1 PML:Cry3Aa ratio. Both constructs resulted in higher loading of PML into the Cry3Aa crystals, albeit 3P3A [3P$PML^{VG}$] demonstrated the highest loading efficiency at 64-75% depending on the batch (FIG. 5*b*). This corresponds to around $4\times10^5$ to $6\times10^5$ molecules of $PML^{VG}$ per crystal, which is unprecedented in terms of enzyme loading. Notably, these crystals retained near identical morphology and size to native Cry3Aa crystals (FIG. 6).

The activities of all the resulting PML entrapped Cry3Aa crystals were determined by measuring the hydrolysis of p-nitrophenyl palmitate. As demonstrated in FIG. 7, higher PML loading into the crystals resulted in higher activity per pg crystal, with the 3P3A3P[$PML^{VG}$] construct displaying the highest activity. Moreover, entrapment of $PML^{VG}$ inside Cry3Aa crystals significantly stabilized it against thermal denaturation, displaying a 200-fold increase in residual activity after incubation for 1 h incubation at 58° C. (FIG. 8B).

With the optimized immobilized lipase at hand, the practicality of the catalyst for industrial reactions was tested. Two common applications of lipases are biodiesel production (Scheme 1 in FIG. 16A) and ester synthesis in organic solvents such as the cosmetic compound benzyl laurate (Scheme 2 in FIG. 16A).

The optimized Cry3Aa[$PML^{VG}$] crystals were capable of converting waste cooking oil into biodiesel in 10 h and retained maximal conversion for 7 reaction cycles (FIG. 8A). These data support the high catalytic activity and stability of the immobilized catalyst for biodiesel production.

For benzyl laurate synthesis, the optimized Cry3Aa [$PML^{VG}$] crystals were lyophilized in water for 24 h. The dried crystals were then reacted with 10 mM benzyl alcohol and 10 mM lauric acid in neat isooctane for 24 h. Gas chromatography-mass spectrometry (GCMS) analysis of the reaction mixture revealed that benzyl laurate was produced (FIG. 9). While this reaction has not been optimized to maximize yield, it demonstrates that the Cry3Aa entrapped crystals can be used in neat organic solvents for synthesis reactions.

As further demonstration that PML can be entrapped within Cry3Aa crystals, in vitro co-crystallization of carboxy-rhodamine-labelled PML and Cry3Aa was performed by vapor diffusion (FIG. 10). Since only Cry3Aa exhibits fluorescence upon UV (280 nm) irradiation, and PML is dye-labelled, formation of Cry3Aa-entrapped PML crystals could be confirmed based on their fluorescent properties (FIG. 10). Notably, these data demonstrate that Cry3Aa-mediated entrapment can also be performed in vitro.

Coentrapment of Multiple Proteins Inside Cry3Aa Crystals

One major advantage of using enzyme over chemical catalysis is that enzymes are specific, allowing for multiple reactions to occur in one-pot without unwanted side reactions or side products. It was hypothesized using the expression platform one could entrap multiple enzymes simultaneously in a single crystal. Notably, this would offer a significant advantage over other multi-enzyme systems since there is no need to purify the enzymes separately. As a proof of concept, mCherry, green fluorescent protein (GFP) and Cry3Aa were incorporated on the same plasmid and expressed in Bt. Cry3Aa was expressed under one Cry3Aa promoter, while GFP and mCherry were expressed on a separate Cry3Aa promoter separated by a ribosome binding site. Crystals produced contained both red and green fluorescence indicating co-entrapment of both proteins occurred in a single crystal (FIG. 11).

Co-immobilizing two or more enzymes on a single platform can be beneficial to either impart the catalyst with a broader substrate specificity or generate a coupled system that promotes the synthesis of higher value products. In the latter case, active site proximity can lead to much faster turnover rates since intermediates are released in close proximity to the subsequent active site, so that they can be quickly turned over before diffusing away.

Glycerol—a byproduct of FAME biodiesel production is usually extracted from the aqueous layer and purified prior to its separate commercialization. A more efficient and value-added approach would be to simultaneously convert glycerol to a cosmetic product during the transesterification process. Not only would this save time by doing both reactions in one pot, but also removal of glycerol might increase the efficiency and yield of FAME biodiesel by pulling the equilibrium of transesterification reaction towards the products via Le Chatelier's principle.

Among glycerol-derived cosmetics, glycosylated glycerol such as 2-O-(α-D-gluco-pyranosyl)-sn-glycerol (αGG) has gained a lot of attention as a powerful moisturizing agent.[30] Interestingly, Goedl et al. demonstrated that they could produce this compound enzymatically from sucrose and glycerol using a sucrose phosphorylase enzyme from *Leuconostoc mesenteroides* (LmSP).[30] Therefore, it would be plausible to simultaneously convert oil to biodiesel and αGG using a one-pot combination of PML and LmSP (Scheme 3 in FIG. 16B).

Having already entrapped PML inside Cry3Aa crystals, the inventors' next step was to first verify that LmSP can be entrapped inside Cry3Aa crystals as well. A plasmid was constructed that coexpresses Cry3Aa and LmSP on separate cry3Aa promoters. This plasmid was transformed and expressed in Bt. SDS-PAGE analysis of the crystals indicated that LmSP was entrapped inside Cry3Aa crystals with high efficiency –33% of the protein molecules in the crystals are LmSP (FIG. 12*a*). For the LmSP:PML dual catalyst construct, a copy of $PML^{VG}$ was inserted downstream of LmSP with its own ribosome binding site. After expression of this new construct 3P3A3P[LmSP][$PML^{VG}$] in Bt and purification, SDS-PAGE analysis revealed that both LmSP and $PML^{VG}$ were entrapped in Cry3Aa crystals with high efficiency (FIG. 12*a*). These 3P3A3P[LmSP][$PML^{VG}$] crystals displayed both high sucrose phosphorylase activity (FIG. 12*b*) and pNPP hydrolysis activity (FIG. 12*c*).

Entrapment of PML Inside Cry3Aa* Crystals

A potential limitation of using native Cry3Aa crystals is that they are soluble at alkaline pH. Thus, reactions performed at alkaline pH will cause Cry3Aa to solubilize and release the entrapped protein or enzyme. It was previously demonstrated that truncation of 18 amino acids from the C-terminus of Cry3Aa and expression in Bt resulted in the production of particles that were much more resistant to solubilization. It was hypothesized that if these C-terminally truncated crystals (Cry3Aa*) still retained pores they could also entrap proteins or enzymes in vivo. To test this, Cry3Aa* and two copies of $PML^{VG}$ were put under a single cry3Aa promoter with each protein having its own ribosome binding site. As expected, SDS-PAGE analysis demonstrated that $PML^{VG}$ was entrapped in Cry3Aa* crystals with high efficiency and the resulting Cry3Aa*[$PML^{VG}]^2$ crystals displayed high activity (FIG. 13).

Entrapment of PML Inside Cry3Aa-Fusion Crystals

One can envisage that if Cry3Aa-fusion crystals formed pore-like structures they should also be capable of enzyme entrapment. Notably, this would be a facile strategy to produce multi-protein or multi-enzyme immobilized systems. Some advantages to this system over co-entrapment in native Cry3Aa crystals are that the fusion partner will be expressed in a 1:1 ratio as Cry3Aa, so proteins or enzymes that exhibit poor expression levels can be fused to Cry3Aa or Cry3Aa*. The feasibility of this approach by coexpressing Cry3Aa* fused to SpyCatcher (Cry3Aa*-SpyCat) and $PML^{VG}$ to produce Cry3Aa*-SpyCat[$PML^{VG}$] crystals (FIG. 13*a*) has already been demonstrated. While SpyCatcher (10 kDa) is not an enzyme, it can act as a reaction handle to conjugate candidate enzymes fused with a Spytag to produce immobilized dual enzyme crystals.

It was recently discovered that CotA-laccase can convert linoleic acid, an abundant fatty acid in waste oils, into azelaic acid, a valuable chemical used in the cosmetic, pharmaceutical and polymer industries.[16] Thus instead of using methanol to produce biodiesel, lipase mediated hydrolysis of the triacylglycerols in water will generate free linoleic acid, which can be subsequently converted to azelaic acid by CotA-laccase (Scheme 4 in FIG. 16B). Since CotA expression is low, it is a good candidate for conjugation to the Cry3Aa*-SpyCat[$PML^{VG}$] crystals to produce the lipase:lacasse catalyst. Preliminary results described herein indicate successful conjugation of CotA-Spytag Cry3Aa*-SpyCat[$PML^{VG}$] crystals, with full retention of lacasse activity (FIG. 13).

Another example of entrapment of proteins inside Cry3Aa-fusion crystals is the entrapment of $PML^{VG}$ inside Cry3Aa*-lipA crystals. Waste cooking oils are economical feedstocks for biodiesel production, but they have various compositions from source to source. Therefore, production of a single catalyst containing lipases with different chain specificities would be a versatile catalyst for waste cooking oil conversion to biodiesel. The plan was to coexpress Cry3Aa, PML mentioned previously, and lipase A from *Bacillus subitilis* (lipA) in the same Bt cell. PML prefers long chain fatty acids $C_{14}$-$C_{20}$ while lipA prefers medium chain fatty acids $C_6$-$C_{12}$. Experimental data showed that $PML^{VG}$ could be entrapped inside Cry3Aa*-lipA crystals and the resulting dual lipase construct was an effective catalyst for waste cooking oil conversion to biodiesel (FIG. 14).

Example 2

Crystals Formed from Cry3Aa Mutants with Multiple Negatively Charged Amino Acid Substitutions (NegCry3Aa) Enhance the Binding of Certain Proteins To investigate whether Cry3Aa protein crystal can be engineered to enhance its affinity to the encapsulated protein cargo, a negatively-charged Cry3Aa mutant (negCry3Aa) was generated by substituting specific residues within Domain II that are exposed to the crystal solvent channel with negatively-charged amino acids, namely, aspartate (D) and glutamate (E). For initial studies, the following mutations: K384E, N391D, N395D, S425E, Q430E, TQ436437EE, KR442443EE, T461D, and K467E (bold in the protein sequence alignment of negCry3Aa (SEQ ID NO:6) to Cry3Aa (SEQ ID NO:4) shown in FIG. 17) were engineered into the wild-type cry3aa gene, which was then used to make the final expression construct comprised of the negCry3Aa, a ribosome binding site and the supercharged GFP (scGFP), see Lawrence M S, Phillips K J, Liu DR. Supercharging proteins can impart unusual resilience. *J Am Chem Soc.* 2007; 129(33):10110-10112. This expression plasmid was then transformed into Bt cells and grown for 48 h or 72 h. Cells were harvested and the resultant crystals (NegCry3Aa-RBS-scGFP) were purified by sucrose density gradient centrifugation, followed by extensive washing in ice-cold $ddH_2O$. As shown in FIG. 18A, the NegCry3Aa-RBS-scGFP crystal pellets exhibited bright green fluorescence when imaged at the GFP excitation wavelength while no such fluorescence was observed for the control pellet. To further verify the encapsulation of scGFP in negCry3Aa, the negCry3Aa-RBS-scGFP crystal pellets were solubilized in standard SDS sample buffer and boiled for 5 min, followed by SDS-PAGE. As indicated in the SDS-PAGE gel in FIG. 18B, two major bands corresponding to negCry3Aa (theoretical MW=73.1 kDa) and scGFP (theoretical MW=28.5 kDa), respectively, can be observed.

Entrapment of lipAR9 in negCry3Aa Crystals

Figure 26:
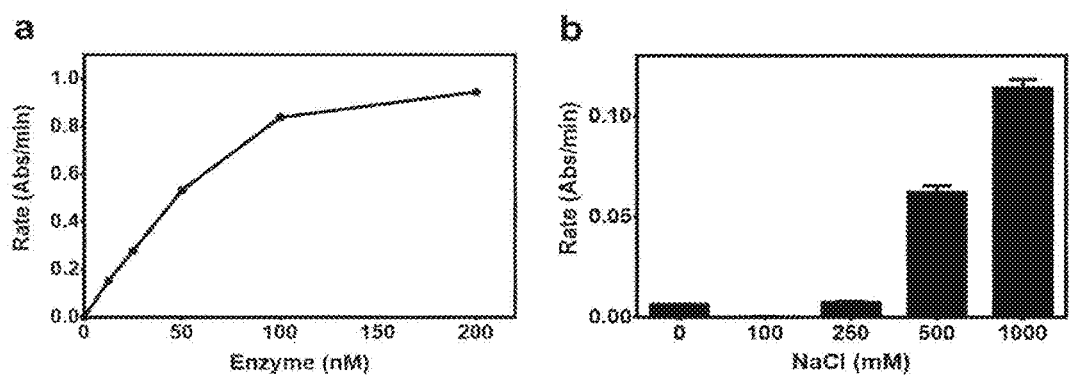
FIG. 26. Catch and release of lipAR9 by Cry3Aa crystals. (a) p-Nitrophenyl acetate hydrolysis activity of purified 3A[lipAR9] crystals. (b) Lipase activity of supernatant after release of lipAR9 protein. 3A[lipAR9] crystals were incubated with increasing concentrations of NaCl for 1 h and then removed from the mixture. The increase in lipase activity in the supernatant indicates that lipA was released as a function of NaCl concentration.

The negCry3Aa mutant also can be used to improve the loading of a lipase. When lipase A fused to polyarginine tail (lipAR9) was co-expressed with negCry3Aa the loading improved (FIG. 19).

Example 3

Cry3Aa Fusion Protein Capable of Protein-Entrapping

The present inventors have demonstrated in their previous studies that the fusion of 1-3 repeats of a 56-residue methallothionein protein having the following amino acid sequence (SEQ ID NO:8): MTSTTLVKCACEPCLCNVDPSKAIDRNGLYYCSEACADGHTGGSKGCGHTGCNCHG to the C-terminus of Cry3Aa via genetic fusion can still form fusion crystals (Cry3Aa-$[SmtA]_{1-3}$) in Bt (Sun, Q., Cheng, S W., Cheung, K., Lee, M M., Chan, M K., "Cry protein crystal-immobilized metallothioneins for bioremediation of heavy metals from water", Crystals, 2019, 9(6): 287).

The Cry3Aa-$[SmtA]_1$ construct (a fusion of SEQ ID NO:4 and SEQ ID NO:8) was then tested to reveal whether it can entrap mCherry in vivo when both coding sequences for Cry3Aa-$[SmtA]_1$ and mCherry are co-expressed in Bt. A pHT315 plasmid harboring the gene encoding sequences of the Cry3Aa-$[SmtA]_1$, a ribosome binding site, and mCherry was transformed into Bt and grown for 48-72 h. As indicated on the SDS-PAGE gel shown in FIG. 20, the extracts from 40/60% sucrose layer (lane 4) contained the Cry3Aa-$[SmtA]_1$ (MW~78 kDa) and mCherry (MW~26 kDa), thus indicating the entrapment of mCherry in Cry3Aa-$[SmtA]_1$.

Example 4

Changing the Size of Cry3Aa Channel

The size of the Cry3Aa solvent channel will influence the size of the protein (e.g., an enzyme) that can be entrapped inside the crystal. For instance, a larger protein may require more space in the channel to be accommodated without steric clash, while a smaller protein might necessitate a smaller channel to prevent its diffusion. In order to increase the size of the channel, amino acids exposed to the solvent channel (FIG. 21) would need to be removed from the Cry3Aa sequence (SEQ ID NO:4). These regions include segments 110-128, 181-197, 211-226, 250-264, 423-436, 457-471, 593-598, and 627-632 of Cry3Aa (SEQ ID NO:4). The specific amino acids that can be deleted are indicated in bold in the Cry3Aa sequence (FIG. 22) and are listed in FIG. 23.

In order to illustrate this for a potential target enzyme, COOT modeling was used to fit a sucrose phosphorylase (LmSP) homolog *Thermoanaerobacter thermosaccharolyticum* 6F-phosphate phosphorylase (PDB ID: 6S9V) in the Cry3Aa crystal channel. While the majority of LmSP can be accommodated in the crystal, several loops (colored in red) clash with the enzyme model (FIG. 24*a*). Notably, several of these regions are the same as listed in FIG. 22. One specific area that interferes with LmSP accommodation is the region from 423-436. Therefore, amino acids Gln 426, Tyr 427, Glu 433 and Ala 434 in this region were deleted from Cry3Aa to expand the channel size. When LmSP was co-expressed with this new mutant of Cry3Aa (3A2-2, SEQ ID NO:7), significantly improved entrapment of LmSP in the crystal was observed (FIG. 24*b*).

Thus, the present inventors have illustrated for the first time that modifying a Cry protein by amino acid insertions or deletions (for example, insertion of at least 1, 2, 3, 4, 5, 6, or 7 amino acid, or a deletion of at least 1, 2, 3, 4, 5, 6, or 7 amino acids) at one or more of the 8 specific regions (for example, at least 1, 2, 3, 4, 5, 6, or 7 regions) shown in FIG. 22 can effectively reduce or enlarge the protein's channel size and can therefore make the resultant crystal-forming protein to entrap a target protein (e.g., an enzyme) with higher level of efficacy, i.e., improved entrapment/retention rate and limited diffusion rate for the target protein.

Example 5

Incorporating Mutations in Cry3Aa to Stabilize the Crystal

A very important characteristic of a catalyst is its reusability. Cry3Aa crystals are inherently reusable since they are solid materials. If the crystals solubilize, however, they will release the entrapped enzyme into the bulk media. Chemical cross-linkers can be used to reduce the solubility, but this adds an additional step to catalyst production and poses environmental concerns. Taking advantage of the genetically encoded nature of the Cry3Aa crystal, a more elegant approach is to introduce stabilizing mutations at the intermolecular interfaces to generate an intrinsically insoluble crystal.

One position where is Ser 145, whose Ca atom is only 3.7 Å away from the Cα of Ser 145 of an adjacent Cry3Aa monomer, making them suitable for disulfide bond formation (FIG. 25*a*). When Ser 145 was mutated to cysteine (3AS145C) the crystal became much more resistant to solubilization at alkaline pH (FIG. 25*b*). Solubilization of the crystals in DTT confirmed disulfide bond formation. Another potential region to stabilize is His 161, which interacts with Glu 168 of a neighboring Cry3Aa monomer (FIG. 25*c*). His 161 was mutated to Arg (3AH161R) to increase the pKa of the charged residue thereby maintaining an electrostatic interaction with Glu 168 across a broader range of pH values. This mutation also reduced the solubility of the Cry3Aa crystal (FIG. 25*b*). More importantly, when a modified Cry3Aa protein containing both the S145C and H161R mutations was co-expressed with three copies of $PML^{VG}$ (3ADM$[PML^{VG}]^3$), the reusability of the catalyst was enhanced during the production of biodiesel from waste cooking oil (FIG. 25*d*), increasing the total turnover number (TTN) by 50% after 25 reaction cycles.

Example 6

Cry3Aa Crystal Entrapment for Protein Purification

It was previously demonstrated that lysozyme can bind to Cry3Aa crystals in high occupancy, but can be easily released at high salt concentration. It was later demonstrated that the highly positive charge nature of lysozyme was responsible for its binding to Cry3Aa, which has a negatively charge patch of amino acids within its crystal channels. Based on this data, it was speculated that a positively charged patch of amino acids (poly-arginine) can be fused to a protein, coexpress the fusion protein with Cry3Aa in *Bacillus thuringiensis*, capture the fusion protein in vivo by the Cry3Aa crystal, and release the fusion protein in vitro by adding NaCl. If successful, this can offer anew approach to express and purify soluble protein without the need for columns or expensive reagents. To test this hypothesis, the coding sequence for a poly-arginine tail with 9 consecutive arginine residues (R9) was fused to the coding sequence for lipase A from *Bacillus subtilis* (lipA, 19 kDa) and inserted downstream of Cry3Aa coding sequence to generate the construct 3A[lipAR9]. As expected, the purified Cry3Aa crystals contained lipAR9 as demonstrated by the high lipase activity of the resulting crystals (FIG. 26a). Notably, lipAR9 can be easily released from the crystal by addition of NaCl (FIG. 26b). These data show that not only can R9 be used as a fusion tag to encapsulate proteins and enzymes within Cry3Aa crystals, but they also confirm that the Cry3Aa platform could be implemented as a general strategy for protein purification.

All patents, patent applications, and other publications, including GenBank Accession Numbers, cited in this application are incorporated by reference in the entirety for all purposes.

SEQUENCE LISTING

<160> NUMBER OF SEQ ID NOS: 20

<210> SEQ ID NO 1
<211> LENGTH: 287
<212> TYPE: PRT
<213> ORGANISM: Artificial Sequence
<220> FEATURE:
<223> OTHER INFORMATION: Description of sequence: amino acid sequence of PML

<400> SEQUENCE: 1

Met Ser Thr Lys Tyr Pro Ile Val Leu Val His Gly Leu Ala Gly Phe
1               5                   10                  15

Asn Glu Ile Val Gly Phe Pro Tyr Phe Tyr Gly Ile Ala Asp Ala Leu
            20                  25                  30

Arg Gln Asp Gly His Gln Val Phe Thr Ala Ser Leu Ser Ala Phe Asn
        35                  40                  45

Ser Asn Glu Val Arg Gly Lys Gln Leu Trp Gln Phe Val Gln Thr Leu
    50                  55                  60

Leu Gln Glu Thr Gln Ala Lys Lys Val Asn Phe Ile Gly His Ser Gln
65                  70                  75                  80

Gly Pro Leu Ala Cys Arg Tyr Val Ala Ala Asn Tyr Pro Asp Ser Val
                85                  90                  95

Ala Ser Val Thr Ser Ile Asn Gly Val Asn His Gly Ser Glu Ile Ala
            100                 105                 110

Asp Leu Tyr Arg Arg Ile Met Arg Lys Asp Ser Ile Pro Glu Tyr Ile
        115                 120                 125

Val Glu Lys Val Leu Asn Ala Phe Gly Thr Ile Ile Ser Thr Phe Ser
    130                 135                 140

Gly His Arg Gly Asp Pro Gln Asp Ala Ile Ala Ala Leu Glu Ser Leu
145                 150                 155                 160

Thr Thr Glu Gln Val Thr Glu Phe Asn Asn Lys Tyr Pro Gln Ala Leu
                165                 170                 175

Pro Lys Thr Pro Gly Gly Glu Gly Asp Glu Ile Val Asn Gly Val His
            180                 185                 190

Tyr Tyr Cys Phe Gly Ser Tyr Ile Gln Gly Leu Ile Ala Gly Glu Lys
        195                 200                 205

Gly Asn Leu Leu Asp Pro Thr His Ala Ala Met Arg Val Leu Asn Thr
    210                 215                 220

Phe Phe Thr Glu Lys Gln Asn Asp Gly Leu Val Gly Arg Ser Ser Met
225                 230                 235                 240

Arg Leu Gly Lys Leu Ile Lys Asp Asp Tyr Ala Gln Asp His Ile Asp
                245                 250                 255

Met Val Asn Gln Val Ala Gly Leu Val Gly Tyr Asn Glu Asp Ile Val
            260                 265                 270

Ala Ile Tyr Thr Gln His Ala Lys Tyr Leu Ala Ser Lys Gln Leu
        275                 280                 285

<210> SEQ ID NO 2

```
<211> LENGTH: 287
<212> TYPE: PRT
<213> ORGANISM: Artificial Sequence
<220> FEATURE:
<223> OTHER INFORMATION: Description of sequence: amino acid sequence of
      PML VG

<400> SEQUENCE: 2

Met Ser Thr Lys Tyr Pro Ile Val Leu Val His Gly Leu Ala Gly Phe
1               5                   10                  15

Asn Glu Ile Val Gly Phe Pro Tyr Phe Tyr Gly Ile Ala Asp Ala Leu
            20                  25                  30

Arg Gln Asp Gly His Gln Val Phe Thr Ala Ser Leu Ser Ala Phe Asn
        35                  40                  45

Ser Asn Glu Val Arg Gly Lys Gln Leu Trp Gln Phe Val Gln Thr Leu
50                  55                  60

Leu Gln Glu Thr Gln Ala Lys Lys Val Asn Phe Ile Gly His Ser Gln
65                  70                  75                  80

Gly Pro Leu Ala Cys Arg Tyr Val Ala Ala Asn Tyr Pro Asp Ser Val
                85                  90                  95

Ala Ser Val Thr Ser Ile Asn Gly Val Asn His Gly Ser Glu Ile Ala
            100                 105                 110

Asp Leu Tyr Arg Arg Val Met Arg Lys Asp Ser Ile Pro Glu Tyr Ile
        115                 120                 125

Val Gly Lys Val Leu Asn Ala Phe Gly Thr Ile Ile Ser Thr Phe Ser
130                 135                 140

Gly His Arg Gly Asp Pro Gln Asp Ala Ile Ala Ala Leu Glu Ser Leu
145                 150                 155                 160

Thr Thr Glu Gln Val Thr Glu Phe Asn Asn Lys Tyr Pro Gln Ala Leu
                165                 170                 175

Pro Lys Thr Pro Gly Gly Gly Asp Glu Ile Val Asn Gly Val His
            180                 185                 190

Tyr Tyr Cys Phe Gly Ser Tyr Ile Gln Gly Leu Ile Ala Gly Glu Lys
        195                 200                 205

Gly Asn Leu Leu Asp Pro Thr His Ala Ala Met Arg Val Leu Asn Thr
210                 215                 220

Phe Phe Thr Glu Lys Gln Asn Asp Gly Leu Val Gly Arg Ser Ser Met
225                 230                 235                 240

Arg Leu Gly Lys Leu Ile Lys Asp Asp Tyr Ala Gln Asp His Ile Asp
                245                 250                 255

Met Val Asn Gln Val Ala Gly Leu Val Gly Tyr Asn Glu Asp Ile Val
            260                 265                 270

Ala Ile Tyr Thr Gln His Ala Lys Tyr Leu Ala Ser Lys Gln Leu
        275                 280                 285

<210> SEQ ID NO 3
<211> LENGTH: 492
<212> TYPE: PRT
<213> ORGANISM: Artificial Sequence
<220> FEATURE:
<223> OTHER INFORMATION: Description of sequence: amino acid sequence of
      LmSP

<400> SEQUENCE: 3

Met Glu Ile Gln Asn Lys Ala Met Leu Ile Thr Tyr Ala Asp Ser Leu
1               5                   10                  15

Gly Lys Asn Leu Lys Asp Val His Gln Val Leu Lys Glu Asp Ile Gly
            20                  25                  30
```

```
Asp Ala Ile Gly Gly Val His Leu Leu Pro Phe Phe Pro Ser Thr Gly
        35                  40                  45

Asp Arg Gly Phe Ala Pro Ala Asp Tyr Thr Arg Val Asp Ala Ala Phe
    50                  55                  60

Gly Asp Trp Ala Asp Val Glu Ala Leu Gly Glu Tyr Tyr Leu Met
65                  70                  75                  80

Phe Asp Phe Met Ile Asn His Ile Ser Arg Glu Ser Val Met Tyr Gln
                85                  90                  95

Asp Phe Lys Lys Asn His Asp Asp Ser Lys Tyr Lys Asp Phe Phe Ile
            100                 105                 110

Arg Trp Glu Lys Phe Trp Ala Lys Ala Gly Glu Asn Arg Pro Thr Gln
            115                 120                 125

Ala Asp Val Asp Leu Ile Tyr Lys Arg Lys Asp Lys Ala Pro Thr Gln
        130                 135                 140

Glu Ile Thr Phe Asp Asp Gly Thr Thr Glu Asn Leu Trp Asn Thr Phe
145                 150                 155                 160

Gly Glu Glu Gln Ile Asp Ile Asp Val Asn Ser Ala Ile Ala Lys Glu
                165                 170                 175

Phe Ile Lys Thr Thr Leu Glu Asp Met Val Lys His Gly Ala Asn Leu
            180                 185                 190

Ile Arg Leu Asp Ala Phe Ala Tyr Ala Val Lys Lys Val Asp Thr Asn
        195                 200                 205

Asp Phe Phe Val Glu Pro Glu Ile Trp Asp Thr Leu Asn Glu Val Arg
    210                 215                 220

Glu Ile Leu Thr Pro Leu Lys Ala Glu Ile Leu Pro Glu Ile His Glu
225                 230                 235                 240

His Tyr Ser Ile Pro Lys Lys Ile Asn Asp His Gly Tyr Phe Thr Tyr
                245                 250                 255

Asp Phe Ala Leu Pro Met Thr Thr Leu Tyr Thr Leu Tyr Ser Gly Lys
            260                 265                 270

Thr Asn Gln Leu Ala Lys Trp Leu Lys Met Ser Pro Met Lys Gln Phe
        275                 280                 285

Thr Thr Leu Asp Thr His Asp Gly Ile Gly Val Val Asp Ala Arg Asp
290                 295                 300

Ile Leu Thr Asp Asp Glu Ile Asp Tyr Ala Ser Glu Gln Leu Tyr Lys
305                 310                 315                 320

Val Gly Ala Asn Val Lys Lys Thr Tyr Ser Ser Ala Ser Tyr Asn Asn
                325                 330                 335

Leu Asp Ile Tyr Gln Ile Asn Ser Thr Tyr Tyr Ser Ala Leu Gly Asn
            340                 345                 350

Asp Asp Ala Ala Tyr Leu Leu Ser Arg Val Phe Gln Val Phe Ala Pro
        355                 360                 365

Gly Ile Pro Gln Ile Tyr Tyr Val Gly Leu Leu Ala Gly Glu Asn Asp
    370                 375                 380

Ile Ala Leu Leu Glu Ser Thr Lys Glu Gly Arg Asn Ile Asn Arg His
385                 390                 395                 400

Tyr Tyr Thr Arg Glu Glu Val Lys Ser Glu Val Lys Arg Pro Val Val
                405                 410                 415

Ala Asn Leu Leu Lys Leu Leu Ser Trp Arg Asn Glu Ser Pro Ala Phe
            420                 425                 430

Asp Leu Ala Gly Ser Ile Thr Val Asp Thr Pro Thr Asp Thr Thr Ile
        435                 440                 445
```

```
Val Val Thr Arg Gln Asp Glu Asn Gly Gln Asn Lys Ala Val Leu Thr
    450                 455                 460

Ala Asp Ala Ala Asn Lys Thr Phe Glu Ile Val Glu Asn Gly Gln Thr
465                 470                 475                 480

Val Met Ser Ser Asp Asn Leu Thr Gln Asn Leu Glu
                485                 490

<210> SEQ ID NO 4
<211> LENGTH: 644
<212> TYPE: PRT
<213> ORGANISM: Artificial Sequence
<220> FEATURE:
<223> OTHER INFORMATION: Description of sequence: amino acid sequence of
      Cry3Aa

<400> SEQUENCE: 4

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
                20                  25                  30

Pro Asn Pro Thr Leu Glu Asp Leu Asn Tyr Lys Glu Phe Leu Arg Met
            35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Gly Tyr Gly Thr Thr
305                 310                 315                 320
```

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
    370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 5
<211> LENGTH: 625
<212> TYPE: PRT
<213> ORGANISM: Artificial Sequence
<220> FEATURE:
<223> OTHER INFORMATION: Description of sequence: amino acid sequence of
      Cry3Aa(1-625) (Cry3Aa*)

<400> SEQUENCE: 5

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
                20                  25                  30

```
Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
                100                 105                 110

Val Glu Ala Leu Met Asp Gln Lys Ile Ala Asp Tyr Ala Lys Asn Lys
            115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
                180                 185                 190

Phe Leu Thr Thr Tyr Ala Gln Ala Ala Asn Thr His Leu Phe Leu Leu
            195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
                260                 265                 270

Thr Leu Thr Val Leu Asp Leu Ile Ala Leu Phe Pro Leu Tyr Asp Val
            275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
                340                 345                 350

Asn Asp Ser Phe Asn Tyr Trp Ser Gly Asn Tyr Val Ser Thr Arg Pro
            355                 360                 365

Ser Ile Gly Ser Asn Asp Ile Ile Thr Ser Pro Phe Tyr Gly Asn Lys
370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
    435                 440                 445
```

```
Ser Trp Asp Ser Ile Asp Gln Leu Pro Pro Glu Thr Thr Asp Glu Pro
450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
            485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
            515                 520                 525

Gly Pro Arg Phe Thr Gly Gly Asp Ile Ile Gln Cys Thr Glu Asn Gly
        530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
            595                 600                 605

Phe Ser Thr Pro Phe Glu Leu Ser Gly Asn Asn Leu Gln Ile Gly Val
            610                 615                 620

Thr
625

<210> SEQ ID NO 6
<211> LENGTH: 644
<212> TYPE: PRT
<213> ORGANISM: Artificial Sequence
<220> FEATURE:
<223> OTHER INFORMATION: Description of sequence: amino acid sequence of
      negCry3Aa

<400> SEQUENCE: 6

Met Asn Pro Asn Asn Arg Ser Glu His Asp Thr Ile Lys Thr Thr Glu
1               5                   10                  15

Asn Asn Glu Val P

```
Phe Arg Asn Ser Met Pro Ser Phe Ala Ile Ser Gly Tyr Glu Val Leu
            180                 185                 190

Phe Leu Thr Thr Tyr Ala Gln Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Glu
    370                 375                 380

Ser Ser Glu Pro Val Gln Asp Leu Glu Phe Asp Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Glu Gln Tyr Asn Asp Glu Thr Asp
            420                 425                 430

Glu Ala Ser Glu Glu Thr Tyr Asp Ser Glu Glu Asn Val Gly Ala Val
        435                 440                 445

Ser Trp Asp Ser Ile Asp Gln Leu Pro Pro Glu Thr Asp Asp Glu Pro
    450                 455                 460

Leu Glu Glu Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590
```

```
Ile Asn Lys Gly Asp Thr Leu Thr Tyr Asn Ser Phe Asn Leu Ala Ser
            595                 600                 605

Phe Ser Thr Pro Phe Glu Leu Ser Gly Asn Asn Leu Gln Ile Gly Val
610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 7
<211> LENGTH: 640
<212> TYPE: PRT
<213> ORGANISM: Artificial Sequence
<220> FEATURE:
<223> OTHER INFORMATION: Description of sequence: amino acid sequence of
      3A2-2

<400> SEQUENCE: 7

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
                20                  25                  30

Pro Asn Pro Thr Leu Glu Asp Leu Asn Tyr Lys Glu Phe Leu Arg Met
            35                  40                  45

Thr Ala Asp Asn Asn Thr Glu Ala Leu Asp Ser Ser Thr Thr Lys Asp
50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300
```

```
Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Asn Asp Gln Thr Asp Ser Thr
                420                 425                 430

Gln Thr Tyr Asp Ser Lys Arg Asn Val Gly Ala Val Ser Trp Asp Ser
            435                 440                 445

Ile Asp Gln Leu Pro Pro Glu Thr Thr Asp Glu Pro Leu Glu Lys Gly
450                 455                 460

Tyr Ser His Gln Leu Asn Tyr Val Met Cys Phe Leu Met Gln Gly Ser
465                 470                 475                 480

Arg Gly Thr Ile Pro Val Leu Thr Trp Thr His Lys Ser Val Asp Phe
                485                 490                 495

Phe Asn Met Ile Asp Ser Lys Lys Ile Thr Gln Leu Pro Leu Val Lys
                500                 505                 510

Ala Tyr Lys Leu Gln Ser Gly Ala Ser Val Val Ala Gly Pro Arg Phe
            515                 520                 525

Thr Gly Gly Asp Ile Ile Gln Cys Thr Glu Asn Gly Ser Ala Ala Thr
530                 535                 540

Ile Tyr Val Thr Pro Asp Val Ser Tyr Ser Gln Lys Tyr Arg Ala Arg
545                 550                 555                 560

Ile His Tyr Ala Ser Thr Ser Gln Ile Thr Phe Thr Leu Ser Leu Asp
                565                 570                 575

Gly Ala Pro Phe Asn Gln Tyr Tyr Phe Asp Lys Thr Ile Asn Lys Gly
            580                 585                 590

Asp Thr Leu Thr Tyr Asn Ser Phe Asn Leu Ala Ser Phe Ser Thr Pro
                595                 600                 605

Phe Glu Leu Ser Gly Asn Asn Leu Gln Ile Gly Val Thr Gly Leu Ser
            610                 615                 620

Ala Gly Asp Lys Val Tyr Ile Asp Lys Ile Glu Phe Ile Pro Val Asn
625                 630                 635                 640

<210> SEQ ID NO 8
<211> LENGTH: 56
<212> TYPE: PRT
<213> ORGANISM: Artificial Sequence
<220> FEATURE:
<223> OTHER INFORMATION: Description of sequence: amino acid sequence of
      methallothionein protein

<400> SEQUENCE: 8

Met Thr Ser Thr Thr Leu Val Lys Cys Ala Cys Glu Pro Cys Leu Cys
1               5                   10                  15

Asn Val Asp Pro Ser Lys Ala Ile Asp Arg Asn Gly Leu Tyr Tyr Cys
                20                  25                  30
```

```
Ser Glu Ala Cys Ala Asp Gly His Thr Gly Gly Ser Lys Gly Cys Gly
        35                  40                  45

His Thr Gly Cys Asn Cys His Gly
    50                  55

<210> SEQ ID NO 9
<211> LENGTH: 644
<212> TYPE: PRT
<213> ORGANISM: Artificial Sequence
<220> FEATURE:
<223> OTHER INFORMATION: Description of sequence: amino acid sequence of
      Cry3Aa double mutant (S145C, H161R)

<400> SEQUENCE: 9

Met Asn Pro Asn Asn Arg Ser Glu His Asp Thr Ile Lys Thr Thr Glu
1               5                   10                  15

Asn Asn Glu Val Pro Thr Asn His Val Gln Tyr P

```
                325                 330                 335
Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
    370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 10
<211> LENGTH: 182
<212> TYPE: PRT
<213> ORGANISM: Artificial Sequence
<220> FEATURE:
<223> OTHER INFORMATION: Description of sequence: amino acid sequence of
      lipA

<400> SEQUENCE: 10

Met Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
            20                  25                  30

Ser Arg Asp Lys Leu Tyr Ala Val Asp Phe Trp Asp Lys Thr Gly Thr
```

```
                35                  40                  45
Asn Tyr Asn Asn Gly Pro Val Leu Ser Arg Phe Val Gln Lys Val Leu
 50                  55                  60

Asp Glu Thr Gly Ala Lys Lys Val Asp Ile Val Ala His Ser Met Gly
 65                  70                  75                  80

Gly Ala Asn Thr Leu Tyr Tyr Ile Lys Asn Leu Asp Gly Gly Asn Lys
                 85                  90                  95

Val Ala Asn Val Val Thr Val Gly Gly Ala Asn Arg Leu Thr Thr Gly
                100                 105                 110

Lys Ala Leu Pro Gly Thr Asp Pro Asn Gln Lys Ile Leu Tyr Thr Ser
                115                 120                 125

Ile Tyr Ser Ser Ala Asp Met Ile Val Met Asn Tyr Leu Ser Arg Leu
    130                 135                 140

Asp Gly Ala Arg Asn Val Gln Ile His Gly Val Gly His Ile Gly Leu
145                 150                 155                 160

Leu Tyr Ser Ser Gln Val Asn Ser Leu Ile Lys Glu Gly Leu Asn Gly
                165                 170                 175

Gly Gly Gln Asn Thr Asn
                180

<210> SEQ ID NO 11
<211> LENGTH: 195
<212> TYPE: PRT
<213> ORGANISM: Artificial Sequence
<220> FEATURE:
<223> OTHER INFORMATION: Description of sequence: amino acid sequence of
      lipAR9

<400> SEQUENCE: 11

Met Ala Glu His Asn Pro Val Val Met Val His Gly Ile Gly Gly Ala
 1               5                  10                  15

Ser Phe Asn Phe Ala Gly Ile Lys Ser Tyr Leu Val Ser Gln Gly Trp
                 20                  25                  30

Ser Arg Asp Lys Leu Tyr Ala Val Asp Phe Trp Asp Lys Thr Gly Thr
            35                  40                  45

Asn Tyr Asn Asn Gly Pro Val Leu Ser Arg Phe Val Gln Lys Val Leu
 50                  55                  60

Asp Glu Thr Gly Ala Lys Lys Val Asp Ile Val Ala His Ser Met Gly
 65                  70                  75                  80

Gly Ala Asn Thr Leu Tyr Tyr Ile Lys Asn Leu Asp Gly Gly Asn Lys
                 85                  90                  95

Val Ala Asn Val Val Thr Val Gly Gly Ala Asn Arg Leu Thr Thr Gly
                100                 105                 110

Lys Ala Leu Pro Gly Thr Asp Pro Asn Gln Lys Ile Leu Tyr Thr Ser
                115                 120                 125

Ile Tyr Ser Ser Ala Asp Met Ile Val Met Asn Tyr Leu Ser Arg Leu
    130                 135                 140

Asp Gly Ala Arg Asn Val Gln Ile His Gly Val Gly His Ile Gly Leu
145                 150                 155                 160

Leu Tyr Ser Ser Gln Val Asn Ser Leu Ile Lys Glu Gly Leu Asn Gly
                165                 170                 175

Gly Gly Gln Asn Thr Asn Gly Ser Ser Gly Arg Arg Arg Arg Arg
                180                 185                 190

Arg Arg Arg
    195
```

```
<210> SEQ ID NO 12
<211> LENGTH: 633
<212> TYPE: PRT
<213> ORGANISM: Artificial Sequence
<220> FEATURE:
<223> OTHER INFORMATION: Description of sequence: consensus sequence
      from Fig. 17

<400> SEQUENCE: 12

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365
```

-continued

Ser Ile Gly Ser Asn Asp Ile Ile Thr Ser Pro Phe Tyr Gly Asn Ser
            370                 375                 380

Ser Glu Pro Val Gln Leu Glu Phe Gly Glu Lys Val Tyr Arg Ala Val
385                 390                 395                 400

Ala Asn Thr Asn Leu Ala Val Trp Pro Ser Ala Val Tyr Ser Gly Val
            405                 410                 415

Thr Lys Val Glu Phe Gln Tyr Asn Asp Thr Asp Glu Ala Ser Thr Tyr
            420                 425                 430

Asp Ser Asn Val Gly Ala Val Ser Trp Asp Ser Ile Asp Gln Leu Pro
            435                 440                 445

Pro Glu Thr Asp Glu Pro Leu Glu Gly Tyr Ser His Gln Leu Asn Tyr
            450                 455                 460

Val Met Cys Phe Leu Met Gln Gly Ser Arg Gly Thr Ile Pro Val Leu
465                 470                 475                 480

Thr Trp Thr His Lys Ser Val Asp Phe Phe Asn Met Ile Asp Ser Lys
            485                 490                 495

Lys Ile Thr Gln Leu Pro Leu Val Lys Ala Tyr Lys Leu Gln Ser Gly
            500                 505                 510

Ala Ser Val Val Ala Gly Pro Arg Phe Thr Gly Gly Asp Ile Ile Gln
            515                 520                 525

Cys Thr Glu Asn Gly Ser Ala Ala Thr Ile Tyr Val Thr Pro Asp Val
530                 535                 540

Ser Tyr Ser Gln Lys Tyr Arg Ala Arg Ile His Tyr Ala Ser Thr Ser
545                 550                 555                 560

Gln Ile Thr Phe Thr Leu Ser Leu Asp Gly Ala Pro Phe Asn Gln Tyr
            565                 570                 575

Tyr Phe Asp Lys Thr Ile Asn Lys Gly Asp Thr Leu Thr Tyr Asn Ser
            580                 585                 590

Phe Asn Leu Ala Ser Phe Ser Thr Pro Phe Glu Leu Ser Gly Asn Asn
            595                 600                 605

Leu Gln Ile Gly Val Thr Gly Leu Ser Ala Gly Asp Lys Val Tyr Ile
            610                 615                 620

Asp Lys Ile Glu Phe Ile Pro Val Asn
625                 630

<210> SEQ ID NO 13
<211> LENGTH: 1176
<212> TYPE: PRT
<213> ORGANISM: Bacillus thuringiensis
<220> FEATURE:
<223> OTHER INFORMATION: Description of sequence: protein Cry1Aa from
      Fig. 27

<400> SEQUENCE: 13

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Pro Val Gln Ile
65                  70                  75                  80

Glu Gln Leu Ile Asn Gln Arg Ile Glu Glu Phe Ala Arg Asn Gln Ala

```
            85                  90                  95
Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
            130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                    165                 170                 175

Val Phe Gly Gln Arg Trp Gly Phe Asp Ala Ala Thr Ile Asn Ser Arg
                    180                 185                 190

Tyr Asn Asp Leu Thr Arg Leu Ile Gly Asn Tyr Thr Asp Tyr Ala Val
                    195                 200                 205

Arg Trp Tyr Asn Thr Gly Leu Glu Arg Val Trp Gly Pro Asp Ser Arg
            210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                    245                 250                 255

Ile Arg Thr Val Ser Gln Leu Thr Arg Glu Ile Tyr Thr Asn Pro Val
                    260                 265                 270

Leu Glu Asn Phe Asp Gly Ser Phe Arg Gly Met Ala Gln Arg Ile Glu
            275                 280                 285

Gln Asn Ile Arg Gln Pro His Leu Met Asp Ile Leu Asn Ser Ile Thr
            290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                    325                 330                 335

Leu Phe Gly Asn Ala Gly Asn Ala Ala Pro Pro Val Leu Val Ser Leu
                    340                 345                 350

Thr Gly Leu Gly Ile Phe Arg Thr Leu Ser Ser Pro Leu Tyr Arg Arg
            355                 360                 365

Ile Ile Leu Gly Ser Gly Pro Asn Asn Gln Glu Leu Phe Val Leu Asp
            370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                    405                 410                 415

Gln Asp Asn Ser Val Pro Pro Arg Ala Gly Phe Ser His Arg Leu Ser
                    420                 425                 430

His Val Thr Met Leu Ser Gln Ala Ala Gly Ala Val Tyr Thr Leu Arg
                    435                 440                 445

Ala Pro Thr Phe Ser Trp Gln His Arg Ser Ala Glu Phe Asn Asn Ile
            450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                    485                 490                 495

Asp Ile Leu Arg Arg Thr Ser Pro Gly Gln Ile Ser Thr Leu Arg Val
                    500                 505                 510
```

```
Asn Ile Thr Ala Pro Leu Ser Gln Arg Tyr Arg Val Arg Ile Arg Tyr
            515                 520                 525

Ala Ser Thr Thr Asn Leu Gln Phe His Thr Ser Ile Asp Gly Arg Pro
            530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
            595                 600                 605

Thr Phe Glu Ala Glu Tyr Asp Leu Glu Arg Ala Gln Lys Ala Val Asn
            610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
                660                 665                 670

Ala Lys Arg Leu Ser Asp Glu Arg Asn Leu Leu Gln Asp Pro Asn Phe
            675                 680                 685

Arg Gly Ile Asn Arg Gln Leu Asp Arg Gly Trp Arg Gly Ser Thr Asp
            690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
                740                 745                 750

Tyr Ile Glu Asp Ser Gln Asp Leu Glu Ile Tyr Leu Ile Arg Tyr Asn
            755                 760                 765

Ala Lys His Glu Thr Val Asn Val Pro Gly Thr Gly Ser Leu Trp Pro
            770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815

Gly Glu Lys Cys Ala His His Ser His His Phe Ser Leu Asp Ile Asp
                820                 825                 830

Val Gly Cys Thr Asp Leu Asn Glu Asp Leu Gly Val Trp Val Ile Phe
            835                 840                 845

Lys Ile Lys Thr Gln Asp Gly His Ala Arg Leu Gly Asn Leu Glu Phe
850                 855                 860

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

Asn Ser Gln Tyr Asp Gln Leu Gln Ala Asp Thr Asn Ile Ala Met Ile
            915                 920                 925
```

```
His Ala Ala Asp Lys Arg Val His Ser Ile Arg Glu Ala Tyr Leu Pro
    930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
            980                 985                 990

Gly His Val Asp Val Glu Glu Gln Asn Asn Gln Arg Ser Val Leu Val
        995                 1000                1005

Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly
    1025                1030                1035

Tyr Gly Glu Gly Cys Val Thr Ile His Glu Ile Glu Asn Asn Thr
    1040                1045                1050

Asp Glu Leu Lys Phe Ser Asn Cys Val Glu Glu Ile Tyr Pro
    1055                1060                1065

Asn Asn Thr Val Thr Cys Asn Asp Tyr Thr Val Asn Gln Glu Glu
    1070                1075                1080

Tyr Gly Gly Ala Tyr Thr Ser Arg Asn Arg Gly Tyr Asn Glu Ala
    1085                1090                1095

Pro Ser Val Pro Ala Asp Tyr Ala Ser Val Tyr Glu Glu Lys Ser
    1100                1105                1110

Tyr Thr Asp Gly Arg Arg Glu Asn Pro Cys Glu Phe Asn Arg Gly
    1115                1120                1125

Tyr Arg Asp Tyr Thr Pro Leu Pro Val Gly Tyr Val Thr Lys Glu
    1130                1135                1140

Leu Glu Tyr Phe Pro Glu Thr Asp Lys Val Trp Ile Glu Ile Gly
    1145                1150                1155

Glu Thr Glu Gly Thr Phe Ile Val Asp Ser Val Glu Leu Leu Leu
    1160                1165                1170

Met Glu Glu
    1175

<210> SEQ ID NO 14
<211> LENGTH: 633
<212> TYPE: PRT
<213> ORGANISM: Bacillus thuringiensis
<220> FEATURE:
<223> OTHER INFORMATION: Description of sequence: protein Cry2A -continued Thr Glu Gln Phe Leu Asn Gln Arg Leu Asn Thr Asp Thr Leu Ala Arg
            100                 105                 110

Val Asn Ala Glu Leu Ile Gly Leu Gln Ala Asn Ile Arg Glu Phe Asn
            115                 120                 125

Gln Gln Val Asp Asn Phe Leu Asn Pro Thr Gln Asn Pro Val Pro Leu
        130                 135                 140

Ser Ile Thr Ser Ser Val Asn Thr Met Gln Gln Leu Phe Leu Asn Arg
145                 150                 155                 160

Leu Pro Gln Phe Gln Ile Gln Gly Tyr Gln Leu Leu Leu Pro Leu
                165                 170                 175

Phe Ala Gln Ala Ala Asn Met His Leu Ser Phe Ile Arg Asp Val Ile
                180                 185                 190

Leu Asn Ala Asp Glu Trp Gly Ile Ser Ala Ala Thr Leu Arg Thr Tyr
            195                 200                 205

Arg Asp Tyr Leu Arg Asn Tyr Thr Arg Asp Tyr Ser Asn Tyr Cys Ile
            210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Met Val Ser Ser Gly
            260                 265                 270

Ala Asn Leu Tyr Ala Ser Gly Ser Gly Pro Gln Gln Thr Gln Ser Phe
            275                 280                 285

Thr Ala Gln Asn Trp Pro Phe Leu Tyr Ser Leu Phe Gln Val Asn Ser
        290                 295                 300

Asn Tyr Ile Leu Ser Gly Ile Ser Gly Thr Arg Leu Ser Ile Thr Phe
305                 310                 315                 320

Pro Asn Ile Gly Gly Leu Pro Gly Ser Thr Thr Thr His Ser Leu Asn
                325                 330                 335

Ser Ala Arg Val Asn Tyr Ser Gly Gly Val Ser Ser Gly Leu Ile Gly
            340                 345                 350

Ala Thr Asn Leu Asn His Asn Phe Asn Cys Ser Thr Val Leu Pro Pro
            355                 360                 365

Leu Ser Thr Pro Phe Val Arg Ser Trp Leu Asp Ser Gly Thr Asp Arg
370                 375                 380

Glu Gly Val Ala Thr Ser Thr Asn Trp Gln Thr Glu Ser Phe Gln Thr
385                 390                 395                 400

Thr Leu Ser Leu Arg Cys Gly Ala Phe Ser Ala Arg Gly Asn Ser Asn
                405                 410                 415

Tyr Phe Pro Asp Tyr Phe Ile Arg Asn Ile Ser Gly Val Pro Leu Val
            420                 425                 430

Ile Arg Asn Glu Asp Leu Thr Arg Pro Leu His Tyr Asn Gln Ile Arg
        435                 440                 445

Asn Ile Glu Ser Pro Ser Gly Thr Pro Gly Gly Ala Arg Ala Tyr Leu
            450                 455                 460

Val Ser Val His Asn Arg Lys Asn Asn Ile Tyr Ala Ala Asn Glu Asn
465                 470                 475                 480

Gly Thr Met Ile His Leu Ala Pro Glu Asp Tyr Thr Gly Phe Thr Ile
                485                 490                 495

Ser Pro Ile His Ala Thr Gln Val Asn Asn Gln Thr Arg Thr Phe Ile
            500                 505                 510

```
Ser Glu Lys Phe Gly Asn Gln Gly Asp Ser Leu Arg Phe Glu Gln Ser
        515                 520                 525

Asn Thr Thr Ala Arg Tyr Thr Leu Arg Gly Asn Gly Asn Ser Tyr Asn
    530                 535                 540

Leu Tyr Leu Arg Val Ser Ser Ile Gly Asn Ser Thr Ile Arg Val Thr
545                 550                 555                 560

Ile Asn Gly Arg Val Tyr Thr Val Ser Asn Val Asn Thr Thr Thr Asn
                565                 570                 575

Asn Asp Gly Val Asn Asp Asn Gly Ala Arg Phe Ser Asp Ile Asn Ile
                580                 585                 590

Gly Asn Ile Val Ala Ser Asp Asn Thr Asn Val Thr Leu Asp Ile Asn
                595                 600                 605

Val Thr Leu Asn Ser Gly Thr Pro Phe Asp Leu Met Asn Ile Met Phe
            610                 615                 620

Val Pro Thr Asn Leu Pro Pro Leu Tyr
625                 630

<210> SEQ ID NO 15
<211> LENGTH: 1180
<212> TYPE: PRT
<213> ORGANISM: Bacillus thuringiensis
<220> FEATURE:
<223> OTHER INFORMATION: Description of sequence: protein Cry4Aa from
      Fig. 27

<400> SEQUENCE: 15

Met Asn Pro Tyr Gln Asn Lys Asn Glu Tyr Glu Thr Leu Asn Ala Ser
1               5                   10                  15

Gln Lys Lys Leu Asn Ile Ser Asn Asn Tyr Thr Arg Tyr Pro Ile Glu
            20                  25                  30

Asn Ser Pro Lys Gln Leu Leu Gln Ser Thr Asn Tyr Lys Asp Trp Leu
        35                  40                  45

Asn Met Cys Gln Gln Asn Gln Gln Tyr Gly Gly Asp Phe Glu Thr Phe
    50                  55                  60

Ile Asp Ser Gly Glu Leu Ser Ala Tyr Thr Ile Val Val Gly Thr Val
65                  70                  75                  80

Leu Thr Gly Phe Gly Phe Thr Thr Pro Leu Gly Leu Ala Leu Ile Gly
                85                  90                  95

Phe Gly Thr Leu Ile Pro Val Leu Phe Pro Ala Gln Asp Gln Ser Asn
            100                 105                 110

Thr Trp Ser Asp Phe Ile Thr Gln Thr Lys Asn Ile Ile Lys Lys Glu
        115                 120                 125

Ile Ala Ser Thr Tyr Ile Ser Asn Ala Asn Lys Ile Leu Asn Arg Ser
    130                 135                 140

Phe Asn Val Ile Ser Thr Tyr His Asn His Leu Lys Thr Trp Glu Asn
145                 150                 155                 160

Asn Pro Asn Pro Gln Asn Thr Gln Asp Val Arg Thr Gln Ile Gln Leu
                165                 170                 175

Val His Tyr His Phe Gln Asn Val Ile Pro Glu Leu Val Asn Ser Cys
            180                 185                 190

Pro Pro Asn Pro Ser Asp Cys Asp Tyr Tyr Asn Ile Leu Val Leu Ser
        195                 200                 205

Ser Tyr Ala Gln Ala Ala Asn Leu His Leu Thr Val Leu Asn Gln Ala
    210                 215                 220

Val Lys Phe Glu Ala Tyr Leu Lys Asn Asn Arg Gln Phe Asp Tyr Leu
225                 230                 235                 240
```

```
Glu Pro Leu Pro Thr Ala Ile Asp Tyr Tyr Pro Val Leu Thr Lys Ala
                245                 250                 255

Ile Glu Asp Tyr Thr Asn Tyr Cys Val Thr Thr Tyr Lys Lys Gly Leu
                260                 265                 270

Asn Leu Ile Lys Thr Thr Pro Asp Ser Asn Leu Asp Gly Asn Ile Asn
                275                 280                 285

Trp Asn Thr Tyr Asn Thr Tyr Arg Thr Lys Met Thr Thr Ala Val Leu
            290                 295                 300

Asp Leu Val Ala Leu Phe Pro Asn Tyr Asp Val Gly Lys Tyr Pro Ile
305                 310                 315                 320

Gly Val Gln Ser Glu Leu Thr Arg Glu Ile Tyr Gln Val Leu Asn Phe
                325                 330                 335

Glu Glu Ser Pro Tyr Lys Tyr Asp Phe Gln Tyr Gln Glu Asp Ser
                340                 345                 350

Leu Thr Arg Arg Pro His Leu Phe Thr Trp Leu Asp Ser Leu Asn Phe
                355                 360                 365

Tyr Glu Lys Ala Gln Thr Thr Pro Asn Asn Phe Phe Thr Ser His Tyr
            370                 375                 380

Asn Met Phe His Tyr Thr Leu Asp Asn Ile Ser Gln Lys Ser Ser Val
385                 390                 395                 400

Phe Gly Asn His Asn Val Thr Asp Lys Leu Lys Ser Leu Gly Leu Ala
                405                 410                 415

Thr Asn Ile Tyr Ile Phe Leu Leu Asn Val Ile Ser Leu Asp Asn Lys
                420                 425                 430

Tyr Leu Asn Asp Tyr Asn Asn Ile Ser Lys Met Asp Phe Phe Ile Thr
            435                 440                 445

Asn Gly Thr Arg Leu Leu Glu Lys Glu Leu Thr Ala Gly Ser Gly Gln
450                 455                 460

Ile Thr Tyr Asp Val Asn Lys Asn Ile Phe Gly Leu Pro Ile Leu Lys
465                 470                 475                 480

Arg Arg Glu Asn Gln Gly Asn Pro Thr Leu Phe Pro Thr Tyr Asp Asn
                485                 490                 495

Tyr Ser His Ile Leu Ser Phe Ile Lys Ser Leu Ser Ile Pro Ala Thr
                500                 505                 510

Tyr Lys Thr Gln Val Tyr Thr Phe Ala Trp Thr His Ser Ser Val Asp
                515                 520                 525

Pro Lys Asn Thr Ile Tyr Thr His Leu Thr Thr Gln Ile Pro Ala Val
            530                 535                 540

Lys Ala Asn Ser Leu Gly Thr Ala Ser Lys Val Val Gln Gly Pro Gly
545                 550                 555                 560

His Thr Gly Gly Asp Leu Ile Asp Phe Lys Asp His Phe Lys Ile Thr
                565                 570                 575

Cys Gln His Ser Asn Phe Gln Gln Ser Tyr Phe Ile Arg Ile Arg Tyr
                580                 585                 590

Ala Ser Asn Gly Ser Ala Asn Thr Arg Ala Val Ile Asn Leu Ser Ile
                595                 600                 605

Pro Gly Val Ala Glu Leu Gly Met Ala Leu Asn Pro Thr Phe Ser Gly
                610                 615                 620

Thr Asp Tyr Thr Asn Leu Lys Tyr Lys Asp Phe Gln Tyr Leu Glu Phe
625                 630                 635                 640

Ser Asn Glu Val Lys Phe Ala Pro Asn Gln Asn Ile Ser Leu Val Phe
                645                 650                 655
```

-continued

Asn Arg Ser Asp Val Tyr Thr Asn Thr Thr Val Leu Ile Asp Lys Ile
            660                 665                 670

Glu Phe Leu Pro Ile Thr Arg Ser Ile Arg Glu Asp Arg Glu Lys Gln
            675                 680                 685

Lys Leu Glu Thr Val Gln Gln Ile Ile Asn Thr Phe Tyr Ala Asn Pro
            690                 695                 700

Ile Lys Asn Thr Leu Gln Ser Glu Leu Thr Asp Tyr Asp Ile Asp Gln
705                 710                 715                 720

Ala Ala Asn Leu Val Glu Cys Ile Ser Glu Leu Tyr Pro Lys Glu
                725                 730                 735

Lys Met Leu Leu Leu Asp Glu Val Lys Asn Ala Lys Gln Leu Ser Gln
            740                 745                 750

Ser Arg Asn Val Leu Gln Asn Gly Asp Phe Glu Ser Ala Thr Leu Gly
            755                 760                 765

Trp Thr Thr Ser Asp Asn Ile Thr Ile Gln Glu Asp Asp Pro Ile Phe
            770                 775                 780

Lys Gly His Tyr Leu His Met Ser Gly Ala Arg Asp Ile Asp Gly Thr
785                 790                 795                 800

Ile Phe Pro Thr Tyr Ile Phe Gln Lys Ile Asp Glu Ser Lys Leu Lys
                805                 810                 815

Pro Tyr Thr Arg Tyr Leu Val Arg Gly Phe Val Gly Ser Ser Lys Asp
            820                 825                 830

Val Glu Leu Val Val Ser Arg Tyr Gly Glu Glu Ile Asp Ala Ile Met
            835                 840                 845

Asn Val Pro Ala Asp Leu Asn Tyr Leu Tyr Pro Ser Thr Phe Asp Cys
850                 855                 860

Glu Gly Ser Asn Arg Cys Glu Thr Ser Ala Val Pro Ala Asn Ile Gly
865                 870                 875                 880

Asn Thr Ser Asp Met Leu Tyr Ser Cys Gln Tyr Asp Thr Gly Lys Lys
                885                 890                 895

His Val Val Cys Gln Asp Ser His Gln Phe Ser Phe Thr Ile Asp Thr
            900                 905                 910

Gly Ala Leu Asp Thr Asn Glu Asn Ile Gly Val Trp Val Met Phe Lys
            915                 920                 925

Ile Ser Ser Pro Asp Gly Tyr Ala Ser Leu Asp Asn Leu Glu Val Ile
            930                 935                 940

Glu Glu Gly Pro Ile Asp Gly Glu Ala Leu Ser Arg Val Lys His Met
945                 950                 955                 960

Glu Lys Lys Trp Asn Asp Gln Met Glu Ala Lys Arg Ser Glu Thr Gln
                965                 970                 975

Gln Ala Tyr Asp Val Ala Lys Gln Ala Ile Asp Ala Leu Phe Thr Asn
            980                 985                 990

Val Gln Asp Glu Ala Leu Gln Phe Asp Thr Thr Leu Ala Gln Ile Gln
            995                 1000                1005

Tyr Ala Glu Tyr Leu Val Gln Ser Ile Pro Tyr Val Tyr Asn Asp
            1010                1015                1020

Trp Leu Ser Asp Val Pro Gly Met Asn Tyr Asp Ile Tyr Val Glu
            1025                1030                1035

Leu Asp Ala Arg Val Ala Gln Ala Arg Tyr Leu Tyr Asp Thr Arg
            1040                1045                1050

Asn Ile Ile Lys Asn Gly Asp Phe Thr Gln Gly Val Met Gly Trp
            1055                1060                1065

His Val Thr Gly Asn Ala Asp Val Gln Gln Ile Asp Gly Val Ser

```
                  1070                1075                1080
Val Leu Val Leu Ser Asn Trp Ser Ala Gly Val Ser Gln Asn Val
        1085                1090                1095

His Leu Gln His Asn His Gly Tyr Val Leu Arg Val Ile Ala Lys
    1100                1105                1110

Lys Glu Gly Pro Gly Asn Gly Tyr Val Thr Leu Met Asp Cys Glu
    1115                1120                1125

Glu Asn Gln Glu Lys Leu Thr Phe Thr Ser Cys Glu Glu Gly Tyr
    1130                1135                1140

Ile Thr Lys Thr Val Asp Val Phe Pro Asp Thr Asp Arg Val Arg
    1145                1150                1155

Ile Glu Ile Gly Glu Thr Glu Gly Ser Phe Tyr Ile Glu Ser Ile
    1160                1165                1170

Glu Leu Ile Cys Met Asn Glu
    1175                1180

<210> SEQ ID NO 16
<211> LENGTH: 1245
<212> TYPE: PRT
<213> ORGANISM: Bacillus thuringiensis
<220> FEATURE:
<223> OTHER INFORMATION: Description of sequence: protein Cry5B from
      Fig. 27

<400> SEQUENCE: 16

Met Ala Thr Ile Asn Glu Leu Tyr Pro Val Pro Tyr Asn Val Leu Ala
1               5                   10                  15

His Pro Ile Lys Glu Val Asp Asp Pro Tyr Ser Trp Ser Asn Leu Leu
            20                  25                  30

Lys Gly Ile Gln Glu Gly Trp Glu Trp Gly Lys Thr Gly Gln Lys
        35                  40                  45

Lys Leu Phe Glu Asp His Leu Thr Ile Ala Trp Asn Leu Tyr Lys Thr
    50                  55                  60

Gly Lys Leu Asp Tyr Phe Ala Leu Thr Lys Ala Ser Ile Ser Leu Ile
65                  70                  75                  80

Gly Phe Ile Pro Gly Ala Glu Ala Ala Val Pro Phe Ile Asn Met Phe
                85                  90                  95

Val Asp Phe Val Trp Pro Lys Leu Phe Gly Ala Asn Thr Glu Gly Lys
            100                 105                 110

Asp Gln Gln Leu Phe Asn Ala Ile Met Asp Ala Val Asn Lys Met Val
        115                 120                 125

Asp Asn Lys Phe Leu Arg Tyr Asn Leu Ser Thr Leu Asn Lys Thr Ile
    130                 135                 140

Glu Gly Leu Gln Gly Asn Leu Gly Leu Phe Gln Asn Pro Ile Gln Val
145                 150                 155                 160

Ala Ile Cys Gln Gly Ser Thr Pro Glu Arg Val Ile Phe Asp Gln Asn
                165                 170                 175

Cys Thr Pro Cys Asn Pro Asn Gln Pro Cys Lys Asp Asp Leu Asp Arg
            180                 185                 190

Val Ala Ser Arg Phe Asp Thr Ala Asn Ser Gln Phe Thr Gln His Leu
        195                 200                 205

Pro Glu Phe Lys Asn Pro Trp Ser Asp Glu Asn Ser Thr Gln Glu Phe
    210                 215                 220

Lys Arg Thr Ser Val Glu Leu Thr Leu Pro Leu Tyr Thr Thr Val Ala
225                 230                 235                 240
```

-continued

```
Thr Leu His Leu Leu Leu Tyr Lys Gly Tyr Ile Glu Phe Met Thr Lys
                245                 250                 255

Trp Asn Phe His Asn Ala Gln Tyr Leu Asn Asn Leu Lys Val Glu Leu
            260                 265                 270

Gln Gln Leu Ile His Ser Tyr Ser Glu Thr Val Arg Thr Ser Phe Leu
        275                 280                 285

Gln Phe Leu Pro Thr Leu Asn Asn Arg Ser Lys Ser Ser Val Asn Ala
    290                 295                 300

Tyr Asn Gly Tyr Val Arg Asn Met Thr Val Asn Cys Leu Asp Ile Ala
305                 310                 315                 320

Ala Thr Trp Pro Thr Phe Asp Thr His Asn Tyr His Gln Gly Arg Lys
                325                 330                 335

Leu Asp Leu Thr Arg Ile Ile Leu Ser Asp Thr Ala Gly Pro Ile Lys
            340                 345                 350

Glu Tyr Thr Thr Gly Asp Lys Thr Ser Gly Pro Gln His Ser Asn Ile
        355                 360                 365

Thr Pro Asn Asn Ile Leu Asp Thr Pro Ser Pro Thr Tyr Gln His Ser
    370                 375                 380

Phe Val Ser Val Asp Ser Ile Val Tyr Ser Arg Lys Glu Leu Gln Gln
385                 390                 395                 400

Leu Asp Ile Ala Thr Tyr Ser Thr Asn Asn Ser Asn Asn Cys His Pro
                405                 410                 415

Tyr Gly Leu Arg Leu Ser Tyr Thr Asp Gly Ser Arg Tyr Asp Tyr Gly
            420                 425                 430

Asp Asn Gln Pro Asp Phe Thr Thr Ser Asn Asn Asn Tyr Cys His Asn
        435                 440                 445

Ser Tyr Thr Ala Pro Ile Thr Leu Val Asn Ala Arg His Leu Tyr Asn
    450                 455                 460

Ala Lys Gly Ser Leu Gln Asn Val Glu Ser Leu Val Val Ser Thr Val
465                 470                 475                 480

Asn Gly Gly Ser Gly Ser Cys Ile Cys Asp Ala Trp Ile Asn Tyr Leu
                485                 490                 495

Arg Pro Pro Gln Thr Ser Lys Asn Glu Ser Arg Pro Asp Gln Lys Ile
            500                 505                 510

Asn Val Leu Tyr Pro Ile Thr Glu Thr Val Asn Lys Gly Thr Gly Gly
        515                 520                 525

Asn Leu Gly Val Ile Ser Ala Tyr Val Pro Met Glu Leu Val Pro Glu
    530                 535                 540

Asn Val Ile Gly Asp Val Asn Ala Asp Thr Lys Leu Pro Leu Thr Gln
545                 550                 555                 560

Leu Lys Gly Phe Pro Phe Glu Lys Tyr Gly Ser Glu Tyr Asn Asn Arg
                565                 570                 575

Gly Ile Ser Leu Val Arg Glu Trp Ile Asn Gly Asn Asn Ala Val Lys
            580                 585                 590

Leu Ser Asn Ser Gln Ser Val Gly Ile Gln Ile Thr Asn Gln Thr Lys
        595                 600                 605

Gln Lys Tyr Glu Ile Arg Cys Arg Tyr Ala Ser Lys Gly Asp Asn Asn
    610                 615                 620

Val Tyr Phe Asn Val Asp Leu Ser Glu Asn Pro Phe Arg Asn Ser Ile
625                 630                 635                 640

Ser Phe Gly Ser Thr Glu Ser Ser Val Val Gly Val Gln Gly Glu Asn
                645                 650                 655

Gly Lys Tyr Ile Leu Lys Ser Ile Thr Thr Val Glu Ile Pro Ala Gly
```

```
                    660                 665                 670
Ser Phe Tyr Val His Ile Thr Asn Gln Gly Ser Ser Asp Leu Phe Leu
            675                 680                 685

Asp Arg Ile Glu Phe Val Pro Lys Ile Gln Phe Gln Phe Cys Asp Asn
690                 695                 700

Asn Asn Leu His Cys Asp Cys Asn Asn Pro Val Asp Thr Asp Cys Thr
705                 710                 715                 720

Phe Cys Cys Val Cys Thr Ser Leu Thr Asp Cys Asp Cys Asn Asn Pro
                    725                 730                 735

Arg Gly Leu Asp Cys Thr Leu Cys Cys Gln Val Glu Asn Gln Leu Pro
                740                 745                 750

Ser Phe Val Thr Leu Thr Asp Leu Gln Asn Ile Thr Thr Gln Val Asn
                755                 760                 765

Ala Leu Val Ala Ser Ser Glu His Asp Thr Leu Ala Thr Asp Val Ser
                770                 775                 780

Asp Tyr Glu Ile Glu Glu Val Val Leu Lys Val Asp Ala Leu Ser Gly
785                 790                 795                 800

Glu Val Phe Gly Lys Glu Lys Lys Ala Leu Arg Lys Leu Val Asn His
                    805                 810                 815

Thr Lys Arg Leu Ser Lys Ala Arg Asn Leu Leu Ile Gly Gly Asn Phe
                820                 825                 830

Asp Asn Leu Asp Ala Trp Tyr Arg Gly Arg Asn Val Val Asn Val Ser
            835                 840                 845

Asp His Glu Leu Phe Lys Ser Asp His Val Leu Leu Pro Pro Pro Thr
            850                 855                 860

Leu Tyr Ser Ser Tyr Met Phe Gln Lys Val Glu Glu Ser Lys Leu Lys
865                 870                 875                 880

Ala Asn Thr Arg Tyr Thr Val Ser Gly Phe Ile Ala His Ala Glu Asp
                    885                 890                 895

Leu Glu Ile Val Val Ser Arg Tyr Gly Gln Glu Val Lys Lys Val Val
                900                 905                 910

Gln Val Pro Tyr Gly Glu Ala Phe Pro Leu Thr Ser Arg Gly Ala Ile
                915                 920                 925

Cys Cys Pro Pro Arg Ser Thr Cys Asn Gly Lys Pro Ala Asp Pro His
                930                 935                 940

Phe Phe Ser Tyr Ser Ile Asp Val Gly Thr Leu Asp Val Glu Ala Asn
945                 950                 955                 960

Pro Gly Ile Glu Leu Gly Leu Arg Ile Val Glu Arg Thr Gly Met Ala
                    965                 970                 975

Arg Val Ser Asn Leu Glu Ile Arg Glu Asp Arg Pro Leu Lys Lys Asn
                980                 985                 990

Glu Leu Arg Asn Val Gln Arg Ala Ala Arg Asn Trp Arg Thr Ala Tyr
                995                 1000                1005

Asp Gln Glu Arg Ala Glu Val Thr Ala Leu Ile Gln Pro Val Leu
    1010                1015                1020

Asn Gln Ile Asn Ala Leu Tyr Glu Asn Glu Asp Trp Asn Arg Ala
    1025                1030                1035

Ile Arg Ser Gly Val Ser Tyr His Asp Leu Glu Ala Ile Val Leu
    1040                1045                1050

Pro Thr Leu Pro Lys Leu Asn His Trp Phe Met Ser Asp Met Leu
    1055                1060                1065

Gly Glu Gln Gly Ser Ile Leu Ala Gln Phe Gln Glu Ala Leu Asp
    1070                1075                1080
```

```
Arg Ala Tyr Thr Gln Leu Glu  Glu Ser Thr Ile Leu  His Asn Gly
    1085                1090                1095

His Phe Thr Thr Asp Ala  Ala Asn Trp Thr Ile Glu  Gly Asp Ala
    1100                1105                1110

His His Ala Ile Leu Glu  Asp Gly Arg Arg Val Leu  Arg Leu Pro
    1115                1120                1125

Asp Trp Ser Ser Ser Val  Ser Gln Thr Ile Glu Ile  Glu Asn Phe
    1130                1135                1140

Asp Pro Asp Lys Glu Tyr  Gln Leu Val Phe His Ala  Gln Gly Glu
    1145                1150                1155

Gly Thr Val Ser Leu Gln  His Gly Glu Glu Gly Glu  Tyr Val Glu
    1160                1165                1170

Thr His Pro His Lys Ser  Ala Asn Phe Thr Thr Ser  His Arg Gln
    1175                1180                1185

Gly Val Thr Phe Glu Thr  Asn Lys Val Thr Val Glu  Ile Thr Ser
    1190                1195                1200

Glu Asp Gly Glu Phe Leu  Val Asp His Ile Ala Leu  Val Glu Ala
    1205                1210                1215

Pro Leu Pro Thr Asp Asp  Gln Ser Ser Asp Gly Asn  Thr Thr Ser
    1220                1225                1230

Asn Thr Asn Ser Asn Thr  Ser Met Asn Asn Asn Gln
    1235                1240                1245

<210> SEQ ID NO 17
<211> LENGTH: 609
<212> TYPE: PRT
<213> ORGANISM: Bacillus thuringiensis
<220> FEATURE:
<223> OTHER INFORMATION: Description of sequence: protein Cry7Ca1 from
      Fig. 27

<400> SEQUENCE: 17

Met Arg Gly Ser His His His His His His Gly Ser Met Ile Phe Ser
1               5                   10                  15

Ser Ile Ser Ile Ile Arg Thr Phe Met Gly Phe Ala Gly His Gly Thr
                20                  25                  30

Ala Gly Gly Ile Ile Gly Leu Phe Thr Glu Val Leu Arg Leu Leu Trp
            35                  40                  45

Pro Asn Lys Gln Asn Asp Leu Trp Glu Ser Phe Met Asn Glu Val Glu
        50                  55                  60

Ala Leu Ile Asn Gln Glu Ile Thr Glu Ala Val Val Ser Lys Ala Leu
65                  70                  75                  80

Ser Glu Leu Glu Gly Leu Arg Asn Ala Leu Glu Gly Tyr Thr Ser Ala
                85                  90                  95

Leu Glu Ala Trp Gln Asn Asn Arg Ser Asp Lys Leu Lys Gln Leu Leu
            100                 105                 110

Val Tyr Glu Arg Phe Val Ser Thr Glu Asn Leu Phe Lys Phe Ala Met
        115                 120                 125

Pro Ser Phe Arg Ser Val Gly Phe Glu Gly Pro Leu Leu Thr Val Tyr
    130                 135                 140

Ala Gln Ala Ala Asn Leu His Leu Phe Leu Leu Lys Asn Ala Glu Leu
145                 150                 155                 160

Phe Gly Ala Glu Trp Gly Met Gln Gln Tyr Glu Ile Asp Leu Phe Tyr
                165                 170                 175

Asn Glu Gln Lys Gly Tyr Val Glu Glu Tyr Thr Asp His Cys Val Lys
```

```
            180                 185                 190
Trp Tyr Lys Glu Gly Leu Asn Lys Leu Lys Asn Ala Ser Gly Val Lys
                195                 200                 205
Gly Lys Val Trp Glu Asn Tyr Asn Arg Phe Arg Arg Glu Met Thr Ile
        210                 215                 220
Met Val Leu Asp Leu Leu Pro Leu Phe Pro Ile Tyr Asp Ala Arg Thr
225                 230                 235                 240
Tyr Pro Met Glu Thr Val Thr Glu Leu Thr Arg Gln Ile Phe Thr Asp
                245                 250                 255
Pro Ile Gly Leu Thr Gly Ile Asn Glu Thr Lys Tyr Pro Asp Trp Tyr
            260                 265                 270
Gly Ala Ala Ser Ser Glu Phe Val Leu Ile Glu Asn Arg Ala Ile Pro
        275                 280                 285
Lys Pro Gly Leu Phe Gln Trp Leu Thr Lys Ile Asn Val Arg Ala Arg
    290                 295                 300
Val Val Glu Pro Asn Asp Arg Phe Ala Ile Trp Thr Gly His Ser Val
305                 310                 315                 320
Val Thr Gln Tyr Thr Lys Ser Thr Thr Glu Asn Thr Phe Asn Tyr Gly
                325                 330                 335
Thr Ser Ser Gly Ser Thr Leu Ser His Thr Phe Asp Leu Leu Ser Lys
            340                 345                 350
Asp Ile Tyr Gln Thr Tyr Ser Ile Ala Ala Ala Asn Lys Ser Ala Thr
            355                 360                 365
Trp Tyr Gln Ala Val Pro Leu Leu Arg Leu Tyr Gly Ile Asn Ser Ser
        370                 375                 380
Asn Val Leu Ser Glu Asp Ala Phe Ser Phe Ser Asn Asn Ile Pro Ser
385                 390                 395                 400
Ser Lys Cys Lys Ser Thr Tyr Ser Ser Asp Gln Leu Pro Ile Glu Leu
                405                 410                 415
Leu Asp Glu Pro Ile Tyr Gly Asp Leu Glu Glu Tyr Gly His Arg Leu
            420                 425                 430
Ser Tyr Val Ser Glu Ile Phe Lys Glu Thr Gly Ser Gly Thr Ile Pro
        435                 440                 445
Val Leu Gly Trp Thr His Val Ser Val Arg Pro Asp Asn Lys Leu Tyr
    450                 455                 460
Pro Asp Lys Ile Thr Gln Ile Pro Ala Val Lys Ala Phe Glu Thr Asn
465                 470                 475                 480
Thr Ala Gly Val Glu Ile Ile Asp Ser Ala Ser Thr Gly Gly Pro Ile
                485                 490                 495
Leu Lys Ile Val Asn Asn Asn Leu Pro Ser Asn Gln Val Phe Arg Met
            500                 505                 510
Arg Leu Ser Phe Ser Glu Pro Gln Lys Ile Lys Val Arg Val Arg Tyr
        515                 520                 525
Ala Ala Thr Gly Asp Gly Val Met Ser Phe Ser Gly Ile Ala His Asp
    530                 535                 540
Glu Tyr Phe Thr Ala Thr Met Lys Glu Gly Glu Ala Leu Lys Tyr Ser
545                 550                 555                 560
Tyr Leu Thr Met Gly Asn Asp Tyr Ala Gly Thr Ala Ala Glu Leu Ser
                565                 570                 575
Met Leu Tyr Ile Ile Lys Ala Asn Thr Ser Asn Cys Thr Ile Tyr Ile
            580                 585                 590
Asp Lys Ile Glu Phe Ile Pro Val Val Asp Leu Gln Pro Ser Leu Ile
        595                 600                 605
```

Ser

<210> SEQ ID NO 18
<211> LENGTH: 1164
<212> TYPE: PRT
<213> ORGANISM: Bacillus thuringiensis
<220> FEATURE:
<223> OTHER INFORMATION: Description of sequence: protein Cry8Ea1 from Fig. 27

<400> SEQUENCE: 18

```
Met Ser Pro Asn Asn Gln Asn Glu Tyr Glu Ile Ile Asp Met Ala Pro
1               5                   10                  15

Ser Thr Ser Val Ser Asn Asp Ser Asn Arg Tyr Pro Phe Ala Ser Asp
            20                  25                  30

Pro Thr Asn Ala Leu Gln Asn Met Asn Tyr Lys Glu Tyr Leu Arg Met
        35                  40                  45

Ser Glu Gly Tyr Asp Ser Glu Tyr Ser Gly Ser Pro Glu Val Leu Ile
    50                  55                  60

Ser Glu Arg Asp Ala Val Lys Thr Ala Ile Ser Leu Val Gly Thr Ile
65                  70                  75                  80

Leu Gly Lys Leu Gly Val Pro Leu Val Gly Pro Ile Val Ser Leu Tyr
                85                  90                  95

Ser Thr Leu Ile Asp Val Leu Trp Pro Gly Gly Lys Ser Gln Trp Glu
            100                 105                 110

Ile Phe Met Glu Gln Val Glu Ala Leu Ile Asn Gln Lys Ile Ala Glu
        115                 120                 125

Tyr Ala Arg Ala Lys Ala Leu Ala Glu Leu Glu Gly Leu Gly Asn Asn
    130                 135                 140

Tyr Gln Leu Tyr Leu Thr Ala Leu Glu Gly Trp Gln Glu Asn Pro Ser
145                 150                 155                 160

Ser Thr Arg Val Leu Arg Asp Val Arg Asn Arg Phe Glu Ile Leu Asp
                165                 170                 175

Ser Leu Phe Thr Gln Tyr Met Pro Ser Phe Arg Val Thr Gly Tyr Glu
            180                 185                 190

Val Pro Leu Leu Ser Val Tyr Ala Gln Ala Ala Asn Leu His Leu Leu
        195                 200                 205

Leu Leu Lys Asp Ala Ser Ile Phe Gly Glu Glu Trp Gly Phe Ser Thr
    210                 215                 220

Thr Ala Ile Asn Asn Tyr Tyr Asn Arg Gln Met Ser Leu Ile Ala Gln
225                 230                 235                 240

Tyr Ser Asp His Cys Val Gln Trp Tyr Arg Thr Gly Leu Asp Arg Leu
                245                 250                 255

Lys Gly Ser Asn Ala Lys Gln Trp Val Glu Tyr Asn Arg Phe Arg Arg
            260                 265                 270

Glu Met Thr Leu Ser Val Leu Asp Ile Met Thr Leu Phe Pro Met Tyr
        275                 280                 285

Asp Met Arg Thr Tyr Pro Met Glu Thr Lys Ala Gln Leu Thr Arg Glu
    290                 295                 300

Val Tyr Thr Asp Pro Ile Gly Ala Ile Gly Ala Gln Gly Ser Trp Tyr
305                 310                 315                 320

Asp Ser Ala Pro Ser Phe Asn Thr Leu Glu Ser Thr Phe Ile Arg Gly
                325                 330                 335

Lys His Leu Phe Asp Phe Ile Thr Arg Leu Ser Ile Tyr Thr Gly Arg
            340                 345                 350
```

-continued

Ser Ser Phe Ser Ala Ser Asn Tyr Leu Lys Lys Trp Ile Gly His Gln
        355                 360                 365

Ile Ser Ser Gln Pro Ile Gly Gly Ser Ile Gln Thr Gln Thr Tyr Gly
    370                 375                 380

Thr Thr Ser Gly Ser Ser Val Ile Ala Thr Gln Gln Ile Gly Phe Thr
385                 390                 395                 400

Gly Phe Asp Val Tyr Lys Thr Leu Ser Thr Ala Gly Val Leu Phe Ala
                405                 410                 415

Tyr Thr Ser Lys Tyr Tyr Gly Val Ser Lys Val Val Phe Asp Ala Ile
                420                 425                 430

Tyr Pro Asp Asn Lys Tyr Lys Thr Thr Phe Thr Tyr Asn Pro Gly Ser
            435                 440                 445

Glu Gly Ile Gly Ala Gln Glu Lys Asp Ser Glu Val Glu Leu Pro Pro
        450                 455                 460

Glu Thr Leu Asp Gln Pro Asn Tyr Glu Ala Tyr Ser His Arg Leu Asn
465                 470                 475                 480

Tyr Val Thr Phe Ile Arg Asn Pro Asp Val Pro Val Phe Ser Trp Thr
                485                 490                 495

His Arg Ser Ala Asp Arg Thr Asn Thr Val Tyr Ser Asp Lys Ile Thr
            500                 505                 510

Gln Ile Pro Val Val Lys Ala Ser Asp Gly Pro Lys Pro Ser Ala Asn
        515                 520                 525

Glu Val Gly His Tyr Leu Gly Gly Asp Pro Ile Ser Phe Asn Ser Ser
    530                 535                 540

Gly Ser Thr Gly Val Ile Arg Leu Asn Ile Asn Ser Pro Leu Ser Gln
545                 550                 555                 560

Lys Tyr Arg Val Arg Ile Arg Tyr Cys Ser Ser Val Asp Phe Asp Leu
                565                 570                 575

Asp Val Val Arg Gly Gly Thr Thr Val Asn Asn Gly Arg Phe Asn Lys
            580                 585                 590

Ser Ala Pro Asn Val Gly Trp Gln Ser Leu Lys Tyr Glu Asn Phe Lys
        595                 600                 605

Phe Ala Ser Phe Ser Thr Pro Phe Thr Phe Asn Gln Ala Gln Asp Thr
    610                 615                 620

Leu Lys Ile Ser Val Arg Asn Phe Ser Ser Ile Val Gly Gly Ser Val
625                 630                 635                 640

Val Tyr Ile Asp Arg Ile Glu Leu Ile Pro Val Asn Ala Thr Tyr Glu
                645                 650                 655

Ala Glu Gln Asp Leu Asp Ser Ala Lys Lys Ala Val Asn Thr Leu Phe
            660                 665                 670

Thr Asn Thr Lys Asp Gly Leu Arg Pro Gly Val Thr Asp Tyr Glu Val
        675                 680                 685

Asn Gln Ala Ala Asn Leu Val Glu Cys Leu Ser Asp Asp Leu Tyr Pro
    690                 695                 700

Asn Glu Lys Arg Leu Leu Phe Asp Ala Val Lys Glu Ala Lys Arg Leu
705                 710                 715                 720

Ser Glu Ala Arg Asn Leu Leu Gln Asp Pro Asp Phe Gln Glu Ile Asn
                725                 730                 735

Gly Glu Asn Gly Trp Thr Ala Ser Thr Gly Ile Glu Val Val Glu Gly
            740                 745                 750

Asp Ala Leu Phe Lys Gly Arg Tyr Leu Arg Leu Pro Gly Ala Arg Glu
        755                 760                 765

-continued

Met Asp Thr Glu Thr Tyr Pro Thr Tyr Leu Tyr Gln Lys Val Glu
770             775                 780

Gly Val Leu Lys Pro Tyr Thr Arg Tyr Arg Leu Arg Gly Phe Val Gly
785                 790                 795                 800

Ser Ser Gln Gly Leu Glu Ile Ser Thr Ile Arg His Gln Thr Asn Arg
                805                 810                 815

Ile Val Lys Asn Val Pro Asp Asp Leu Leu Pro Asp Val Pro Pro Val
            820                 825                 830

Asn Ser Asp Gly Arg Ile Asn Arg Cys Ser Glu Gln Lys Tyr Val Asn
                835                 840                 845

Ser Arg Leu Glu Gly Glu Arg Gly Leu Pro Asn Gly Asn Arg Ser Ala
850                 855                 860

Glu Ala His Glu Phe Ser Leu Pro Ile Asp Ile Gly Glu Leu Asp Tyr
865                 870                 875                 880

Asn Glu Asn Ala Gly Ile Trp Val Gly Phe Lys Ile Thr Asp Pro Glu
                885                 890                 895

Gly Tyr Ala Thr Leu Gly Asn Leu Glu Leu Val Glu Glu Gly Pro Leu
                900                 905                 910

Ser Gly Asp Ala Leu Glu Arg Leu Gln Arg Glu Glu Gln Trp Lys
                915                 920                 925

Leu Gln Met Thr Lys Arg Arg Glu Glu Thr Asp Arg Lys Tyr Thr Ala
930                 935                 940

Ala Lys Gln Ala Val Asp Arg Leu Tyr Ala Asp Tyr Gln Asp Gln Gln
945                 950                 955                 960

Leu Asn Pro Asn Val Glu Ile Thr Asp Ile Thr Ala Ala Gln Asn Leu
                965                 970                 975

Ile Gln Ser Ile Pro Tyr Val Tyr Asn Glu Met Phe Pro Glu Ile Gln
                980                 985                 990

Gly Met Asn Tyr Thr Lys Tyr Thr Glu Leu Thr Asn Arg Leu Gln Gln
                995                 1000                1005

Ala Trp Gly Leu Tyr Asp Gln Arg Asn Ala Ile Pro  Asn Gly Asp
    1010                1015                1020

Phe Arg Asn Glu Leu Ser Asn Trp Asn Thr Thr Ser  Gly Val Asn
    1025                1030                1035

Val Gln Gln Ile Asn Asn Thr Ser Val Leu Val Met Pro Asn Trp
    1040                1045                1050

Asp Gly Gln Val Ser Gln Gln Phe Thr Val Gln Pro Asn Gln Arg
    1055                1060                1065

Tyr Val Leu Arg Val Thr Ala Arg Lys Glu Gly Val  Gly Asn Gly
    1070                1075                1080

Tyr Val Ser Ile Arg Asp Gly Gly Asn Gln Thr Glu  Thr Leu Thr
    1085                1090                1095

Phe Ser Ala Ser Asp Tyr Asn Thr Asp Ser Val Tyr  Asn Thr Gln
    1100                1105                1110

Val Ser Asn Thr Asn Gly Leu Tyr Asn Glu Gln Thr  Gly Tyr Thr
    1115                1120                1125

Thr Lys Thr Val Thr Phe Ile Pro Tyr Thr Asp Gln Val Trp Ile
    1130                1135                1140

Glu Met Ser Glu Thr Glu Gly Met Phe Tyr Ile Glu  Ser Val Glu
    1145                1150                1155

Leu Ile Val Asp Val Glu
    1160

```
<210> SEQ ID NO 19
<211> LENGTH: 675
<212> TYPE: PRT
<213> ORGANISM: Bacillus thuringiensis
<220> FEATURE:
<223> OTHER INFORMATION: Description of sequence: protein Cry10Aa from
      Fig. 27

<400> SEQUENCE: 19

Met Asn Pro Tyr Gln Asn Lys Asn Glu Tyr Glu Ile Phe Asn Ala Pro
1               5                   10                  15

Ser Asn Gly Phe Ser Lys Ser Asn Asn Tyr Ser Arg Tyr Pro Leu Ala
            20                  25                  30

Asn Lys Pro Asn Gln Pro Leu Lys Asn Thr Asn Tyr Lys Asp Trp Leu
        35                  40                  45

Asn Val Cys Gln Asp Asn Gln Gln Tyr Gly Asn Asn Ala Gly Asn Phe
    50                  55                  60

Ala Ser Ser Glu Thr Ile Val Gly Val Ser Ala Gly Ile Ile Val Val
65              70                  75                  80

Gly Thr Met Leu Gly Ala Phe Ala Ala Pro Val Leu Ala Ala Gly Ile
                85                  90                  95

Ile Ser Phe Gly Thr Leu Leu Pro Ile Phe Trp Gln Gly Ser Asp Pro
            100                 105                 110

Ala Asn Val Trp Gln Asp Leu Leu Asn Ile Gly Gly Arg Pro Ile Gln
        115                 120                 125

Glu Ile Asp Lys Asn Ile Ile Asn Val Leu Thr Ser Ile Val Thr Pro
130                 135                 140

Ile Lys Asn Gln Leu Asp Lys Tyr Gln Glu Phe Phe Asp Lys Trp Glu
145                 150                 155                 160

Pro Ala Arg Thr His Ala Asn Ala Lys Ala Val His Asp Leu Phe Thr
                165                 170                 175

Thr Leu Glu Pro Ile Ile Asp Lys Asp Leu Asp Met Leu Lys Asn Asn
            180                 185                 190

Ala Ser Tyr Arg Ile Pro Thr Leu Pro Ala Tyr Ala Gln Ile Ala Thr
        195                 200                 205

Trp His Leu Asn Leu Leu Lys His Ala Ala Thr Tyr Tyr Asn Ile Trp
    210                 215                 220

Leu Gln Asn Gln Gly Ile Asn Pro Ser Thr Phe Asn Ser Ser Asn Tyr
225                 230                 235                 240

Tyr Gln Gly Tyr Leu Lys Arg Lys Ile Gln Glu Tyr Thr Asp Tyr Cys
                245                 250                 255

Ile Gln Thr Tyr Asn Ala Gly Leu Thr Met Ile Arg Thr Asn Thr Asn
            260                 265                 270

Ala Thr Trp Asn Met Tyr Asn Thr Tyr Arg Leu Glu Met Thr Leu Thr
        275                 280                 285

Val Leu Asp Leu Ile Ala Ile Phe Pro Asn Tyr Asp Pro Glu Lys Tyr
    290                 295                 300

Pro Ile Gly Val Lys Ser Glu Leu Ile Arg Glu Val Tyr Thr Asn Val
305                 310                 315                 320

Asn Ser Asp Thr Phe Arg Thr Ile Thr Glu Leu Glu Asn Gly Leu Thr
                325                 330                 335

Arg Asn Pro Thr Leu Phe Thr Trp Ile Asn Gln Gly Arg Phe Tyr Thr
            340                 345                 350

Arg Asn Ser Arg Asp Ile Leu Asp Pro Tyr Asp Ile Phe Ser Phe Thr
        355                 360                 365
```

```
Gly Asn Gln Met Ala Phe Thr His Thr Asn Asp Asp Arg Asn Ile Ile
    370                 375                 380

Trp Gly Ala Val His Gly Asn Ile Ile Ser Gln Asp Thr Ser Lys Val
385                 390                 395                 400

Phe Pro Phe Tyr Arg Asn Lys Pro Ile Asp Lys Val Glu Ile Val Arg
                405                 410                 415

His Arg Glu Tyr Ser Asp Ile Ile Tyr Glu Met Ile Phe Phe Ser Asn
            420                 425                 430

Ser Ser Glu Val Phe Arg Tyr Ser Asn Ser Thr Ile Glu Asn Asn
        435                 440                 445

Tyr Lys Arg Thr Asp Ser Tyr Met Ile Pro Lys Gln Thr Trp Lys Asn
450                 455                 460

Glu Glu Tyr Gly His Thr Leu Ser Tyr Ile Lys Thr Asp Asn Tyr Ile
465                 470                 475                 480

Phe Ser Val Val Arg Glu Arg Arg Val Ala Phe Ser Trp Thr His
                485                 490                 495

Thr Ser Val Asp Phe Gln Asn Thr Ile Asp Leu Asp Asn Ile Thr Gln
                500                 505                 510

Ile His Ala Leu Lys Ala Leu Lys Val Ser Ser Asp Ser Lys Ile Val
        515                 520                 525

Lys Gly Pro Gly His Thr Gly Gly Asp Leu Val Ile Leu Lys Asp Ser
530                 535                 540

Met Asp Phe Arg Val Arg Phe Leu Lys Asn Val Ser Arg Gln Tyr Gln
545                 550                 555                 560

Val Arg Ile Arg Tyr Ala Thr Asn Ala Pro Lys Thr Val Phe Leu
                565                 570                 575

Thr Gly Ile Asp Thr Ile Ser Val Glu Leu Pro Ser Thr Thr Ser Arg
                580                 585                 590

Gln Asn Pro Asn Ala Thr Asp Leu Thr Tyr Ala Asp Phe Gly Tyr Val
            595                 600                 605

Thr Phe Pro Arg Thr Val Pro Asn Lys Thr Phe Glu Gly Glu Asp Thr
        610                 615                 620

Leu Leu Met Thr Leu Tyr Gly Thr Pro Asn His Ser Tyr Asn Ile Tyr
625                 630                 635                 640

Ile Asp Lys Ile Glu Phe Ile Pro Ile Thr Gln Ser Val Leu Asp Tyr
                645                 650                 655

Thr Glu Lys Gln Asn Ile Glu Lys Thr Gln Lys Ile Val Asn Asp Leu
            660                 665                 670

Phe Val Asn
        675

<210> SEQ ID NO 20
<211> LENGTH: 643
<212> TYPE: PRT
<213> ORGANISM: Bacillus thuringiensis
<220> FEATURE:
<223> OTHER INFORMATION: Description of sequence: protein Cry11Aa from
      Fig. 27

<400> SEQUENCE: 20

Met Glu Asp Ser Ser Leu Asp Thr Leu Ser Ile Val Asn Glu Thr Asp
1               5                   10                  15

Phe Pro Leu Tyr Asn Asn Tyr Thr Glu Pro Thr Ile Ala Pro Ala Leu
                20                  25                  30

Ile Ala Val Ala Pro Ile Ala Gln Tyr Leu Ala Thr Ala Ile Gly Lys
            35                  40                  45
```

```
Trp Ala Ala Lys Ala Ala Phe Ser Lys Val Leu Ser Leu Ile Phe Pro
 50                  55                  60

Gly Ser Gln Pro Ala Thr Met Glu Lys Val Arg Thr Glu Val Glu Thr
 65                  70                  75                  80

Leu Ile Asn Gln Lys Leu Ser Gln Asp Arg Val Asn Ile Leu Asn Ala
                 85                  90                  95

Glu Tyr Arg Gly Ile Ile Glu Val Ser Asp Val Phe Asp Ala Tyr Ile
                100                 105                 110

Lys Gln Pro Gly Phe Thr Pro Ala Thr Ala Lys Gly Tyr Phe Leu Asn
            115                 120                 125

Leu Ser Gly Ala Ile Ile Gln Arg Leu Pro Gln Phe Glu Val Gln Thr
            130                 135                 140

Tyr Glu Gly Val Ser Ile Ala Leu Phe Thr Gln Met Cys Thr Leu His
145                 150                 155                 160

Leu Thr Leu Leu Lys Asp Gly Ile Leu Ala Gly Ser Ala Trp Gly Phe
                165                 170                 175

Thr Gln Ala Asp Val Asp Ser Phe Ile Lys Leu Phe Asn Gln Lys Val
            180                 185                 190

Leu Asp Tyr Arg Thr Arg Leu Met Arg Met Tyr Thr Glu Glu Phe Gly
            195                 200                 205

Arg Leu Cys Lys Val Ser Leu Lys Asp Gly Leu Thr Phe Arg Asn Met
210                 215                 220

Cys Asn Leu Tyr Val Phe Pro Phe Ala Glu Ala Trp Ser Leu Met Arg
225                 230                 235                 240

Tyr Glu Gly Leu Lys Leu Gln Ser Ser Leu Ser Leu Trp Asp Tyr Val
                245                 250                 255

Gly Val Ser Ile Pro Val Asn Tyr Asn Glu Trp Gly Gly Leu Val Tyr
            260                 265                 270

Lys Leu Leu Met Gly Glu Val Asn Gln Arg Leu Thr Thr Val Lys Phe
            275                 280                 285

Asn Tyr Ser Phe Thr Asn Glu Pro Ala Asp Ile Pro Ala Arg Glu Asn
            290                 295                 300

Ile Arg Gly Val His Pro Ile Tyr Asp Pro Ser Ser Gly Leu Thr Gly
305                 310                 315                 320

Trp Ile Gly Asn Gly Arg Thr Asn Asn Phe Asn Phe Ala Asp Asn Asn
                325                 330                 335

Gly Asn Glu Ile Met Glu Val Arg Thr Gln Thr Phe Tyr Gln Asn Pro
            340                 345                 350

Asn Asn Glu Pro Ile Ala Pro Arg Asp Ile Ile Asn Gln Ile Leu Thr
            355                 360                 365

Ala Pro Ala Pro Ala Asp Leu Phe Phe Lys Asn Ala Asp Ile Asn Val
            370                 375                 380

Lys Phe Thr Gln Trp Phe Gln Ser Thr Leu Tyr Gly Trp Asn Ile Lys
385                 390                 395                 400

Leu Gly Thr Gln Thr Val Leu Ser Ser Arg Thr Gly Thr Ile Pro Pro
                405                 410                 415

Asn Tyr Leu Ala Tyr Asp Gly Tyr Tyr Ile Arg Ala Ile Ser Ala Cys
            420                 425                 430

Pro Arg Gly Val Ser Leu Ala Tyr Asn His Asp Leu Thr Thr Leu Thr
            435                 440                 445

Tyr Asn Arg Ile Glu Tyr Asp Ser Pro Thr Thr Glu Asn Ile Ile Val
450                 455                 460
```

| | | | | | | | | | | | | | | |
|---|---|---|---|---|---|---|---|---|---|---|---|---|---|---|
| Gly | Phe | Ala | Pro | Asp | Asn | Thr | Lys | Asp | Phe | Tyr | Ser | Lys | Lys | Ser | His |
| 465 | | | | 470 | | | | 475 | | | | | | | 480 |
| Tyr | Leu | Ser | Glu | Thr | Asn | Asp | Ser | Tyr | Val | Ile | Pro | Ala | Leu | Gln | Phe |
| | | | | 485 | | | | | 490 | | | | | 495 | |
| Ala | Glu | Val | Ser | Asp | Arg | Ser | Phe | Leu | Glu | Asp | Thr | Pro | Asp | Gln | Ala |
| | | | 500 | | | | | 505 | | | | | 510 | | |
| Thr | Asp | Gly | Ser | Ile | Lys | Phe | Ala | Arg | Thr | Phe | Ile | Ser | Asn | Glu | Ala |
| | | 515 | | | | | 520 | | | | | 525 | | | |
| Lys | Tyr | Ser | Ile | Arg | Leu | Asn | Thr | Gly | Phe | Asn | Thr | Ala | Thr | Arg | Tyr |
| | 530 | | | | | 535 | | | | 540 | | | | | |
| Lys | Leu | Ile | Ile | Arg | Val | Arg | Val | Pro | Tyr | Arg | Leu | Pro | Ala | Gly | Ile |
| 545 | | | | | 550 | | | | | 555 | | | | | 560 |
| Arg | Val | Gln | Ser | Gln | Asn | Ser | Gly | Asn | Asn | Arg | Met | Leu | Gly | Ser | Phe |
| | | | | 565 | | | | | 570 | | | | | 575 | |
| Thr | Ala | Asn | Ala | Asn | Pro | Glu | Trp | Val | Asp | Phe | Val | Thr | Asp | Ala | Phe |
| | | | | 580 | | | | | 585 | | | | | 590 | |
| Thr | Phe | Asn | Asp | Leu | Gly | Ile | Thr | Thr | Ser | Ser | Thr | Asn | Ala | Leu | Phe |
| | | 595 | | | | | 600 | | | | | 605 | | | |
| Ser | Ile | Ser | Ser | Asp | Ser | Leu | Asn | Ser | Gly | Glu | Glu | Trp | Tyr | Leu | Ser |
| | 610 | | | | | 615 | | | | | 620 | | | | |
| Gln | Leu | Phe | Leu | Val | Lys | Glu | Ser | Ala | Phe | Thr | Thr | Gln | Ile | Asn | Pro |
| 625 | | | | | 630 | | | | | 635 | | | | | 640 |
| Leu | Leu | Lys | | | | | | | | | | | | | |

What is claimed is:

1. A method for recombinantly expressing a protein, comprising:
  (1) obtaining bacterial cells comprising an expression cassette encoding the protein and an expression cassette encoding a modified Cry protein, wherein the bacterial cells are *Bacillus subtilis* (Bs), *Bacillus thuringiensis* (Bt), or *Escherichia coli* (*E. coli*) cells, (2) culturing the bacterial cells under conditions permissible for the expression of the protein and the modified Cry protein, thereby expressing separately the protein and the modified Cry protein, and (3) permitting the modified Cry protein to form crystal containing the protein in the bacterial cells, wherein the modified Cry protein comprises the amino acid sequence set forth in SEQ ID NO:4, which is modified to comprise:

(i) substitutions with aspartate (D) or glutamate (E) at residues K384, N391, N395, S425, Q430, T436, Q437, K442, R443, T461, and K467;

(ii) addition of the amino acid sequence set forth in SEQ ID NO:8 in 1-3 repeats at the C-terminus;

(iii) one or more deletions in segment 110-128, 181-197, 211-226, 250-264, 423-436, 457-471, 593-598, or 627-632;

(iv) one or more substitutions at residue 5145 or H161, or (v) the amino acid sequence set forth in SEQ ID NO:5.

2. The method of claim 1, wherein the protein is an enzyme.

3. The method of claim 2, wherein the enzyme is a lipase, ligase, hydrolase, esterase, protease, or glycosidase.

4. The method of claim 3, wherein the lipase is a *Proteus mirabilis* lipase (PML), an I118V+E130G mutant of PML ($PML^{VG}$), a *Bacillus subtilis* lipase A (lipA), or a lipase A fused to a polyarginine tail comprising nine consecutive arginine residues (lipAR9).

5. The method of claim 1, wherein the modified cry protein comprises the amino acid sequence set forth in SEQ ID NO:6.

6. The method of claim 1, wherein the expression cassette encoding the protein and the expression cassette encoding the modified Cry protein are one single expression cassette.

7. The method of claim 6, wherein the one single expression cassette comprises (1) one copy of polynucleotide sequence encoding the modified Cry protein and (2) one copy or two or more copies of polynucleotide sequence encoding the protein.

8. The method of claim 7, wherein (1) the polynucleotide sequence encoding the modified Cry protein and (2) the polynucleotide sequence encoding the protein are operably linked to one single promoter.

9. The method of claim 8, wherein the one single promoter is operably linked to (1) one copy of the polynucleotide sequence encoding the modified Cry protein, followed by (2) one copy of the polynucleotide sequence encoding the protein, with one ribosome binding site between (1) and (2).

10. The method of claim 8, wherein the one single promoter is operably linked to (1) one copy of the polynucleotide sequence encoding the modified Cry protein, followed by (2) two or more copies of the polynucleotide sequence encoding the protein, with one ribosome binding site between (1) and (2) and between two copies of polynucleotide sequence encoding the protein.

11. The method of claim 7, wherein (1) the polynucleotide sequence encoding the modified Cry protein and (2) the polynucleotide sequence encoding the protein are operably linked to two separate promoters.

12. The method of claim 11, wherein the two separate promoters are two different promoters.

13. The method of claim 11, wherein (1) the polynucleotide sequence encoding the modified Cry protein and (2)

the polynucleotide sequence encoding the protein share one single termination codon, resulting in one copy of the modified Cry protein and two copies of the protein being expressed.

14. The method of claim 1, wherein the expression cassette encoding the protein and the expression cassette encoding the modified Cry protein are two separate expression cassettes.

15. The method of claim 1, wherein the modified Cry protein comprises the amino acid sequence set forth in SEQ ID NO:7.

16. The method of claim 1, wherein the modified Cry protein comprises the amino acid sequence set forth in SEQ ID NO:8 fused to the C-terminus of the amino acid sequence set forth in SEQ ID NO:4.

17. The method of claim 1, wherein two or more proteins are expressed with the modified Cry protein and are contained within the crystal formed by the modified Cry protein.

18. The method of claim 1, wherein the modified Cry protein comprises the amino acid sequence set forth in SEQ ID NO:9.

19. The method of claim 1, further comprising, prior to step (1), introducing into the bacterial cells the expression cassette encoding the protein and the expression cassette encoding the modified Cry protein.

20. The method of claim 1, further comprising, after step (3), isolating the crystal formed by the modified Cry protein containing the protein.

21. The method of claim 20, further comprising, after the isolating step, washing the crystal under conditions permissible for releasing the protein from the crystal, thereby releasing from the crystal and isolating the protein.

22. The method of claim 20, wherein the protein is an enzyme.

23. The method of claim 1, wherein the bacterial cells are *Bacillus thuringiensis* (Bt) cells.

\* \* \* \* \*